United States Patent
Baek et al.

(10) Patent No.: US 11,474,104 B2
(45) Date of Patent: *Oct. 18, 2022

(54) METHODS OF IDENTIFICATION, ASSESSMENT, PREVENTION AND THERAPY OF LUNG DISEASES AND KITS THEREOF INCLUDING GENDER-BASED DISEASE IDENTIFICATION, ASSESSMENT, PREVENTION AND THERAPY

(71) Applicant: CANCER PREVENTION AND CURE, LTD., Michigan City, IN (US)

(72) Inventors: Sung H. Baek, Snohomish, WA (US); Robert T. Streeper, San Antonio, TX (US); Elzbieta Izbicka, San Antonio, TX (US)

(73) Assignee: CANCER PREVENTION AND CURE, LTD., Michigan City, IN (US)

( * ) Notice: Subject to any disclaimer, the term of this patent is extended or adjusted under 35 U.S.C. 154(b) by 20 days.

This patent is subject to a terminal disclaimer.

(21) Appl. No.: 15/941,046

(22) Filed: Mar. 30, 2018

(65) Prior Publication Data

US 2018/0356423 A1  Dec. 13, 2018

Related U.S. Application Data

(63) Continuation of application No. 13/256,630, filed as application No. PCT/US2010/027243 on Mar. 12, 2010, now Pat. No. 9,933,429, which is a continuation-in-part of application No. 12/403,369, filed on Mar. 12, 2009, now Pat. No. 8,541,183.

(60) Provisional application No. 61/237,198, filed on Aug. 26, 2009.

(51) Int. Cl.
   *G01N 31/00* (2006.01)
   *G01N 33/53* (2006.01)
   *G01N 33/574* (2006.01)

(52) U.S. Cl.
   CPC ............ *G01N 33/57423* (2013.01); *G01N 2333/96494* (2013.01); *G01N 2800/12* (2013.01); *G01N 2800/60* (2013.01)

(58) Field of Classification Search
   CPC .... A61K 23/00; A61K 45/06; C07K 16/2863; C12Q 1/6886
   See application file for complete search history.

(56) References Cited

U.S. PATENT DOCUMENTS

| | | | |
|---|---|---|---|
| 6,939,670 B2 | 9/2005 | Pressman et al. | |
| 7,288,249 B2 | 10/2007 | Carter et al. | |
| 7,612,131 B2 | 11/2009 | Wu et al. | |
| 7,624,076 B2 | 11/2009 | Movellan et al. | |
| 7,845,050 B2 | 12/2010 | Pyo | |
| 7,888,051 B2 * | 2/2011 | Streeper .......... | G01N 33/57423 435/7.1 |
| 8,541,183 B2 * | 9/2013 | Streeper .......... | G01N 33/57423 435/7.1 |
| 8,771,963 B2 | 7/2014 | Nakamura et al. | |
| 9,852,269 B2 | 12/2017 | Sakagawa et al. | |
| 9,933,429 B2 * | 4/2018 | Baek ................ | G01N 33/57423 |
| 9,952,220 B2 | 4/2018 | Michalek et al. | |
| 10,359,425 B2 | 7/2019 | Gold et al. | |
| 2003/0104499 A1 | 6/2003 | Pressman et al. | |
| 2003/0134339 A1 | 7/2003 | Brown | |
| 2003/0190602 A1 | 10/2003 | Pressman et al. | |
| 2006/0024692 A1 | 2/2006 | Nakamura et al. | |
| 2006/0084126 A1 | 4/2006 | Segal | |
| 2006/0088894 A1 | 4/2006 | Wright et al. | |
| 2006/0252057 A1 | 11/2006 | Raponi et al. | |
| 2007/0071675 A1 | 3/2007 | Wu et al. | |
| 2007/0092917 A1 | 4/2007 | Guyon | |
| 2008/0109389 A1 | 5/2008 | Polyak et al. | |
| 2008/0133141 A1 | 6/2008 | Frost | |
| 2009/0069189 A1 | 3/2009 | Streeper et al. | |
| 2010/0009386 A1 | 1/2010 | Streeper et al. | |
| 2012/0021946 A1 | 1/2012 | Nakamura | |
| 2015/0031561 A1 | 1/2015 | Bertenshaw et al. | |
| 2017/0073763 A1 | 3/2017 | Diehn et al. | |

FOREIGN PATENT DOCUMENTS

| | | |
|---|---|---|
| CN | 1346279 | 4/2002 |
| CN | 1621829 | 6/2005 |
| CN | 1705753 | 7/2005 |
| CN | 1977052 | 6/2007 |
| CN | 101346626 | 1/2009 |
| CN | 101587125 | 11/2009 |
| CN | 101978269 | 2/2011 |

(Continued)

OTHER PUBLICATIONS

Orditura et al. Journal of Interferon & Cytokine Research, vol. 22, pp. 1129-1135, 2002 (Year: 2002).*
Linkov et al. (European Cytokine Network, 2009, 20(1), pp. 21-26). (Year: 2009).*
Orditura et al. Journal of Interferon & Cytokine Research, vol. 22, pp. 1129-1135, 2002—IDS filed Mar. 12, 2019) (Year: 2002).*
AU Exam Report from AU 2010223911 Exam Rpt. dated Dec. 19, 2014.
Bosse et al., Am J Respir and Crit Care Med, 1999, 159:596-602.
Camilla et al., Clin Diag Lab Immun, 2001, 8:776-784 (Abstract).
Chiu et al., Am J Resp Cell Mol Bio, 2003, 29:106-116.
Chung et al., Thorax, 1999, 54:825-857.
Cohen et al., Am J Phys, 2006, 290(6):L1097-L1103.
Dai et al., Sci Chin Series C: Life Sci, 2007, 50(3):305-311.

(Continued)

*Primary Examiner* — Lisa V Cook
(74) *Attorney, Agent, or Firm* — Arentfox Schiff LLP

(57) ABSTRACT

The invention provides biomarkers and combinations of biomarkers useful in diagnosing lung diseases such as non-small cell lung cancer or reactive airway disease. The invention also provides methods of differentiating lung disease, methods of monitoring therapy, and methods of predicting a subject's response to therapeutic intervention based on the extent of expression of the biomarkers and combinations of biomarkers. Kits comprising agents for detecting the biomarkers and combination of biomarkers are also provided.

16 Claims, 32 Drawing Sheets

Specification includes a Sequence Listing.

(56) References Cited

FOREIGN PATENT DOCUMENTS

| | | |
|---|---|---|
| CN | 101988059 | 3/2011 |
| CN | 102037355 | 4/2011 |
| JP | 2002542485 | 12/2002 |
| JP | 2004526154 | 8/2004 |
| JP | 2006509186 | 3/2006 |
| JP | 2009501318 | 1/2009 |
| JP | 2009524008 | 6/2009 |
| JP | 2010523979 | 7/2010 |
| JP | 2011506917 | 3/2011 |
| WO | 1998035985 | 8/1998 |
| WO | 2000063698 | 10/2000 |
| WO | WO 2000-063698 | 10/2000 |
| WO | 2002073204 | 9/2002 |
| WO | WO 2002-073204 | 9/2002 |
| WO | 2003087840 | 10/2003 |
| WO | 2003101283 A2 | 12/2003 |
| WO | 2004030511 | 4/2004 |
| WO | 2004031413 | 4/2004 |
| WO | WO 2004-031413 | 4/2004 |
| WO | 2005003164 | 1/2005 |
| WO | WO 2005-003164 | 1/2005 |
| WO | 2005090603 | 9/2005 |
| WO | WO 2005-090603 | 9/2005 |
| WO | 2005098445 | 10/2005 |
| WO | 2006045318 | 5/2006 |
| WO | WO 2006-045318 | 5/2006 |
| WO | 2006118522 | 11/2006 |
| WO | WO 2006-118522 | 11/2006 |
| WO | 2007002677 | 1/2007 |
| WO | 2007013671 | 2/2007 |
| WO | WO 2007-013671 | 2/2007 |
| WO | 2007026773 | 3/2007 |
| WO | 2007064964 | 6/2007 |
| WO | 2008063413 | 5/2008 |
| WO | WO 2008-063413 | 5/2008 |
| WO | 2008106200 | 9/2008 |
| WO | WO 2008-106200 | 9/2008 |
| WO | 2008124138 | 10/2008 |
| WO | 2009006323 | 1/2009 |
| WO | WO 2009-006323 | 1/2009 |
| WO | 2009036123 | 3/2009 |
| WO | WO 2009-036123 | 3/2009 |
| WO | 2009074276 | 6/2009 |
| WO | 2010030697 | 3/2010 |
| WO | 2015066564 | 5/2015 |

OTHER PUBLICATIONS

European Search Report for EP 08830503 dated Jul. 12, 2011.
European Search Report for EP 10751519 dated Dec. 6, 2012.
European Search Report for EP 14182060 dated May 4, 2015.
European Search Report for EP 18194795 dated Dec. 17, 2018.
Hofmann et al., Oncology Rpt, 2006, 16:587-595.
Huang et al., Can Res, 55:3847-3853, (Sep. 2005).
International Search Report and the Written Opinion for PCT/US08/75953 dated Nov. 19, 2008.
International Search Report for PCT/US08/76049 dated Dec. 11, 2008.
International Search Report and Written Opinion from PCT/US10/027243 dated Jan. 7, 2011.
Iizasa, Clin Can Res, 1999, 5(1):149-153.
Izuhara et al., Curr Med Chem, 2006, 13:2291-2298.
JP 2011-554259 Office Action dated Jan. 7, 2014 (English Trans Only).
JP 2011-554259 Office Action dated Feb. 2, 2015 (w/Engish Trans).
KR1020187026414 Office Action dated Nov. 12, 2018 (w/English Trans).
Kasayama et al., The Allergy in Practice, 2005, 335:757-759.
Kikuchi, J Juzen Med Soc, 1998, 107(6): 434-445.
Kips, Eur Resp J, 2001, 18(supp 34): 24s-33s.
Koizumi et al., Clin Exp Immun, 1995, 101:468-473.
Koomen et al., Rapid Comm Mass Spectrometry, 2004, 18(21): 2537-2548.
Leonardi et al., Clin Experimental Allergy, 2007, 37(6):872-879.
Liu et al., Clin Chem, 2005, 51(7):1102-1109.
Ma et al., Biochem Biophys Res Comm, 2008, 371(3):425-430.
Mandrekar et al., J. Biopharm Stat, 2009, 19:530-542.
Moller et al., J Hepatology, 2007, 47:671-676.
Obase et al., Med Frontline, 2006, 61(3):85-490.
Oh et al., Proteomics, 2001, 1(10):1303-1319.
Oh et al., Am J Resp Cell Mol Bio, 2008, 40:568-574.
Okano et al., Proteomics, 2006, 6(13):3938-3948.
Ondo et al., J Jap Respir Soc, 2000, 14(3): 400 [P-070].
Orditura et al., J Interferon & Cytokine Res, 2002, 22:1129-1135.
Oyama et al., ; Anticancer Res, 2005, 25:1193-1196.
Paik; Curr Opin Obstet Gynecol, 2006, 18:59-63.
Saji et al., Biotherapy, 2002, 16(6):535-540 (English Abstract only).
SEQ ID No. 12 GenBank BLAST Results, Mar. 21, 2017.
Shi et al., ACTA Academiae Medicinenae Suzhou, 2001, 21(2):149-151.
Siegfried et al., Soc Thoracic Surg, 1998, 66:1915-1918.
Snell et al., Curr Opin Pharm, 2008, 8:222-235.
Voorzanger-Rousselot et al., Can Treatmt Rev, 2007, 33(3):230-283.
Wagner et al., Proteomics, 2003, 3(9):1692-1698.
Wills-Karp et al., Pulm Med, 2003, 9:21-27.
Wu et al., J Hygiene Res, 2000, 29(4):213-215.
Yanagisawa et al., Lancet, 2003, 362:433-439.
Yanagisawa et al., J Natl Can Instit, 2007, 99(11): 858-867.
Yeo et al., Proteomics, 2004, 4(11): 3308-3317.
Yoshikawa et al., Jap J Rhinology, 2007, 46(3):237.
Zhang et al., Prac Prev Med, 2007, 14(3):891-893.
Zhou et al., Chin J Lab Diag, 2007, 11(12):1628-1631.
Armah, et al., "Cerebrospinal Fluid and Serum Biomarkers of Cerebral Malaria Mortality in Ghanaian Children," Malaria Journal, vol. 6, 2007, pp. 1-17.
Boeri et al. (2011) PNAS, vol. 108, No. 9, pp. 3717-3718.
Bosse at al., Am J Respir and Crit Care Med, 1999, vol. 159, pp. 596-602.
Camilla et al., Clin Diag Lab Immun, 2001, vol. 8, pp. 776-784.
Chiu et al., Am J Resp Cell Mol Bio, 2003, vol. 29, pp. 106-116.
Chung et al., Thorx, 1999. vol. 54, pp. 825-857.
Cohen et al., Am J Phys, 2006, vol. 290, No. 6, pp. L1097-L1103.
Dai et al., Sci Chin Series C: Life Sci, 2007, vol. 50, No. 3, pp. 305-311.
Dass et al., International Conference on Control, Instrum., Energy & Commerce (CIEC) IEEE (2014) pp. 558-562.
Diaz-Urizrte et al., BMC Cioinformatics (2006) vol. 7, p. 3.
Eboshida et al., The 2007 Fiscal Year General Report and Report to Allotted Studies (2008) pp. 48-51.
Generat BLAST Results, SEQ. ID No. 12. Mar. 21, 2017.
Hofmann et al., Oncology Report (2006) vol. 16, pp. 587-595.
Huang et al., Can Res (Sep. 2005) vol. 65, pp. 3847-3853.
Iizasa, Clin Can Res, 1999, vol. 5, No. 1, pp. 149-153.
Izbicka et al. (2012) Cancer Genomics & Proteomics, vol. 9. pp. 27-36.
Izuhara et al., Curr Med Chem. 2006, vol. 13, pp. 2291-2298.
Kasayama et al., The Allergy in Practice, 2005, vol. 335, pp. 757-759.
Kikuchi, J Juzen Med Soc. 1998. vol. 107, No. 6, pp. 434-445.
Kips, Eur Resp J, 2001, vol. 18, Supplemental 34, p. 24s-33s.
Koizumi et al., Clin Exp Immun, 1995, vol. 101, pp. 468-473.
Koomeri et al., Rapid Comm Mass Spectrometry. 2004, vol. 18, No. 21, pp. 2537-2548.
Lee et al., General Thoracic Surgery (2012) vol. 143. pp. 421-427.
Leonardi et al., Clin Experimental Allergy, 2007, vol. 37, No. 6, pp. 872-879.
Liu et al., Clin Chem. 2005, vol. 51, No. 7, pp. 1102-1109.
Ma et al., Biochem Biophys Res Comm, 2008, vol. 371, No. 3, pp. 425-430.
Ma et al., Oncotarget (2017) vol. 8 pp. 18901-18913, published Jan. 21, 2017.
Mandrekar et al., J. Biopharm Stat, 2009, vol. 19, pp. 530-542.
Mattos et al., Chest, 2002, vol. 122, pp. 1543-1552.
Moller et al., J Hepatology, 2007, vol. 47, pp. 671-676.

(56) References Cited

OTHER PUBLICATIONS

Obase et al., Med Frontline, 2006, vol. 61, No. 3, pp. 85-490.
Oh at al., Proteomics, 2001. vol. 1, No. 10, pp. 1303-1319.
Oh et al., Am J Resp Cell Mol Bio, 2008, vol. 40, pp. 568-574.
Okano et al., Proteomics, 2006, vol. 6, No. 13, pp. 3938-3948.
Orditura et al., J Interferon & Cytokine Res, 2002, vol. 22, pp. 1129-1135.
Oshita et al., Oncol Rep, 2010, vol. 24, pp. 637-645.
Oyama et al., Anticancer Res. 2005, vol. 25, pp. 1193-1196.
Paik, Curr Opin Obstet Gynecol. 2006. vol. 18, pp. 59-63.
Pan et al., Lung, 2008, vol. 186, pp. 255-261.
Patnaik et al., Cancer Research, 2010, vol. 70, No. 1, pp. 36-45.
Saji et al., Biotherapy, 2002, vol. 16. No. 6, pp. 535-540.
Schapire, The Strength of Weak Learnability, Machine Learning. 1990, vol. 5, pp. 197-227.
Shi et al., ACTA Academiae Medicinenea Suzhou. 2001, vol. 21, No. 2, pp. 149-151.
Siegfried et al., Soc Thoracic Surg. 1998. vol. 66, pp. 1915-1918.
Snell et al., Curr Opin Pharm. 2008, vol. 8, pp. 222-235.
Tan et al., Ensemble machine learning on gene expression data for cancer classification, 2003, Applied Bioinformatics, vol. 2, Supplemental 3, S75-S83.
Voorzanger-Rousselot et al., Can Treatment Rev. 2007, vol. 33, No. 3, pp. 230-283.
Wagner et al., Proteomics, 2003, vol. 3, No. 9, pp. 1692-1698.
Wang, Chinese Doctoral Dissertations Full-text Database Information Science and Technology. vol. 8, pp. 1140-1224.
Wills-Karp et al., Pulm Med, 2003, vol. 9, pp. 21-27.
Wu et al., J Hygiene Res. 2000, vol. 29, No. 4, pp. 213-215.
Xia Xuewel et al., Chin J Lab Diego., 2005, vol. 9, No. 3, pp. 424-426.
Yanagisawa et al., Lancet. 2003, vol. 362, pp. 433-439.
Yanagisawa et al., J Nat' Can Instit, 2007, vol. 99, No. 11, pp. 858-867.
Yang et al., Med. Oncol., 2008, vol. 25, No. 4, pp. 380-386.
Yeo et al., Proteomics, 2004, vol. 4, No. 11, pp. 3308-3317.
Yoshikawa et al., Jap J Rhinology, 2007, vol. 46, No. 3, pp. 237.
Zhang et al., Prac Prev Med. 2007, vol. 14, No. 3, pp. 891-893.
Zhou et al., Chin J Lab Diag., 2007, vol. 11, No. 12, pp. 1628-1631.

\* cited by examiner

| FLOURESCENCE INTENSITY LEVEL IN THE NORMAL POPULATION |||||||
|---|---|---|---|---|---|---|---|
| Biomarker | Ave | S.D. | R.S.D. | Biomarker | Ave | S.D. | R.S.D. |
| sE-Selectin | -3754.00 | 35.15 | -0.94 | MMP-3 | 15660.06 | 5918.30 | 37.79 |
| EGF | 5015.80 | 4447.17 | 88.66 | IP-10 | 3408.61 | 4279.11 | 125.54 |
| IL-5 | -293.76 | 1201.87 | -409.13 | IL-10 | 401.93 | 816.03 | 203.03 |
| PAI-1 (total) | 4650.05 | 1273.31 | 27.38 | MMP-8 | 2673.57 | 1392.34 | 52.08 |
| Resistin | 3138.02 | 2234.38 | 71.20 | MMP-2 | 24052.74 | 928.10 | 3.86 |
| Leptin | 8089.08 | 9137.49 | 112.96 | G-CSF | -17.85 | 1164.65 | -6525.86 |
| sVCAM-1 | 1017.74 | 609.37 | 59.87 | sFasL | 59.40 | 29.11 | 49.00 |
| MMP-13 | 0.30 | 6.35 | 2141.82 | IL-8 | 7726.40 | 6653.62 | 86.12 |
| SAA | 1541.92 | 4224.24 | 273.96 | TGF-ALPHA | 2521.01 | 2820.52 | 111.88 |
| sICAM-1 | -3488.15 | 1784.70 | -51.16 | IFN-gamma | 347.30 | 1150.62 | 331.31 |
| CD40 Ligand | 161.20 | 192.05 | 119.14 | MPO | 1960.51 | 4609.11 | 235.10 |
| IL-7 | -553.29 | 2222.61 | -401.71 | MIP-1alpha | 2579.96 | 3201.87 | 124.11 |
| C-Peptide | 8734.89 | 8388.22 | 96.03 | IL-1ra | 828.88 | 1771.02 | 213.66 |
| HGF | 650.01 | 413.44 | 63.61 | VEGF | 4791.40 | 5321.58 | 111.07 |
| CRP | 10243.98 | 8699.54 | 84.92 | IL-13 | 664.75 | 2013.87 | 302.95 |
| IL-1alpha | 6574.13 | 9870.69 | 150.14 | Insulin | 1485.90 | 3380.72 | 227.52 |
| MMP-7 | 309.12 | 88.76 | 28.71 | IL-12(p70) | 1174.46 | 4080.10 | 347.40 |
| IL-4 | 2261.07 | 2731.85 | 120.82 | IL-1B | 778.53 | 2976.43 | 382.32 |
| Adiponectin | 24525.83 | 1290.90 | 5.26 | GLP-1(Active) | 708.76 | 2492.64 | 351.69 |
| MMP-9 | 28540.58 | 803.64 | 2.82 | FRACTALKINE | 916.75 | 2024.48 | 220.83 |
| GM-CSF | 103.94 | 973.06 | 936.21 | IL-2 | 534.85 | 1262.10 | 235.97 |
| MMP-12 | -2.29 | 2.48 | -108.31 | EOTAXIN | 6342.86 | 6613.72 | 104.27 |
| IL-15 | 231.98 | 679.37 | 292.85 | MIP-1beta | 1513.50 | 3551.71 | 234.67 |
| IL-17 | 1680.73 | 4225.28 | 251.40 | sFas | 181.43 | 63.29 | 34.88 |
| IL-12(p40), free | 171.55 | 1091.36 | 636.16 | Amylin (Active) | 1447.02 | 4589.31 | 317.16 |
| MIF | 97.55 | 71.64 | 73.44 | MMP-1 | 6010.22 | 4006.18 | 66.66 |
| TNF-alpha | 1185.89 | 3586.20 | 302.41 | Glucagon | 1869.83 | 4635.13 | 247.89 |
| I-TAC | 19.16 | 34.72 | 181.17 | MCP-1 | 27869.05 | 965.91 | 3.47 |
| IL-6 | 3557.94 | 5666.10 | 159.25 | SAP | 24732.42 | 803.37 | 3.25 |

FIG. 1A

| FLOURESCENCE INTENSITY LEVEL IN THE LUNG CANCER POPULATION ||||||||
|---|---|---|---|---|---|---|---|
| Biomarker | Ave | S.D. | R.S.D. | Biomarker | Ave | S.D. | R.S.D. |
| sE-Selectin | -3710.76 | 26.27 | -0.71 | MMP-3 | 15470.68 | 5795.86 | 37.46 |
| EGF | 12471.39 | 9397.19 | 75.35 | IP-10 | 5641.16 | 6148.52 | 108.99 |
| IL-5 | -947.96 | 859.85 | -90.70 | IL-10 | 1053.38 | 2430.64 | 230.75 |
| PAI-1 (total) | 3776.85 | 1098.08 | 29.07 | MMP-8 | 2845.20 | 1305.16 | 45.87 |
| Resistin | 2084.83 | 853.26 | 40.93 | MMP-2 | 23768.35 | 1272.05 | 5.35 |
| Leptin | 24.05 | 8538.62 | 35503.61 | G-CSF | -209.22 | 896.64 | -428.57 |
| sVCAM-1 | 1364.62 | 912.59 | 66.88 | sFasL | 487.48 | 2434.79 | 499.46 |
| MMP-13 | -1.10 | 3.81 | -345.47 | IL-8 | 7258.97 | 8912.30 | 122.78 |
| SAA | 7712.92 | 10706.73 | 138.82 | TGF-ALPHA | 1859.04 | 4739.54 | 254.95 |
| sICAM-1 | -2484.13 | 3305.66 | -133.07 | IFN-gamma | 248.91 | 1141.12 | 458.45 |
| CD40 Ligand | 539.63 | 495.14 | 91.76 | MPO | 2899.33 | 5179.23 | 178.64 |
| IL-7 | -1723.03 | 869.90 | -50.49 | MIP-1alpha | 4869.60 | 7669.88 | 157.51 |
| C-Peptide | 10380.92 | 8201.68 | 79.01 | IL-1ra | 298.27 | 535.27 | 179.46 |
| HGF | 560.93 | 421.36 | 75.12 | VEGF | 7222.50 | 6074.27 | 84.10 |
| CRP | 20810.52 | 6683.21 | 32.11 | IL-13 | 373.67 | 713.36 | 190.90 |
| IL-1alpha | 404.89 | 5992.97 | 1480.15 | Insulin | 1758.20 | 3177.46 | 180.72 |
| MMP-7 | 583.63 | 674.48 | 115.57 | IL-12(p70) | 208.66 | 701.87 | 336.37 |
| IL-4 | 422.10 | 1652.03 | 391.38 | IL-1B | 1278.97 | 3946.61 | 308.58 |
| Adiponectin | 24462.63 | 1616.93 | 6.61 | GLP-1(Active) | 229.15 | 437.88 | 191.09 |
| MMP-9 | 27269.90 | 1233.41 | 4.52 | FRACTALKINE | 279.20 | 747.82 | 267.85 |
| GM-CSF | -188.48 | 771.98 | -409.58 | IL-2 | 178.31 | 421.41 | 236.34 |
| MMP-12 | -0.65 | 2.25 | -345.94 | EOTAXIN | 6982.76 | 6113.93 | 87.56 |
| IL-15 | 19.63 | 139.23 | 709.13 | MIP-1beta | 924.40 | 2438.49 | 263.79 |
| IL-17 | 265.67 | 812.81 | 305.94 | sFas | 214.14 | 140.95 | 65.82 |
| IL-12(p40), free | -115.91 | 847.03 | -730.77 | Amylin (Active) | 889.30 | 1721.49 | 193.58 |
| MIF | 331.60 | 1019.01 | 307.30 | MMP-1 | 7517.19 | 6016.10 | 80.03 |
| TNF-alpha | 379.20 | 644.19 | 169.88 | Glucagon | 2319.96 | 3302.68 | 142.36 |
| I-TAC | 7.90 | 24.12 | 305.44 | MCP-1 | 27622.58 | 1394.00 | 5.05 |
| IL-6 | 1581.59 | 3261.99 | 206.25 | SAP | 24537.83 | 742.40 | 3.03 |

FIG. 1B

| FLOURESCENCE INTENSITY LEVEL IN THE ASTHMA POPULATION ||||||||
|---|---|---|---|---|---|---|---|
| Biomarker | Ave | S.D. | R.S.D. | Biomarker | Ave | S.D. | R.S.D. |
| sE-Selectin | 106.77 | 49.48 | 46.35 | MMP-3 | 12561.00 | 6374.02 | 50.74 |
| EGF | 1891.44 | 2231.32 | 117.97 | IP-10 | 2936.55 | 4067.24 | 138.50 |
| IL-5 | 1652.42 | 2751.18 | 166.49 | IL-10 | 230.17 | 601.55 | 261.35 |
| PAI-1 (total) | -2816.18 | 1591.94 | -56.53 | MMP-8 | 2134.40 | 1521.23 | 71.27 |
| Resistin | 1113.54 | 1337.70 | 120.13 | MMP-2 | 24772.42 | 2488.88 | 10.05 |
| Leptin | 17523.57 | 8823.12 | 50.35 | G-CSF | 164.26 | 1467.85 | 893.59 |
| sVCAM-1 | 3784.43 | 856.94 | 22.64 | sFasL | 49.41 | 80.27 | 162.46 |
| MMP-13 | 3.94 | 4.58 | 116.10 | IL-8 | 5297.59 | 6465.20 | 122.04 |
| SAA | 1415.16 | 1503.12 | 106.22 | TGF-ALPHA | 3565.40 | 4963.06 | 139.20 |
| sICAM-1 | 5039.72 | 2494.41 | 49.49 | IFN-gamma | 66.13 | 170.57 | 257.94 |
| CD40 Ligand | 703.27 | 459.33 | 65.31 | MPO | 2477.35 | 3110.70 | 125.57 |
| IL-7 | -634.33 | 1674.74 | -264.02 | MIP-1alpha | 3104.09 | 3288.61 | 105.94 |
| C-Peptide | 21354.00 | 5055.31 | 23.67 | IL-1ra | 573.51 | 893.00 | 155.71 |
| HGF | 904.47 | 455.18 | 50.33 | VEGF | 5570.03 | 4663.60 | 83.73 |
| CRP | 12052.08 | 8985.63 | 74.56 | IL-13 | 541.10 | 816.76 | 150.94 |
| IL-1alpha | 5722.73 | 9910.91 | 173.19 | Insulin | 2948.06 | 4584.49 | 155.51 |
| MMP-7 | 385.99 | 137.37 | 35.59 | IL-12(p70) | 444.58 | 651.36 | 146.51 |
| IL-4 | 2366.17 | 4127.72 | 174.45 | IL-1B | 166.73 | 367.22 | 220.25 |
| Adiponectin | 21241.91 | 3183.07 | 14.98 | GLP-1(Active) | 273.07 | 539.24 | 197.47 |
| MMP-9 | 28559.72 | 916.63 | 3.21 | FRACTALKINE | 318.34 | 752.30 | 236.32 |
| GM-CSF | 574.11 | 1081.15 | 188.32 | IL-2 | 386.20 | 561.42 | 145.37 |
| MMP-12 | -0.88 | 3.26 | -372.85 | EOTAXIN | 6985.59 | 4047.59 | 57.94 |
| IL-15 | 193.73 | 294.67 | 152.10 | MIP-1beta | 550.53 | 1038.97 | 188.72 |
| IL-17 | 1267.20 | 2096.39 | 165.44 | sFas | 238.89 | 184.67 | 77.30 |
| IL-12(p40), free | 361.39 | 899.35 | 248.86 | Amylin (Active) | 995.40 | 2621.90 | 263.40 |
| MIF | 143.50 | 79.27 | 55.24 | MMP-1 | 6968.82 | 5642.31 | 80.97 |
| TNF-alpha | 917.00 | 878.85 | 95.84 | Glucagon | 1598.53 | 3655.30 | 228.67 |
| I-TAC | 20.77 | 12.07 | 58.12 | MCP-1 | 27601.89 | 2359.19 | 8.55 |
| IL-6 | 4559.95 | 6199.94 | 135.97 | SAP | 24394.42 | 1810.34 | 7.42 |

FIG. 1C

| PERCENT CHANGE IN MEAN FLOURESCENCE INTENSITY | | | | | | |
|---|---|---|---|---|---|---|
| Biomarker | LC vs NO | AST vs NO | LC vs AST | Biomarker | LC vs NO | AST vs NO | LC vs AST |
| sE-Selectin | -1.15 | -102.84 | -3600.09 | MMP-3 | -1.21 | -19.79 | -51.45 |
| EGF | 148.64 | -62.29 | 1255.02 | IP-10 | 65.50 | -13.85 | 709.83 |
| IL-5 | 222.70 | -662.50 | -104.99 | IL-10 | 162.08 | -42.73 | -10.72 |
| PAI-1 (total) | -18.78 | -160.56 | -222.72 | MMP-8 | 6.42 | -20.17 | 122.89 |
| Resistin | -33.56 | -64.51 | 186.59 | MMP-2 | -1.18 | 2.99 | -7.54 |
| Leptin | -99.70 | 116.63 | -129.48 | G-CSF | 1072.30 | -1020.42 | 293.76 |
| sVCAM-1 | 34.08 | 271.85 | -65.45 | sFasL | 720.72 | -16.82 | -14.38 |
| MMP-13 | -471.91 | 1229.05 | -8.70 | IL-8 | -6.05 | -31.44 | 339.52 |
| SAA | 400.22 | -8.22 | 524.17 | TGF-ALPHA | -26.26 | 41.43 | 300.77 |
| sICAM-1 | -28.78 | -244.48 | -215.09 | IFN-gamma | -28.33 | -80.96 | 232.69 |
| CD40 Ligand | 234.76 | 336.27 | -60.21 | MPO | 47.89 | 26.36 | -218.24 |
| IL-7 | 211.41 | 14.65 | 70.89 | MIP-1alpha | 88.75 | 20.32 | 147.13 |
| C-Peptide | 18.84 | 144.47 | -58.39 | IL-1ra | -64.02 | -30.81 | 137.89 |
| HGF | -13.70 | 39.15 | -129.39 | VEGF | 50.74 | 16.25 | 115.00 |
| CRP | 103.15 | 17.65 | 117.23 | IL-13 | -43.79 | -18.60 | -101.85 |
| IL-1alpha | -93.84 | -12.95 | -27.14 | Insulin | 18.33 | 98.40 | -82.50 |
| MMP-7 | 88.80 | 24.87 | -27.90 | IL-12(p70) | -82.23 | -62.15 | -46.85 |
| IL-4 | -81.33 | 4.65 | -65.13 | IL-1B | 64.28 | -78.58 | 10.66 |
| Adiponectin | -0.26 | -13.39 | 12.60 | GLP-1(Active) | -67.67 | -61.47 | 70.47 |
| MMP-9 | -4.45 | 0.07 | -3.87 | FRACTALKINE | -69.54 | -65.28 | -43.21 |
| GM-CSF | -281.34 | 452.37 | -140.55 | IL-2 | -66.66 | -27.79 | 14.84 |
| MMP-12 | -71.66 | -61.85 | -100.00 | EOTAXIN | 10.09 | 10.13 | 64.76 |
| IL-15 | -91.54 | -16.49 | -8.38 | MIP-1beta | -38.92 | -63.63 | 7.17 |
| IL-17 | -84.19 | -24.60 | -94.81 | sFas | 18.03 | 31.67 | -54.25 |
| IL-12(p40), free | -167.56 | 110.66 | -297.38 | Amylin (Active) | -38.54 | -31.21 | 18.55 |
| MIF | 239.94 | 47.11 | 267.31 | MMP-1 | 25.07 | 15.95 | -23.61 |
| TNF-alpha | -68.02 | -22.67 | -7.11 | Glucagon | 24.07 | -14.51 | -24.79 |
| I-TAC | -58.79 | 8.37 | -38.37 | MCP-1 | -0.88 | -0.96 | -0.24 |
| IL-6 | -55.55 | 28.16 | -54.85 | SAP | -0.79 | -1.37 | -2.51 |

FIG. 1D

| SIGNIFIGANCE OF POPULATION DIFFERENCES EXPRESSED AS PROBABILITY OF STUDENT'S T VALUE ||||||||
|---|---|---|---|---|---|---|---|
| Biomarker | LC vs NO | AST vs NO | LC vs AST | Biomarker | LC vs NO | AST vs NO | LC vs AST |
| sE-Selectin | 0.000 | 0.000 | 0.000 | MMP-3 | 0.901 | 0.060 | 0.074 |
| EGF | 0.000 | 0.001 | 0.000 | IP-10 | 0.108 | 0.669 | 0.055 |
| IL-5 | 0.018 | 0.001 | 0.000 | IL-10 | 0.169 | 0.368 | 0.087 |
| PAI-1 (total) | 0.006 | 0.000 | 0.000 | MMP-8 | 0.624 | 0.164 | 0.061 |
| Resistin | 0.019 | 0.000 | 0.002 | MMP-2 | 0.327 | 0.145 | 0.056 |
| Leptin | 0.001 | 0.000 | 0.000 | G-CSF | 0.479 | 0.602 | 0.244 |
| sVCAM-1 | 0.089 | 0.000 | 0.000 | sFasL | 0.340 | 0.526 | 0.346 |
| MMP-13 | 0.305 | 0.016 | 0.000 | IL-8 | 0.819 | 0.165 | 0.344 |
| SAA | 0.005 | 0.881 | 0.003 | TGF-ALPHA | 0.514 | 0.325 | 0.186 |
| sICAM-1 | 0.149 | 0.000 | 0.000 | IFN-gamma | 0.741 | 0.206 | 0.405 |
| CD40 Ligand | 0.000 | 0.000 | 0.198 | MPO | 0.461 | 0.621 | 0.711 |
| IL-7 | 0.009 | 0.877 | 0.003 | MIP-1alpha | 0.137 | 0.541 | 0.265 |
| C-Peptide | 0.467 | 0.000 | 0.000 | IL-1ra | 0.122 | 0.496 | 0.157 |
| HGF | 0.412 | 0.030 | 0.004 | VEGF | 0.105 | 0.557 | 0.253 |
| CRP | 0.000 | 0.440 | 0.000 | IL-13 | 0.459 | 0.764 | 0.408 |
| IL-1alpha | 0.005 | 0.744 | 0.016 | Insulin | 0.761 | 0.170 | 0.283 |
| MMP-7 | 0.031 | 0.014 | 0.134 | IL-12(p70) | 0.206 | 0.354 | 0.191 |
| IL-4 | 0.003 | 0.909 | 0.021 | IL-1B | 0.581 | 0.285 | 0.143 |
| Adiponectin | 0.868 | 0.000 | 0.000 | GLP-1(Active) | 0.357 | 0.369 | 0.751 |
| MMP-9 | 0.000 | 0.933 | 0.000 | FRACTALKINE | 0.111 | 0.147 | 0.843 |
| GM-CSF | 0.202 | 0.087 | 0.003 | IL-2 | 0.148 | 0.569 | 0.115 |
| MMP-12 | 0.009 | 0.067 | 0.760 | EOTAXIN | 0.699 | 0.660 | 0.998 |
| IL-15 | 0.099 | 0.785 | 0.005 | MIP-1beta | 0.457 | 0.173 | 0.456 |
| IL-17 | 0.077 | 0.642 | 0.018 | sFas | 0.251 | 0.114 | 0.567 |
| IL-12(p40), free | 0.259 | 0.475 | 0.042 | Amylin (Active) | 0.575 | 0.650 | 0.866 |
| MIF | 0.215 | 0.024 | 0.335 | MMP-1 | 0.258 | 0.456 | 0.722 |
| TNF-alpha | 0.230 | 0.701 | 0.010 | Glucagon | 0.690 | 0.806 | 0.462 |
| I-TAC | 0.150 | 0.818 | 0.014 | MCP-1 | 0.429 | 0.570 | 0.967 |
| IL-6 | 0.103 | 0.523 | 0.025 | SAP | 0.334 | 0.357 | 0.691 |

FIG. 1E

| FLUORESCENCE INTENSITY LEVEL IN THE NORMAL POPULATION | | | |
|---|---|---|---|
| Biomarker | Ave | S.D. | R.S.D. |
| Adiponectin | 2339.70 | 1601.88 | 68.46 |
| Resistin | 114.63 | 91.26 | 79.61 |
| PAI-1 | 366.00 | 424.13 | 115.88 |
| SE-selectin | 63.11 | 49.58 | 78.55 |
| sVCAM-1 | 1634.10 | 408.80 | 25.02 |
| sICAM-1 | 3541.68 | 1752.76 | 49.49 |
| MPO | 717.62 | 1645.83 | 229.35 |
| CRP | 8839.73 | 6391.84 | 72.31 |
| SAA | 1970.35 | 3668.84 | 186.20 |
| SAP | 2160.88 | 597.89 | 27.67 |
| Leptin | 2638.03 | 3025.87 | 114.70 |
| GLP-1 | 57.77 | 100.58 | 174.10 |
| Amylin (Total) | 120.65 | 256.04 | 212.21 |
| C-Peptide | 5015.95 | 2022.03 | 40.31 |
| Insulin | 322.77 | 436.71 | 135.30 |
| Sfas | 49.72 | 183.17 | 368.37 |
| sFSI | 13.17 | 12.32 | 93.54 |
| MIF | 61.95 | 113.33 | 182.95 |
| IL-1β | 23.50 | 11.80 | 50.24 |
| IL-2 | 13.13 | 55.39 | 421.85 |
| IL-1ra | 22.32 | 24.11 | 108.02 |
| IL-4 | 112.05 | 66.15 | 59.03 |
| IL-5 | 17.40 | 19.03 | 109.38 |
| IL-6 | 36.69 | 50.08 | 136.52 |
| IL-7 | 14.32 | 5.44 | 37.95 |
| TGF-α | 32.10 | 8.07 | 25.13 |
| Fractalkine | 12.69 | 3.15 | 24.80 |
| IL-8 | 280.43 | 703.76 | 250.96 |
| IL-10 | 12.55 | 3.87 | 30.82 |
| IL-15 | 24.21 | 4.43 | 18.28 |
| IL-17 | 36.44 | 13.75 | 37.74 |
| IL-1α | 83.74 | 148.45 | 177.27 |
| IFN-γ | 21.75 | 5.92 | 27.23 |
| G-CSF | 23.75 | 4.58 | 19.27 |
| GM-CSF | 27.98 | 14.45 | 51.65 |
| TFN-α | 39.67 | 17.41 | 43.88 |
| MCP-1 | 49.72 | 34.31 | 69.02 |
| IL-12 (p40), free | 24.17 | 7.86 | 32.54 |
| MIP-1α | 39.78 | 27.14 | 68.22 |
| MIP-1β | 20.27 | 9.77 | 48.19 |
| VEGF | 41.55 | 13.17 | 31.71 |

FIG. 2A

| FLUORESCENCE INTENSITY LEVEL IN THE LUNG CANCER POPULATION | | | |
|---|---|---|---|
| Biomarker | Ave | S.D. | R.S.D. |
| Adiponectin | 2534.09 | 1827.31 | 72.11 |
| Resistin | 149.61 | 142.26 | 95.09 |
| PAI-1 | 629.60 | 307.11 | 48.78 |
| SE-selectin | 36.61 | 58.58 | 160.04 |
| sVCAM-1 | 1599.09 | 586.93 | 36.70 |
| sICAM-1 | 3079.69 | 1067.64 | 52.20 |
| MPO | 3000.57 | 2145.32 | 71.50 |
| CRP | 12563.08 | 6483.62 | 51.61 |
| SAA | 7173.28 | 7659.62 | 106.78 |
| SAP | 1161.51 | 897.26 | 77.25 |
| Leptin | 802.52 | 1210.97 | 150.90 |
| GLP-1 | 135.12 | 727.35 | 538.29 |
| Amylin (Total) | 301.16 | 1096.20 | 363.99 |
| C-Peptide | 2820.47 | 1931.78 | 68.49 |
| Insulin | 231.23 | 704.98 | 304.88 |
| Sfas | 42.69 | 32.34 | 75.77 |
| sFSI | 8.88 | 5.26 | 59.19 |
| MIF | 126.13 | 225.30 | 178.62 |
| IL-1β | 25.60 | 3.06 | 11.94 |
| IL-2 | 9.61 | 3.44 | 35.78 |
| IL-1ra | 26.67 | 6.50 | 24.39 |
| IL-4 | 90.91 | 45.70 | 50.27 |
| IL-5 | 14.17 | 4.90 | 34.60 |
| IL-6 | 56.88 | 201.09 | 353.57 |
| IL-7 | 27.30 | 115.37 | 422.52 |
| TGF-α | 32.23 | 8.82 | 27.38 |
| Fractalkine | 13.29 | 3.05 | 22.97 |
| IL-8 | 98.68 | 120.57 | 122.19 |
| IL-10 | 22.46 | 74.90 | 333.47 |
| IL-15 | 24.30 | 2.82 | 11.61 |
| IL-17 | 50.64 | 39.88 | 78.76 |
| IL-1α | 48.51 | 23.72 | 48.91 |
| IFN-γ | 23.99 | 6.93 | 28.87 |
| G-CSF | 24.96 | 16.23 | 65.03 |
| GM-CSF | 28.98 | 3.60 | 12.43 |
| TFN-α | 90.78 | 565.51 | 622.96 |
| MCP-1 | 149.53 | 230.71 | 154.29 |
| IL-12 (p40), free | 21.72 | 8.15 | 37.51 |
| MIP-1α | 63.94 | 150.25 | 235.00 |
| MIP-1β | 38.30 | 127.37 | 332.54 |
| VEGF | 40.73 | 22.15 | 54.38 |

FIG. 2B

| FLUORESCENCE INTENSITY LEVEL IN THE LUNG CANCER POPULATION | | | |
|---|---|---|---|
| Biomarker | Ave | S.D. | R.S.D. |
| Adiponectin | 3035.92 | 2008.84 | 66.17 |
| Resistin | 265.24 | 189.24 | 71.35 |
| PAI-1 | 788.76 | 267.12 | 33.87 |
| SE-selectin | 38.80 | 30.29 | 78.07 |
| sVCAM-1 | 2988.12 | 948.06 | 31.73 |
| sICAM-1 | 3466.48 | 1326.54 | 38.27 |
| MPO | 4005.47 | 2572.12 | 64.22 |
| CRP | 10609.85 | 6186.73 | 58.31 |
| SAA | 3862.88 | 4256.70 | 110.19 |
| SAP | 2558.42 | 654.11 | 25.57 |
| Leptin | 2901.26 | 3238.21 | 111.61 |
| GLP-1 | 133.45 | 627.72 | 470.36 |
| Amylin (Total) | 347.48 | 1257.27 | 361.82 |
| C-Peptide | 5798.84 | 2767.02 | 47.72 |
| Insulin | 493.28 | 1468.20 | 297.64 |
| Sfas | 82.05 | 41.68 | 50.80 |
| sFSI | 33.56 | 50.68 | 151.01 |
| MIF | 69.89 | 48.66 | 69.62 |
| IL-1β | 41.58 | 151.82 | 365.11 |
| IL-2 | 12.75 | 3.63 | 28.46 |
| IL-1ra | 27.03 | 5.07 | 18.78 |
| IL-4 | 216.14 | 368.04 | 170.28 |
| IL-5 | 42.86 | 89.64 | 209.14 |
| IL-6 | 174.63 | 694.85 | 397.90 |
| IL-7 | 28.25 | 15.68 | 55.53 |
| TGF-α | 43.24 | 13.20 | 30.54 |
| Fractalkine | 16.13 | 3.54 | 21.96 |
| IL-8 | 1123.79 | 2876.50 | 255.96 |
| IL-10 | 15.80 | 3.81 | 24.10 |
| IL-15 | 30.22 | 8.18 | 27.08 |
| IL-17 | 57.59 | 27.56 | 47.86 |
| IL-1α | 294.98 | 854.12 | 289.55 |
| IFN-γ | 26.60 | 5.96 | 22.40 |
| G-CSF | 32.29 | 14.01 | 43.40 |
| GM-CSF | 40.62 | 33.59 | 82.70 |
| TFN-α | 88.03 | 350.87 | 398.57 |
| MCP-1 | 555.77 | 2390.21 | 430.08 |
| IL-12 (p40), free | 29.45 | 8.77 | 29.77 |
| MIP-1α | 136.92 | 834.62 | 609.56 |
| MIP-1β | 30.17 | 41.55 | 137.72 |
| VEGF | 54.31 | 19.95 | 36.73 |

FIG. 2C

| PERCENT FLUORESCENCE CHANGE IN MEAN FLUORESCENCE | | | |
|---|---|---|---|
| Biomarker | LC vs. NO | AST vs. NO | AST vs. LC |
| Adiponectin | 8.308023 | 29.756609 | 16.5298599 |
| Resistin | 30.52113 | 131.39591 | 43.5940182 |
| PAI-1 | 72.02467 | 115.509824 | 20.1778046 |
| SE-selectin | -41.9987 | -38.524081 | 5.65196398 |
| sVCAM-1 | -2.14221 | 82.8602657 | 46.4849324 |
| sICAM-1 | -13.0445 | -2.1233592 | 11.1580584 |
| MPO | 318.1283 | 458.159543 | 25.0880246 |
| CRP | 42.12063 | 20.02461 | -18.409577 |
| SAA | 264.0607 | 96.0500618 | -85.697828 |
| SAP | -46.2484 | 18.3969983 | 54.6005061 |
| Leptin | -69.579 | 9.97796417 | 72.3390188 |
| GLP-1 | 133.9041 | 131.013935 | -1.2510585 |
| Amylin (Total) | 149.6069 | 188.001524 | 13.3314104 |
| C-Peptide | -43.77 | 15.6079318 | 51.3614645 |
| Insulin | -28.3602 | 52.8249719 | 53.1230023 |
| Sfas | -14.1487 | 65.0120998 | 47.972753 |
| sFSI | -32.5859 | 154.781105 | 73.5403963 |
| MIF | 103.6145 | 12.821492 | -80.474883 |
| IL-1β | 8.95437 | 76.9673003 | 38.4324848 |
| IL-2 | -26.8184 | -2.8675535 | 24.6579321 |
| IL-1ra | 19.49224 | 21.1124424 | 1.33776455 |
| IL-4 | -18.8655 | 92.8892423 | 57.9372345 |
| IL-5 | -18.5965 | 146.294659 | 66.9487515 |
| IL-6 | 55.02707 | 375.999006 | 67.4312203 |
| IL-7 | 90.62035 | 97.1867053 | 3.33001776 |
| TGF-α | 0.411397 | 34.7028941 | 25.4571344 |
| Fractalkine | 4.789211 | 27.1132799 | 17.5623423 |
| IL-8 | -64.8117 | 300.737772 | 91.2191083 |
| IL-10 | 79.03757 | 25.9054886 | -42.199971 |
| IL-15 | 0.349499 | 24.7932651 | 19.5874082 |
| IL-17 | 38.98752 | 58.0586958 | 12.0658817 |
| IL-1α | -42.0762 | 252.257187 | 83.5563807 |
| IFN-γ | 10.33321 | 22.3173905 | 9.79761046 |
| G-CSF | 5.06491 | 35.9358549 | 22.7099358 |
| GM-CSF | 3.606656 | 45.1976606 | 28.6444042 |
| TNF-α | 128.8153 | 121.889912 | -3.1211056 |
| MCP-1 | 200.7569 | 1017.85782 | 73.0952475 |
| IL-12 (p40), free | -10.1185 | 21.8436008 | 26.2320627 |
| MIP-1α | 60.73545 | 244.225273 | 53.3051572 |
| MIP-1β | 88.94775 | 48.82232 | -26.96197 |
| VEGF | -1.96318 | 30.7326781 | 25.0097033 |

FIG. 2D

| SIGNIFICANCE OF POPULATION DIFFERENCES EXPRESSED AS PROBABILITY OF STUDENT'S T VALUE | | | |
|---|---|---|---|
| Biomarker | T LC vs. NO | T AST vs. NO | T AST vs. LC |
| Adiponectin | 0.306 | 0.001 | 0.039 |
| Resistin | 0.007 | 0.000 | 0.000 |
| PAI-1 | 0.000 | 0.000 | 0.000 |
| SE-selectin | 0.000 | 0.000 | 0.723 |
| sVCAM-1 | 0.526 | 0.000 | 0.000 |
| sICAM-1 | 0.014 | 0.700 | 0.043 |
| MPO | 0.000 | 0.000 | 0.001 |
| CRP | 0.000 | 0.022 | 0.016 |
| SAA | 0.000 | 0.000 | 0.000 |
| SAP | 0.000 | 0.000 | 0.000 |
| Leptin | 0.000 | 0.486 | 0.000 |
| GLP-1 | 0.157 | 0.112 | 0.985 |
| Amylin (Total) | 0.032 | 0.019 | 0.755 |
| C-Peptide | 0.000 | 0.006 | 0.000 |
| Insulin | 0.151 | 0.145 | 0.061 |
| Sfas | 0.647 | 0.072 | 0.000 |
| sFSI | 0.000 | 0.000 | 0.000 |
| MIF | 0.001 | 0.490 | 0.011 |
| IL-1β | 0.037 | 0.111 | 0.204 |
| IL-2 | 0.444 | 0.944 | 0.000 |
| IL-1ra | 0.035 | 0.046 | 0.632 |
| IL-4 | 0.001 | 0.000 | 0.000 |
| IL-5 | 0.046 | 0.000 | 0.000 |
| IL-6 | 0.193 | 0.008 | 0.053 |
| IL-7 | 0.130 | 0.000 | 0.933 |
| TGF-α | 0.888 | 0.000 | 0.000 |
| Fractalkine | 0.079 | 0.000 | 0.000 |
| IL-8 | 0.002 | 0.000 | 0.000 |
| IL-10 | 0.075 | 0.000 | 0.357 |
| IL-15 | 0.841 | 0.000 | 0.000 |
| IL-17 | 0.000 | 0.000 | 0.121 |
| IL-1α | 0.005 | 0.001 | 0.001 |
| IFN-γ | 0.002 | 0.000 | 0.002 |
| G-CSF | 0.341 | 0.000 | 0.000 |
| GM-CSF | 0.411 | 0.000 | 0.000 |
| TNF-α | 0.224 | 0.064 | 0.965 |
| MCP-1 | 0.000 | 0.005 | 0.042 |
| IL-12 (p40), free | 0.006 | 0.000 | 0.000 |
| MIP-1α | 0.034 | 0.117 | 0.302 |
| MIP-1β | 0.058 | 0.002 | 0.524 |
| VEGF | 0.679 | 0.000 | 0.000 |

FIG. 2E

| FLUORESCENCE INTENSITY LEVEL IN THE NORMAL POPULATION ||||||||
|---|---|---|---|---|---|---|---|
| Biomarker | Average | S.D. | R.S.D. | Biomarker | Average | S.D. | R.S.D. |
| Adiponectin | 2259.55 | 1504.98 | 66.61 | IL-17 | 37.60 | 13.52 | 35.95 |
| Resistin | 124.37 | 90.22 | 72.55 | IL-1α | 95.36 | 185.32 | 194.33 |
| PAI-1[A] | 335.10 | 371.63 | 110.90 | IFN-γ | 23.30 | 9.28 | 39.81 |
| SE-selectin | 60.34 | 47.58 | 78.85 | G-CSF | 23.84 | 4.12 | 17.29 |
| sVCAM-1 | 1753.31 | 513.04 | 29.26 | GM-CSF | 28.60 | 12.57 | 43.94 |
| sICAM-1 | 3295.75 | 1574.35 | 47.77 | TNF-α | 43.52 | 15.71 | 36.10 |
| MPO | 592.73 | 1503.40 | 253.64 | MCP-1 | 46.39 | 29.47 | 63.51 |
| CRP | 8384.00 | 6292.94 | 75.06 | IL-12 (p40) | 24.93 | 7.26 | 29.11 |
| SAA | 2202.71 | 4017.36 | 182.38 | MIP-1α | 41.04 | 27.61 | 67.27 |
| SAP | 2200.71 | 570.75 | 25.93 | MIP-1β | 21.28 | 9.86 | 46.35 |
| Leptin[1] | 2204.67 | 2771.37 | 125.70 | VEGF | 40.80 | 11.45 | 28.07 |
| GLP-1 | 56.21 | 102.46 | 182.27 | IL12 (p70) | 7.66 | 36.69 | 479.00 |
| Amylin (Total) | 142.47 | 339.44 | 238.25 | IL-13 | 11.41 | 57.04 | 499.86 |
| C-Peptide | 4748.58 | 1971.09 | 41.51 | MMP-2 | 155.73 | 439.49 | 282.21 |
| Insulin | 278.12 | 424.50 | 152.63 | MMP-1 | 103.52 | 179.41 | 173.31 |
| Sfas | 58.81 | 148.38 | 252.31 | MMP-3 | 6668.81 | 2442.77 | 36.63 |
| sFSI | 15.13 | 16.89 | 111.59 | Eotaxin | 196.78 | 208.46 | 105.94 |
| MIF | 52.08 | 112.39 | 215.81 | Leptin[2] | 3767.80 | 3885.08 | 103.11 |
| IL-1β | 23.71 | 9.52 | 40.16 | IP-10 | 543.43 | 820.15 | 150.92 |
| IL-2 | 12.26 | 44.02 | 358.99 | MMP-9 | 1090.51 | 1599.16 | 146.64 |
| IL-1ra | 23.11 | 19.35 | 83.77 | MMP-13 | 9.95 | 35.67 | 358.67 |
| IL-4 | 114.39 | 72.33 | 63.23 | PAI-1[B] | 38.94 | 98.35 | 252.58 |
| IL-5 | 18.37 | 18.35 | 99.90 | I-TAC | 30.16 | 154.83 | 513.40 |
| IL-6 | 40.99 | 56.56 | 137.98 | MMP-12 | 12.41 | 27.69 | 223.09 |
| IL-7 | 15.82 | 6.61 | 41.79 | HGF | 206.22 | 619.73 | 300.52 |
| TGF-α | 31.46 | 8.00 | 25.44 | MMP-7 | 1004.07 | 577.62 | 57.53 |
| Fractalkine | 13.36 | 3.35 | 25.09 | EGF | 30.91 | 49.02 | 158.60 |
| IL-8 | 239.47 | 629.22 | 262.76 | sCD40 ligand | 155.50 | 434.04 | 279.12 |
| IL-10 | 13.06 | 3.63 | 27.82 | MMP-8 | 70.26 | 318.85 | 453.80 |
| IL-15 | 24.53 | 4.27 | 17.42 | | | | |

FIG. 3A

| FLUORESCENCE INTENSITY LEVEL IN THE LUNG CANCER POPULATION |||||||
|---|---|---|---|---|---|---|
| Biomarker | Average | S.D. | R.S.D. | Biomarker | Average | S.D. | R.S.D. |
| Adiponectin | 3563.76 | 2288.94 | 64.23 | IL-17 | 46.36 | 29.90 | 64.51 |
| Resistin | 191.29 | 136.17 | 71.19 | IL-1α | 122.68 | 394.79 | 321.80 |
| PAI-1[A] | 787.03 | 389.14 | 49.44 | IFN-γ | 28.31 | 9.99 | 35.29 |
| SE-selectin | 41.71 | 45.85 | 109.94 | G-CSF | 29.55 | 19.35 | 65.51 |
| sVCAM-1 | 1422.20 | 548.56 | 38.57 | GM-CSF | 33.26 | 10.06 | 30.23 |
| sICAM-1 | 3121.73 | 1440.47 | 46.14 | TNF-α | 75.33 | 359.82 | 477.69 |
| MPO | 2188.38 | 1952.85 | 89.24 | MCP-1 | 183.83 | 210.11 | 114.29 |
| CRP | 12951.79 | 5490.37 | 42.39 | IL-12 (p40) | 26.01 | 8.07 | 31.01 |
| SAA | 7383.07 | 6685.22 | 90.55 | MIP-1α | 53.41 | 97.52 | 182.57 |
| SAP | 1663.82 | 907.73 | 54.56 | MIP-1β | 33.74 | 81.49 | 241.55 |
| Leptin[1] | 1441.00 | 1806.76 | 125.38 | VEGF | 43.93 | 17.22 | 39.19 |
| GLP-1 | 130.29 | 700.99 | 538.03 | IL-12(p70) | 46.82 | 92.35 | 197.24 |
| Amylin (Total) | 337.43 | 1028.44 | 304.79 | IL-13 | 401.00 | 520.85 | 129.89 |
| C-Peptide | 3431.59 | 2603.38 | 75.87 | MMP-2 | 165.31 | 320.62 | 193.95 |
| Insulin | 373.06 | 777.90 | 208.52 | MMP-1 | 744.40 | 766.38 | 102.95 |
| Sfas | 68.60 | 41.26 | 60.15 | MMP-3 | 8137.21 | 3111.85 | 38.24 |
| sFSI | 18.15 | 58.41 | 321.91 | Eotaxin | 818.65 | 576.64 | 70.44 |
| MIF | 76.00 | 155.45 | 204.54 | Leptin[2] | 3214.92 | 3305.20 | 102.81 |
| IL-1β | 27.08 | 4.32 | 15.94 | IP-10 | 1846.73 | 1381.81 | 74.82 |
| IL-2 | 11.66 | 5.89 | 50.57 | MMP-9 | 3141.11 | 2616.52 | 83.30 |
| IL-1ra | 29.38 | 9.12 | 31.04 | MMP-13 | 21.06 | 189.11 | 898.16 |
| IL-4 | 154.43 | 214.60 | 138.96 | PAI-1[B] | 268.11 | 201.13 | 75.02 |
| IL-5 | 26.12 | 43.27 | 165.65 | I-TAC | 429.48 | 315.35 | 73.43 |
| IL-6 | 74.67 | 185.61 | 248.58 | MMP-12 | 32.74 | 168.74 | 515.37 |
| IL-7 | 23.67 | 73.58 | 310.88 | HGF | 678.43 | 787.38 | 116.06 |
| TGF-α | 37.56 | 12.62 | 33.59 | MMP-7 | 2070.90 | 1166.98 | 56.35 |
| Fractalkine | 15.27 | 4.37 | 28.58 | EGF | 455.13 | 462.40 | 101.60 |
| IL-8 | 168.26 | 286.40 | 170.21 | sCD40 ligand | 120.25 | 367.11 | 305.30 |
| IL-10 | 20.28 | 47.88 | 236.16 | MMP-8 | 284.02 | 494.63 | 174.15 |
| IL-15 | 28.90 | 7.04 | 24.37 | | | | |

FIG. 3B

| FLUORESCENCE INTENSITY LEVEL IN THE ASTHMA POPULATION | | | | | | | |
|---|---|---|---|---|---|---|---|
| Biomarker | Average | S.D. | R.S.D. | Biomarker | Average | S.D. | R.S.D. |
| Adiponectin | 2963.37 | 1855.21 | 62.60 | IL-17 | 48.31 | 24.48 | 50.68 |
| Resistin | 290.12 | 347.80 | 119.88 | IL-1α | 250.35 | 734.45 | 293.38 |
| PAI-1[A] | 791.20 | 259.58 | 32.81 | IFN-γ | 27.57 | 6.28 | 22.79 |
| SE-selectin | 37.42 | 26.25 | 70.14 | G-CSF | 27.42 | 12.61 | 45.98 |
| sVCAM-1 | 2580.30 | 1000.17 | 38.76 | GM-CSF | 35.60 | 26.94 | 75.67 |
| sICAM-1 | 3202.40 | 1322.66 | 41.30 | TNF-α | 69.25 | 272.27 | 393.15 |
| MPO | 3799.80 | 2433.44 | 64.04 | MCP-1 | 436.56 | 1969.47 | 451.13 |
| CRP | 10529.32 | 5894.42 | 55.98 | IL-12 (p40) | 26.81 | 8.15 | 30.41 |
| SAA | 3637.04 | 3965.44 | 109.03 | MIP-1α | 97.63 | 647.11 | 662.84 |
| SAP | 2336.72 | 646.89 | 27.68 | MIP-1β | 26.41 | 32.51 | 123.10 |
| Leptin[1] | 3009.58 | 2925.20 | 97.20 | VEGF | 46.98 | 18.08 | 38.48 |
| GLP-1 | 106.06 | 513.75 | 484.39 | IL12 (p70) | 32.48 | 54.69 | 168.40 |
| Amylin (Total) | 274.00 | 1007.69 | 367.77 | IL-13 | 297.79 | 362.17 | 121.62 |
| C-Peptide | 5509.05 | 2653.46 | 48.17 | MMP-2 | 184.87 | 248.32 | 134.32 |
| Insulin | 407.57 | 1178.79 | 289.22 | MMP-1 | 192.84 | 280.81 | 145.61 |
| Sfas | 76.93 | 40.19 | 52.24 | MMP-3 | 6150.32 | 2828.47 | 45.99 |
| sFSI | 31.20 | 48.27 | 154.71 | Eotaxin | 652.21 | 484.14 | 74.23 |
| MIF | 61.77 | 80.34 | 130.06 | Leptin[2] | 4322.85 | 3756.93 | 86.91 |
| IL-1β | 34.22 | 117.74 | 344.13 | IP-10 | 1575.99 | 1241.02 | 78.75 |
| IL-2 | 12.75 | 3.38 | 26.52 | MMP-9 | 4097.20 | 2679.44 | 65.40 |
| IL-1ra | 26.25 | 5.19 | 19.76 | MMP-13 | 9.37 | 38.54 | 411.12 |
| IL-4 | 190.65 | 318.74 | 167.19 | PAI-1[B] | 461.47 | 358.67 | 77.72 |
| IL-5 | 36.72 | 75.10 | 204.50 | I-TAC | 783.04 | 637.12 | 81.36 |
| IL-6 | 132.01 | 548.69 | 415.63 | MMP-12 | 20.79 | 42.60 | 204.89 |
| IL-7 | 23.30 | 13.78 | 59.16 | HGF | 1381.06 | 921.98 | 66.76 |
| TGF-α | 38.36 | 16.97 | 44.25 | MMP-7 | 487.07 | 493.70 | 101.36 |
| Fractalkine | 15.87 | 3.41 | 21.51 | EGF | 419.64 | 417.55 | 99.50 |
| IL-8 | 829.39 | 2332.42 | 281.22 | sCD40 ligand | 175.32 | 259.04 | 147.75 |
| IL-10 | 15.64 | 4.29 | 27.42 | MMP-8 | 140.35 | 889.83 | 634.00 |
| IL-15 | 27.01 | 7.96 | 29.47 | | | | |

FIG. 3C

| | PERCENT CHANGE IN MEAN FLUORESCENCE INTENSITY | | | | | | |
|---|---|---|---|---|---|---|---|
| Biomarker | AST vs. NO | LC vs. NO | AST vs. LC | Biomarker | AST vs. NO | LC vs. NO | AST vs. LC |
| Adiponectin | 31.15 | 57.72 | -20.26 | IL-17 | 28.48 | 23.29 | 4.04 |
| Resistin | 133.28 | 53.81 | 34.07 | IL-1α | 162.52 | 28.65 | 51.00 |
| PAI-1[A] | 136.11 | 134.86 | 0.53 | IFN-γ | 18.31 | 21.46 | -2.67 |
| SE-selectin | -37.99 | -30.88 | -11.46 | G-CSF | 15.02 | 23.95 | -7.76 |
| sVCAM-1 | 47.17 | -18.89 | 44.88 | GM-CSF | 24.45 | 16.28 | 6.57 |
| sICAM-1 | -2.83 | -5.28 | 2.52 | TNF-α | 59.14 | 73.10 | -8.77 |
| MPO | 541.07 | 269.21 | 42.41 | MCP-1 | 841.00 | 296.25 | 57.89 |
| CRP | 25.59 | 54.48 | -23.01 | IL-12 (p40) | 7.53 | 4.30 | 3.00 |
| SAA | 65.12 | 235.18 | -103.00 | MIP-1α | 137.86 | 30.14 | 45.29 |
| SAP | 6.18 | -24.40 | 28.80 | MIP-1β | 24.09 | 58.53 | -27.75 |
| Leptin[1] | 36.51 | -34.64 | 52.12 | VEGF | 15.13 | 7.67 | 6.48 |
| GLP-1 | 88.68 | 131.77 | -22.84 | IL12 (p70) | 324.00 | 511.21 | -44.15 |
| Amylin (Total) | 92.32 | 136.84 | -23.15 | IL-13 | 2509.42 | 3413.77 | -34.66 |
| C-Peptide | 16.01 | -27.73 | 37.71 | MMP-2 | 18.71 | 6.15 | 10.58 |
| Insulin | 46.55 | 34.14 | 8.47 | MMP-1 | 86.29 | 619.10 | -286.01 |
| Sfas | 30.81 | 16.64 | 10.83 | MMP-3 | -7.77 | 22.02 | -32.31 |
| sFSI | 106.17 | 19.89 | 41.85 | Eotaxin | 231.44 | 316.02 | -25.52 |
| MIF | 18.62 | 45.93 | -23.03 | Leptin[2] | 14.73 | -14.67 | 25.63 |
| IL-1β | 44.28 | 14.18 | 20.86 | IP-10 | 190.01 | 239.83 | -17.18 |
| IL-2 | 3.97 | -4.95 | 8.58 | MMP-9 | 275.71 | 188.04 | 23.34 |
| IL-1ra | 13.62 | 27.16 | -11.92 | MMP-13 | -5.75 | 111.71 | -124.61 |
| IL-4 | 66.67 | 35.00 | 19.00 | PAI-1[B] | 1085.19 | 588.59 | 41.90 |
| IL-5 | 99.90 | 42.20 | 28.87 | I-TAC | 2496.41 | 1324.07 | 45.15 |
| IL-6 | 222.04 | 82.15 | 43.44 | MMP-12 | 67.51 | 163.78 | -57.47 |
| IL-7 | 47.25 | 49.61 | -1.60 | HGF | 569.70 | 228.98 | 50.88 |
| TGF-α | 21.95 | 19.41 | 2.08 | MMP-7 | -51.49 | 106.25 | -325.18 |
| Fractalkine | 18.84 | 14.34 | 3.78 | EGF | 1257.75 | 1372.57 | -8.46 |
| IL-8 | 246.35 | -29.74 | 79.71 | sCD40 ligand | 12.74 | -22.67 | 31.41 |
| IL-10 | 19.70 | 55.21 | -29.66 | MMP-8 | 99.75 | 304.23 | -102.36 |
| IL-15 | 10.11 | 17.84 | -7.02 | | | | |

FIG. 3D

SIGNIFICANCE OF POPULATION DIFFERENCES EXPRESSED AS PROBABILITY OF STUDENT'S T VALUE

| Biomarker | TAST vs. NO | TLC vs. NO | TAST vs. LC | Biomarker | TAST vs. NO | TLC vs. NO | TAST vs. LC |
|---|---|---|---|---|---|---|---|
| Adiponectin | 0.000 | 0.000 | 0.002 | IL-17 | 0.000 | 0.000 | 0.449 |
| Resistin | 0.000 | 0.000 | 0.000 | IL-1α | 0.001 | 0.279 | 0.009 |
| PAI-1[A] | 0.000 | 0.000 | 0.896 | IFN-γ | 0.000 | 0.000 | 0.367 |
| SE-selectin | 0.000 | 0.000 | 0.246 | G-CSF | 0.000 | 0.000 | 0.181 |
| sVCAM-1 | 0.000 | 0.000 | 0.000 | GM-CSF | 0.000 | 0.000 | 0.146 |
| sICAM-1 | 0.508 | 0.143 | 0.529 | TNF-α | 0.110 | 0.134 | 0.842 |
| MPO | 0.000 | 0.000 | 0.000 | MCP-1 | 0.001 | 0.000 | 0.016 |
| CRP | 0.000 | 0.000 | 0.000 | IL-12 (p40) | 0.010 | 0.079 | 0.277 |
| SAA | 0.000 | 0.000 | 0.000 | MIP-1α | 0.139 | 0.037 | 0.205 |
| SAP | 0.018 | 0.000 | 0.000 | MIP-1β | 0.013 | 0.010 | 0.246 |
| Leptin[1] | 0.003 | 0.000 | 0.000 | VEGF | 0.000 | 0.008 | 0.057 |
| GLP-1 | 0.111 | 0.076 | 0.681 | IL12 (p70) | 0.000 | 0.000 | 0.055 |
| Amylin (Total) | 0.042 | 0.002 | 0.497 | IL-13 | 0.000 | 0.000 | 0.017 |
| C-Peptide | 0.000 | 0.000 | 0.000 | MMP-2 | 0.417 | 0.749 | 0.473 |
| Insulin | 0.090 | 0.063 | 0.685 | MMP-1 | 0.000 | 0.000 | 0.000 |
| Sfas | 0.110 | 0.232 | 0.026 | MMP-3 | 0.036 | 0.000 | 0.000 |
| sFSI | 0.000 | 0.397 | 0.010 | Eotaxin | 0.000 | 0.000 | 0.001 |
| MIF | 0.314 | 0.029 | 0.250 | Leptin[2] | 0.129 | 0.051 | 0.000 |
| IL-1β | 0.133 | 0.000 | 0.251 | IP-10 | 0.000 | 0.000 | 0.027 |
| IL-2 | 0.882 | 0.796 | 0.021 | MMP-9 | 0.000 | 0.000 | 0.000 |
| IL-1ra | 0.033 | 0.000 | 0.000 | MMP-13 | 0.870 | 0.326 | 0.413 |
| IL-4 | 0.000 | 0.003 | 0.119 | PAI-1[B] | 0.000 | 0.000 | 0.000 |
| IL-5 | 0.000 | 0.005 | 0.038 | I-TAC | 0.000 | 0.000 | 0.000 |
| IL-6 | 0.005 | 0.003 | 0.074 | MMP-12 | 0.010 | 0.044 | 0.350 |
| IL-7 | 0.000 | 0.072 | 0.946 | HGF | 0.000 | 0.000 | 0.000 |
| TGF-α | 0.000 | 0.000 | 0.539 | MMP-7 | 0.000 | 0.000 | 0.000 |
| Fractalkine | 0.000 | 0.000 | 0.107 | EGF | 0.000 | 0.000 | 0.386 |
| IL-8 | 0.000 | 0.056 | 0.000 | sCD40 ligand | 0.580 | 0.263 | 0.072 |
| IL-10 | 0.000 | 0.011 | 0.195 | MMP-8 | 0.224 | 0.000 | 0.016 |
| IL-15 | 0.000 | 0.000 | 0.005 | | | | |

FIG. 3E

| FLUORESCENCE INTENSITY IN THE NORMAL FEMALE POPULATION |||||||
|---|---|---|---|---|---|---|
| Biomarker | Average | S.D. | R.S.D. | Biomarker | Average | S.D. | R.S.D. |
| Adiponectin | 2116.17 | 1225.14 | 57.89 | IL-17 | 41.58 | 12.84 | 30.88 |
| Resistin | 158.01 | 95.09 | 60.18 | IL-1α | 83.31 | 155.36 | 186.48 |
| PAI-1[A] | 499.52 | 438.77 | 87.84 | IFN-γ | 26.73 | 11.79 | 44.13 |
| SE-selectin | 75.37 | 56.07 | 74.40 | G-CSF | 26.24 | 3.43 | 13.09 |
| sVCAM-1 | 1658.49 | 448.12 | 27.02 | GM-CSF | 30.93 | 4.43 | 14.32 |
| sICAM-1 | 3520.37 | 1512.81 | 42.97 | TNF-α | 54.88 | 13.94 | 25.40 |
| MPO | 1269.64 | 2084.74 | 164.20 | MCP-1 | 59.33 | 39.47 | 66.53 |
| CRP | 7532.14 | 5561.16 | 73.83 | IL-12 (p40) | 27.09 | 6.13 | 22.64 |
| SAA | 1773.59 | 3197.93 | 180.31 | MIP-1α | 50.13 | 39.77 | 79.34 |
| SAP | 2238.83 | 555.16 | 24.80 | MIP-1β | 26.92 | 11.02 | 40.96 |
| Leptin[1] | 860.83 | 1311.22 | 152.32 | VEGF | 43.79 | 9.56 | 21.83 |
| GLP-1 | 54.12 | 99.58 | 184.01 | IL-12(p70) | 7.87 | 11.21 | 142.41 |
| Amylin (Total) | 161.50 | 469.30 | 290.59 | IL-13 | 27.17 | 74.25 | 273.33 |
| C-Peptide | 4048.15 | 1725.03 | 42.61 | MMP-2 | 132.15 | 148.40 | 112.30 |
| Insulin | 287.45 | 463.63 | 161.29 | MMP-1 | 182.66 | 242.24 | 132.62 |
| Sfas | 63.98 | 42.36 | 66.21 | MMP-3 | 7467.26 | 2419.60 | 32.40 |
| sFSI | 13.35 | 10.94 | 81.94 | Eotaxin | 289.67 | 253.39 | 87.48 |
| MIF | 105.73 | 157.68 | 149.14 | Leptin[2] | 2169.69 | 2831.50 | 130.50 |
| IL-1β | 26.63 | 13.82 | 51.90 | IP-10 | 452.58 | 410.35 | 90.67 |
| IL-2 | 11.04 | 2.32 | 21.05 | MMP-9 | 1713.45 | 2162.04 | 126.18 |
| IL-1ra | 24.48 | 3.85 | 15.71 | MMP-13 | 14.07 | 51.00 | 362.52 |
| IL-4 | 105.32 | 60.09 | 57.05 | PAI-1[B] | 66.22 | 113.55 | 171.47 |
| IL-5 | 18.93 | 19.27 | 101.80 | I-TAC | 92.89 | 207.98 | 223.91 |
| IL-6 | 43.44 | 57.12 | 131.50 | MMP-12 | 15.55 | 36.33 | 233.59 |
| IL-7 | 17.80 | 6.28 | 35.26 | HGF | 538.75 | 846.22 | 157.07 |
| TGF-α | 34.76 | 7.54 | 21.70 | MMP-7 | 1163.17 | 547.69 | 47.09 |
| Fractalkine | 14.96 | 2.95 | 19.71 | EGF | 48.56 | 64.54 | 132.92 |
| IL-8 | 401.98 | 915.65 | 227.79 | sCD40 ligand | 139.86 | 213.56 | 152.69 |
| IL-10 | 14.76 | 3.07 | 20.81 | MMP-8 | 222.46 | 446.02 | 200.50 |
| IL-15 | 26.97 | 3.76 | 13.93 | | | | |

FIG. 4A

| FLUORESCENCE INTENSITY IN THE FEMALE POPULATION WITH LUNG CANCER ||||||||
|---|---|---|---|---|---|---|---|
| Biomarker | Average | S.D. | R.S.D. | Biomarker | Average | S.D. | R.S.D. |
| Adiponectin | 4041.07 | 2456.96 | 60.80 | IL-17 | 45.15 | 20.95 | 46.40 |
| Resistin | 165.14 | 104.34 | 63.18 | IL-1α | 101.95 | 454.84 | 446.12 |
| PAI-1[A] | 680.06 | 281.74 | 41.43 | IFN-γ | 29.47 | 10.86 | 36.86 |
| SE-selectin | 39.28 | 24.76 | 63.02 | G-CSF | 28.03 | 7.27 | 25.95 |
| sVCAM-1 | 1486.20 | 580.24 | 39.04 | GM-CSF | 33.00 | 6.80 | 20.61 |
| sICAM-1 | 3129.94 | 1388.46 | 44.36 | TNF-α | 113.63 | 639.16 | 562.50 |
| MPO | 2236.00 | 2021.46 | 90.41 | MCP-1 | 175.20 | 224.24 | 127.99 |
| CRP | 12373.56 | 6171.04 | 49.87 | IL-12 (p40) | 25.63 | 9.73 | 37.96 |
| SAA | 6407.43 | 6756.26 | 105.44 | MIP-1α | 67.31 | 169.37 | 251.61 |
| SAP | 1610.90 | 912.77 | 56.66 | MIP-1β | 41.90 | 143.28 | 341.91 |
| Leptin[1] | 1836.07 | 2086.83 | 113.66 | VEGF | 41.74 | 11.81 | 28.30 |
| GLP-1 | 112.59 | 751.23 | 667.22 | IL-12(p70) | 58.24 | 142.89 | 245.35 |
| Amylin (Total) | 252.51 | 919.35 | 364.09 | IL-13 | 410.97 | 510.37 | 124.18 |
| C-Peptide | 3270.49 | 2492.50 | 76.21 | MMP-2 | 139.64 | 205.55 | 147.20 |
| Insulin | 338.74 | 801.56 | 236.63 | MMP-1 | 602.07 | 546.07 | 90.70 |
| Sfas | 64.72 | 36.09 | 55.76 | MMP-3 | 7690.73 | 3309.64 | 43.03 |
| sFSI | 13.51 | 21.88 | 161.99 | Eotaxin | 814.32 | 573.07 | 70.37 |
| MIF | 55.10 | 97.46 | 176.88 | Leptin[2] | 3933.88 | 3864.56 | 98.24 |
| IL-1β | 27.70 | 4.44 | 16.03 | IP-10 | 1631.25 | 1066.13 | 65.36 |
| IL-2 | 12.03 | 5.77 | 47.98 | MMP-9 | 3423.98 | 2497.43 | 72.94 |
| IL-1ra | 29.50 | 8.33 | 28.23 | MMP-13 | 11.66 | 33.41 | 286.54 |
| IL-4 | 130.02 | 173.21 | 133.21 | PAI-1[B] | 244.76 | 206.20 | 84.24 |
| IL-5 | 22.15 | 44.14 | 199.26 | I-TAC | 387.53 | 314.80 | 81.23 |
| IL-6 | 70.54 | 257.76 | 365.41 | MMP-12 | 24.93 | 36.33 | 145.74 |
| IL-7 | 31.77 | 130.07 | 409.42 | HGF | 537.31 | 620.75 | 115.53 |
| TGF-α | 36.97 | 12.35 | 33.42 | MMP-7 | 2122.99 | 1114.85 | 52.51 |
| Fractalkine | 15.30 | 4.82 | 31.48 | EGF | 422.32 | 483.79 | 114.56 |
| IL-8 | 126.83 | 168.86 | 133.13 | sCD40 ligand | 99.65 | 261.62 | 262.55 |
| IL-10 | 27.03 | 84.44 | 312.39 | MMP-8 | 247.64 | 364.87 | 147.34 |
| IL-15 | 28.91 | 6.61 | 22.86 | | | | |

FIG. 4B

FLUORESCENCE INTENSITY LEVEL IN THE FEMALE POPULATION WITH ASTHMA

| Biomarker | Average | S.D. | R.S.D. | Biomarker | Average | S.D. | R.S.D. |
|---|---|---|---|---|---|---|---|
| Adiponectin | 2944.64 | 1614.58 | 54.83 | IL-17 | 43.39 | 21.49 | 49.53 |
| Resistin | 332.29 | 416.68 | 125.40 | IL-1α | 164.86 | 441.25 | 267.64 |
| PAI-1[A] | 841.92 | 266.60 | 31.67 | IFN-γ | 27.88 | 6.03 | 21.64 |
| SE-selectin | 36.85 | 25.26 | 68.56 | G-CSF | 21.06 | 4.35 | 20.67 |
| sVCAM-1 | 2435.16 | 971.17 | 39.88 | GM-CSF | 28.29 | 5.43 | 19.20 |
| sICAM-1 | 3084.39 | 1425.90 | 46.23 | TNF-α | 43.88 | 8.91 | 20.30 |
| MPO | 4056.85 | 2406.72 | 59.32 | MCP-1 | 337.96 | 1126.34 | 333.28 |
| CRP | 11504.22 | 6148.46 | 53.45 | IL-12 (p40) | 23.53 | 5.49 | 23.34 |
| SAA | 3764.05 | 3808.32 | 101.18 | MIP-1α | 47.70 | 29.11 | 61.04 |
| SAP | 2216.83 | 576.86 | 26.02 | MIP-1β | 22.11 | 6.60 | 29.87 |
| Leptin[1] | 4148.56 | 3054.11 | 73.62 | VEGF | 40.46 | 9.69 | 23.95 |
| GLP-1 | 153.82 | 647.05 | 420.66 | IL-12(p70) | 30.32 | 53.08 | 175.08 |
| Amylin (Total) | 377.66 | 1265.49 | 335.09 | IL-13 | 307.87 | 373.66 | 121.37 |
| C-Peptide | 5897.41 | 2865.27 | 48.59 | MMP-2 | 222.30 | 297.87 | 134.00 |
| Insulin | 521.74 | 1464.79 | 280.75 | MMP-1 | 239.58 | 326.58 | 136.31 |
| Sfas | 88.02 | 45.72 | 51.94 | MMP-3 | 6158.26 | 2312.49 | 37.55 |
| sFSI | 26.67 | 43.10 | 161.59 | Eotaxin | 676.90 | 441.51 | 65.23 |
| MIF | 50.56 | 92.56 | 183.07 | Leptin[2] | 5870.26 | 3702.57 | 63.07 |
| IL-1β | 23.81 | 4.81 | 20.19 | IP-10 | 1698.22 | 1212.85 | 71.42 |
| IL-2 | 12.46 | 3.21 | 25.76 | MMP-9 | 4522.52 | 2746.21 | 60.72 |
| IL-1ra | 26.42 | 5.68 | 21.51 | MMP-13 | 11.59 | 48.42 | 417.84 |
| IL-4 | 147.54 | 195.73 | 132.66 | PAI-1[B] | 512.32 | 379.29 | 74.03 |
| IL-5 | 27.72 | 42.32 | 152.66 | I-TAC | 890.86 | 677.56 | 76.06 |
| IL-6 | 69.69 | 142.44 | 204.39 | MMP-12 | 24.82 | 51.96 | 209.35 |
| IL-7 | 18.13 | 7.94 | 43.80 | HGF | 1549.14 | 858.93 | 55.45 |
| TGF-α | 32.08 | 15.94 | 49.69 | MMP-7 | 517.14 | 462.20 | 89.38 |
| Fractalkine | 15.25 | 2.85 | 18.70 | EGF | 405.07 | 357.97 | 88.37 |
| IL-8 | 704.24 | 1718.95 | 244.09 | sCD40 ligand | 213.58 | 312.95 | 146.52 |
| IL-10 | 14.95 | 4.15 | 27.78 | MMP-8 | 192.74 | 1107.98 | 574.85 |
| IL-15 | 22.54 | 4.34 | 19.27 | | | | |

FIG. 4C

PERCENT CHANGE IN MEAN FLUORESCENCE INTENSITY IN THE FEMALE POPULATION

| Biomarker | AST vs. NO | LC vs. NO | AST vs. LC | Biomarker | AST vs. NO | LC vs. NO | AST vs. LC |
|---|---|---|---|---|---|---|---|
| Adiponectin | 39.15 | 90.96 | -37.23 | IL-17 | 4.37 | 8.59 | -4.04 |
| Resistin | 110.29 | 4.51 | 50.30 | IL-1α | 97.89 | 22.38 | 38.16 |
| PAI-1[A] | 68.55 | 36.14 | 19.23 | IFN-γ | 4.32 | 10.26 | -5.70 |
| SE-selectin | -51.10 | -47.88 | -6.59 | G-CSF | -19.75 | 6.81 | -33.10 |
| sVCAM-1 | 46.83 | -10.39 | 38.97 | GM-CSF | -8.54 | 6.71 | -16.67 |
| sICAM-1 | -12.38 | -11.09 | -1.48 | TNF-α | -20.04 | 107.06 | -158.93 |
| MPO | 219.53 | 76.11 | 44.88 | MCP-1 | 469.66 | 195.31 | 48.16 |
| CRP | 52.74 | 64.28 | -7.56 | IL-12 (p40) | -13.17 | -5.40 | -8.95 |
| SAA | 112.23 | 261.27 | -70.23 | MIP-1α | -4.86 | 34.27 | -41.12 |
| SAP | -0.98 | -28.05 | 27.33 | MIP-1β | -17.86 | 55.68 | -89.54 |
| Leptin[1] | 381.92 | 113.29 | 55.74 | VEGF | -7.61 | -4.67 | -3.18 |
| GLP-1 | 184.22 | 108.05 | 26.80 | IL-12(p70) | 285.01 | 639.61 | -92.10 |
| Amylin (Total) | 133.85 | 56.35 | 33.14 | IL-13 | 1033.27 | 1412.81 | -33.49 |
| C-Peptide | 45.68 | -19.21 | 44.54 | MMP-2 | 68.22 | 5.67 | 37.18 |
| Insulin | 81.51 | 17.85 | 35.07 | MMP-1 | 31.16 | 229.61 | -151.30 |
| Sfas | 37.56 | 1.15 | 26.47 | MMP-3 | -17.53 | 2.99 | -24.88 |
| sFSI | 99.73 | 1.15 | 49.36 | Eotaxin | 133.68 | 181.12 | -20.30 |
| MIF | -52.18 | -47.89 | -8.98 | Leptin[2] | 170.56 | 81.31 | 32.99 |
| IL-1β | -10.60 | 3.99 | -16.33 | IP-10 | 275.23 | 260.44 | 3.94 |
| IL-2 | 12.92 | 8.99 | 3.48 | MMP-9 | 163.94 | 99.83 | 24.29 |
| IL-1ra | 7.92 | 20.47 | -11.63 | MMP-13 | -17.64 | -17.11 | -0.64 |
| IL-4 | 40.08 | 23.45 | 11.87 | PAI-1[B] | 673.63 | 269.60 | 52.23 |
| IL-5 | 46.45 | 17.02 | 20.10 | I-TAC | 859.07 | 317.20 | 56.50 |
| IL-6 | 60.44 | 62.39 | -1.22 | MMP-12 | 59.60 | 60.26 | -0.42 |
| IL-7 | 1.86 | 78.45 | -75.19 | HGF | 187.55 | -0.27 | 65.32 |
| TGF-α | -7.71 | 6.37 | -15.26 | MMP-7 | -55.54 | 82.52 | -310.52 |
| Fractalkine | 1.99 | 2.30 | -0.31 | EGF | 734.23 | 769.75 | -4.26 |
| IL-8 | 75.19 | -68.45 | 81.99 | sCD40 ligand | 52.72 | -28.75 | 53.35 |
| IL-10 | 1.34 | 83.17 | -80.75 | MMP-8 | -13.36 | 11.32 | -28.48 |
| IL-15 | -16.41 | 7.20 | -28.25 | | | | |

FIG. 4D

| SIGNIFICANCE OF POPULATION DIFFERENCES EXPRESSED AS PROBABILITY OF STUDENT'S T VALUE FOR FEMALE POPULATIONS | | | | | | | |
|---|---|---|---|---|---|---|---|
| Biomarker | T AST vs. NO | T LC vs. NO | T AST vs. LC | Biomarker | T AST vs. NO | T LC vs. NO | T AST vs. LC |
| Adiponectin | 0.000 | 0.000 | 0.000 | IL-17 | 0.429 | 0.113 | 0.768 |
| Resistin | 0.000 | 0.583 | 0.000 | IL-1α | 0.057 | 0.670 | 0.010 |
| PAI-1$^A$ | 0.000 | 0.000 | 0.078 | IFN-γ | 0.354 | 0.065 | 0.054 |
| SE-selectin | 0.000 | 0.000 | 0.179 | G-CSF | 0.000 | 0.016 | 0.150 |
| sVCAM-1 | 0.000 | 0.011 | 0.000 | GM-CSF | 0.000 | 0.006 | 0.253 |
| sICAM-1 | 0.025 | 0.040 | 0.658 | TNF-α | 0.000 | 0.311 | 0.451 |
| MPO | 0.000 | 0.000 | 0.000 | MCP-1 | 0.007 | 0.000 | 0.148 |
| CRP | 0.000 | 0.000 | 0.000 | IL-12 (p40) | 0.000 | 0.166 | 0.553 |
| SAA | 0.000 | 0.000 | 0.000 | MIP-1α | 0.596 | 0.277 | 0.208 |
| SAP | 0.767 | 0.000 | 0.000 | MIP-1β | 0.000 | 0.251 | 0.098 |
| Leptin$^1$ | 0.000 | 0.000 | 0.000 | VEGF | 0.009 | 0.144 | 0.163 |
| GLP-1 | 0.094 | 0.395 | 0.248 | IL-12(p70) | 0.000 | 0.000 | 0.142 |
| Amylin (Total) | 0.080 | 0.335 | 0.147 | IL-13 | 0.000 | 0.000 | 0.075 |
| C-Peptide | 0.000 | 0.006 | 0.000 | MMP-2 | 0.003 | 0.747 | 0.564 |
| Insulin | 0.095 | 0.545 | 0.608 | MMP-1 | 0.129 | 0.000 | 0.000 |
| Sfas | 0.000 | 0.886 | 0.797 | MMP-3 | 0.000 | 0.553 | 0.000 |
| sFSI | 0.001 | 0.945 | 0.017 | Eotaxin | 0.000 | 0.000 | 0.007 |
| MIF | 0.001 | 0.004 | 0.303 | Leptin$^2$ | 0.000 | 0.000 | 0.021 |
| IL-1β | 0.041 | 0.433 | 0.278 | IP-10 | 0.000 | 0.000 | 0.001 |
| IL-2 | 0.000 | 0.081 | 0.136 | MMP-9 | 0.000 | 0.000 | 0.003 |
| IL-1ra | 0.002 | 0.000 | 0.000 | MMP-13 | 0.704 | 0.671 | 0.416 |
| IL-4 | 0.024 | 0.140 | 0.147 | PAI-1$^B$ | 0.000 | 0.000 | 0.000 |
| IL-5 | 0.039 | 0.463 | 0.094 | I-TAC | 0.000 | 0.000 | 0.000 |
| IL-6 | 0.062 | 0.259 | 0.046 | MMP-12 | 0.113 | 0.049 | 0.380 |
| IL-7 | 0.723 | 0.237 | 0.798 | HGF | 0.000 | 0.988 | 0.000 |
| TGF-α | 0.097 | 0.096 | 0.724 | MMP-7 | 0.000 | 0.000 | 0.000 |
| Fractalkine | 0.435 | 0.505 | 0.631 | EGF | 0.000 | 0.000 | 0.690 |
| IL-8 | 0.091 | 0.002 | 0.001 | sCD40 ligand | 0.035 | 0.196 | 0.106 |
| IL-10 | 0.677 | 0.110 | 0.000 | MMP-8 | 0.785 | 0.637 | 0.000 |
| IL-15 | 0.000 | 0.006 | 0.001 | | | | |

FIG. 4E

| \multicolumn{8}{|c|}{FLUORESCENCE INTENSITY IN THE NORMAL MALE POPULATION} |

| Biomarker | Average | S.D. | R.S.D. | Biomarker | Average | S.D. | R.S.D. |
|---|---|---|---|---|---|---|---|
| Adiponectin | 2375.01 | 1677.13 | 70.62 | IL-17 | 34.68 | 13.33 | 38.44 |
| Resistin | 99.39 | 78.12 | 78.60 | IL-1α | 104.49 | 205.17 | 196.36 |
| PAI-1[A] | 213.37 | 254.21 | 119.14 | IFN-γ | 20.78 | 5.73 | 27.58 |
| SE-selectin | 49.28 | 36.75 | 74.57 | G-CSF | 22.05 | 3.68 | 16.68 |
| sVCAM-1 | 1822.54 | 548.47 | 30.09 | GM-CSF | 26.91 | 15.97 | 59.33 |
| sICAM-1 | 3128.49 | 1607.19 | 51.37 | TNF-α | 35.13 | 11.03 | 31.38 |
| MPO | 95.40 | 396.70 | 415.85 | MCP-1 | 36.83 | 12.40 | 33.66 |
| CRP | 8947.58 | 6700.43 | 74.89 | IL-12 (p40) | 23.35 | 7.64 | 32.74 |
| SAA | 2444.04 | 4420.98 | 180.89 | MIP-1α | 34.36 | 7.76 | 22.58 |
| SAP | 2170.66 | 583.20 | 26.87 | MIP-1β | 17.13 | 6.29 | 36.73 |
| Leptin[1] | 3159.85 | 3108.95 | 98.39 | VEGF | 38.60 | 12.27 | 31.79 |
| GLP-1 | 57.97 | 105.08 | 181.26 | IL-12(p70) | 7.53 | 47.57 | 631.42 |
| Amylin (Total) | 127.91 | 196.50 | 153.63 | IL-13 | -0.07 | 36.12 | -48855.51 |
| C-Peptide | 5243.25 | 1975.58 | 37.68 | MMP-2 | 173.98 | 566.49 | 325.61 |
| Insulin | 269.95 | 395.42 | 146.48 | MMP-1 | 45.54 | 70.31 | 154.37 |
| Sfas | 54.83 | 192.79 | 351.58 | MMP-3 | 6075.64 | 2300.75 | 37.87 |
| sFSI | 16.47 | 20.16 | 122.40 | Eotaxin | 127.35 | 132.34 | 103.92 |
| MIF | 12.66 | 6.60 | 52.09 | Leptin[2] | 4899.58 | 4110.65 | 83.90 |
| IL-1β | 21.56 | 2.60 | 12.05 | IP-10 | 612.33 | 1020.53 | 166.66 |
| IL-2 | 13.17 | 58.19 | 441.69 | MMP-9 | 635.66 | 724.02 | 113.90 |
| IL-1ra | 22.06 | 25.34 | 114.88 | MMP-13 | 6.92 | 16.91 | 244.36 |
| IL-4 | 121.09 | 79.91 | 65.99 | PAI-1[B] | 13.51 | 73.47 | 543.75 |
| IL-5 | 17.97 | 17.75 | 98.78 | I-TAC | -15.62 | 70.30 | -450.19 |
| IL-6 | 39.17 | 56.42 | 144.04 | MMP-12 | -10.06 | 18.84 | 187.30 |
| IL-7 | 14.36 | 6.51 | 45.31 | HGF | -38.01 | 32.84 | -86.39 |
| TGF-α | 29.04 | 7.49 | 25.78 | MMP-7 | 892.29 | 570.49 | 63.94 |
| Fractalkine | 12.16 | 3.14 | 25.82 | EGF | 17.96 | 27.01 | 150.43 |
| IL-8 | 120.31 | 200.43 | 166.59 | sCD40 ligand | 167.64 | 543.74 | 324.35 |
| IL-10 | 11.81 | 3.52 | 29.85 | MMP-8 | -41.37 | 35.20 | -85.08 |
| IL-15 | 22.73 | 3.72 | 16.36 | | | | |

FIG. 5A

| FLUORESCENCE INTENSITY IN THE MALE LUNG CANCER POPULATION ||||||||
|---|---|---|---|---|---|---|---|
| Biomarker | Average | S.D. | R.S.D. | Biomarker | Average | S.D. | R.S.D. |
| Adiponectin | 3308.09 | 2112.68 | 63.86 | IL-17 | 46.93 | 33.34 | 71.03 |
| Resistin | 203.24 | 147.53 | 72.59 | IL-1α | 132.63 | 364.95 | 275.17 |
| PAI-1[A] | 837.56 | 421.88 | 50.37 | IFN-γ | 27.78 | 9.55 | 34.39 |
| SE-selectin | 42.79 | 52.96 | 123.79 | G-CSF | 30.21 | 22.90 | 75.83 |
| sVCAM-1 | 1392.31 | 532.93 | 38.28 | GM-CSF | 33.37 | 11.28 | 33.81 |
| sICAM-1 | 3120.40 | 1469.20 | 47.08 | TNF-α | 57.62 | 17.36 | 30.13 |
| MPO | 2172.28 | 1925.67 | 88.65 | MCP-1 | 187.93 | 203.98 | 108.54 |
| CRP | 13265.74 | 5095.50 | 38.41 | IL-12 (p40) | 26.17 | 7.19 | 27.49 |
| SAA | 7854.70 | 6623.56 | 84.33 | MIP-1α | 47.00 | 23.96 | 50.98 |
| SAP | 1689.28 | 907.93 | 53.75 | MIP-1β | 30.00 | 14.79 | 49.29 |
| Leptin[1] | 1241.43 | 1616.24 | 130.19 | VEGF | 44.89 | 19.17 | 42.71 |
| GLP-1 | 138.75 | 679.26 | 489.56 | IL-12(p70) | 41.57 | 54.79 | 131.80 |
| Amylin (Total) | 377.72 | 1076.85 | 285.09 | IL-13 | 397.79 | 527.21 | 132.54 |
| C-Peptide | 3518.32 | 2653.51 | 75.42 | MMP-2 | 177.06 | 362.25 | 204.59 |
| Insulin | 388.05 | 769.26 | 198.24 | MMP-1 | 811.18 | 843.83 | 104.03 |
| Sfas | 70.28 | 43.45 | 61.83 | MMP-3 | 8324.20 | 2990.06 | 35.92 |
| sFSI | 20.35 | 69.16 | 339.84 | Eotaxin | 815.97 | 575.92 | 70.58 |
| MIF | 85.95 | 175.61 | 204.33 | Leptin[2] | 2860.57 | 2948.31 | 103.07 |
| IL-1β | 26.79 | 4.24 | 15.84 | IP-10 | 1949.78 | 1499.56 | 76.91 |
| IL-2 | 11.49 | 5.97 | 51.93 | MMP-9 | 3017.93 | 2667.24 | 88.38 |
| IL-1ra | 29.34 | 9.50 | 32.36 | MMP-13 | 25.44 | 228.13 | 896.89 |
| IL-4 | 165.98 | 231.18 | 139.28 | PAI-1[B] | 279.67 | 198.30 | 70.91 |
| IL-5 | 28.01 | 42.91 | 153.18 | I-TAC | 450.09 | 314.46 | 69.87 |
| IL-6 | 76.81 | 141.04 | 183.63 | MMP-12 | 36.42 | 203.07 | 557.58 |
| IL-7 | 19.93 | 9.24 | 46.38 | HGF | 746.89 | 847.21 | 113.43 |
| TGF-α | 37.83 | 12.78 | 33.77 | MMP-7 | 2049.58 | 1193.44 | 58.23 |
| Fractalkine | 15.26 | 4.16 | 27.25 | EGF | 471.66 | 452.79 | 96.00 |
| IL-8 | 187.89 | 325.97 | 173.49 | sCD40 ligand | 129.51 | 407.77 | 314.85 |
| IL-10 | 17.14 | 6.35 | 37.07 | MMP-8 | 300.58 | 545.34 | 181.43 |
| IL-15 | 28.87 | 7.24 | 25.09 | | | | |

FIG. 5B

| FLUORESCENCE INTENSITY LEVEL IN THE MALE ASTHMA POPULATION | | | | | | | |
|---|---|---|---|---|---|---|---|
| Biomarker | Average | S.D. | R.S.D. | Biomarker | Average | S.D. | R.S.D. |
| Adiponectin | 2947.72 | 2190.78 | 74.32 | IL-17 | 56.69 | 27.10 | 47.81 |
| Resistin | 221.87 | 167.29 | 75.40 | IL-1α | 396.04 | 1049.31 | 264.95 |
| PAI-1[A] | 711.75 | 224.74 | 31.58 | IFN-γ | 27.11 | 6.72 | 24.79 |
| SE-selectin | 38.26 | 28.16 | 73.59 | G-CSF | 38.02 | 14.71 | 38.68 |
| sVCAM-1 | 2829.19 | 1012.66 | 35.79 | GM-CSF | 47.83 | 40.94 | 85.59 |
| sICAM-1 | 3394.91 | 1123.56 | 33.10 | TNF-α | 111.92 | 444.94 | 397.55 |
| MPO | 3403.65 | 2428.77 | 71.36 | MCP-1 | 606.76 | 2887.62 | 475.91 |
| CRP | 8963.97 | 5125.42 | 57.18 | IL-12 (p40) | 32.29 | 8.99 | 27.84 |
| SAA | 3443.76 | 4262.10 | 123.76 | MIP-1α | 182.01 | 1059.60 | 582.15 |
| SAP | 2535.86 | 714.51 | 28.18 | MIP-1β | 33.66 | 52.04 | 154.58 |
| Leptin[1] | 1141.66 | 1299.27 | 113.81 | VEGF | 57.87 | 23.15 | 40.00 |
| GLP-1 | 27.56 | 38.25 | 138.81 | IL-12(p70) | 36.55 | 57.75 | 158.03 |
| Amylin (Total) | 104.12 | 110.92 | 106.53 | IL-13 | 284.25 | 346.16 | 121.78 |
| C-Peptide | 4893.34 | 2138.06 | 43.69 | MMP-2 | 124.45 | 107.75 | 86.58 |
| Insulin | 222.02 | 317.93 | 143.20 | MMP-1 | 117.09 | 156.76 | 133.88 |
| Sfas | 58.05 | 16.92 | 29.15 | MMP-3 | 6119.28 | 3561.09 | 58.19 |
| sFSI | 38.99 | 55.65 | 142.74 | Eotaxin | 610.56 | 552.32 | 90.46 |
| MIF | 80.03 | 50.32 | 62.87 | Leptin[2] | 1764.32 | 2112.24 | 119.72 |
| IL-1β | 51.76 | 192.52 | 371.97 | IP-10 | 1300.30 | 1119.80 | 86.12 |
| IL-2 | 13.27 | 3.63 | 27.33 | MMP-9 | 3405.05 | 2443.42 | 71.76 |
| IL-1ra | 26.01 | 4.29 | 16.50 | MMP-13 | 5.81 | 7.96 | 136.94 |
| IL-4 | 263.83 | 449.92 | 170.54 | PAI-1[B] | 381.16 | 307.44 | 80.66 |
| IL-5 | 52.10 | 109.08 | 209.37 | I-TAC | 610.84 | 524.00 | 85.78 |
| IL-6 | 237.79 | 874.22 | 367.65 | MMP-12 | 14.41 | 17.40 | 120.78 |
| IL-7 | 32.02 | 16.91 | 52.81 | HGF | 1109.68 | 967.32 | 87.17 |
| TGF-α | 48.84 | 13.25 | 27.13 | MMP-7 | 437.39 | 545.63 | 124.75 |
| Fractalkine | 16.93 | 4.02 | 23.75 | EGF | 447.62 | 505.26 | 112.88 |
| IL-8 | 1050.01 | 3114.51 | 296.62 | sCD40 ligand | 111.41 | 103.15 | 92.58 |
| IL-10 | 16.83 | 4.30 | 25.53 | MMP-8 | 55.11 | 265.37 | 481.49 |
| IL-15 | 34.44 | 7.08 | 20.56 | | | | |

FIG. 5C

| PERCENT CHANGE IN MEAN FLUORESCENCE INTENSITY IN THE MALE POPULATION ||||||||
|---|---|---|---|---|---|---|---|
| Biomarker | AST vs. NO | LC vs. NO | AST vs. LC | Biomarker | AST vs. NO | LC vs. NO | AST vs. LC |
| Adiponectin | 24.11 | 39.29 | -12.23 | IL-17 | 63.48 | 35.35 | 17.21 |
| Resistin | 123.24 | 104.49 | 8.40 | IL-1α | 279.04 |  | 66.51 |
| PAI-1[A] | 233.58 | 292.55 | -17.68 | IFN-γ | 30.48 | 33.66 | -2.44 |
| SE-selectin | -22.36 | -13.18 | -11.82 | G-CSF | 72.41 | 36.96 | 20.56 |
| sVCAM-1 | 55.23 | -23.61 | 50.79 | GM-CSF | 77.75 | 24.02 | 30.22 |
| sICAM-1 | 8.52 | -0.26 | 8.09 | TNF-α | 218.55 | 64.00 | 48.52 |
| MPO | 3467.91 | 2177.11 | 36.18 | MCP-1 | 1547.33 | 410.23 | 69.03 |
| CRP | 0.18 | 48.26 | -47.99 | IL-12 (p40) | 38.29 | 12.09 | 18.95 |
| SAA | 40.90 | 221.38 | -128.09 | MIP-1α | 429.75 | 36.79 | 74.18 |
| SAP | 16.82 | -22.18 | 33.38 | MIP-1β | 96.57 | 75.16 | 10.89 |
| Leptin[1] | -63.87 | -60.71 | -8.74 | VEGF | 49.91 | 16.29 | 22.42 |
| GLP-1 | -52.47 | 139.34 | -103.53 | IL-12(p70) | 385.11 | 451.75 | -13.74 |
| Amylin (Total) | -18.59 | 195.31 | -262.76 | IL-13 | -384539.50 | -538089.98 | -39.94 |
| C-Peptide | -6.67 | -32.90 | 28.10 | MMP-2 | -28.47 | 1.77 | -42.28 |
| Insulin | -17.76 | -43.75 | -74.78 | MMP-1 | 157.09 | 1681.05 | -592.77 |
| Sfas | 5.87 | 28.17 | -21.07 | MMP-3 | 0.72 | 37.01 | -36.03 |
| sFSI | 136.67 | 23.54 | 47.80 | Eotaxin | 379.44 | 540.73 | -33.64 |
| MIF | 532.08 | 578.78 | -7.39 | Leptin[2] | -63.99 | -41.62 | -62.13 |
| IL-1β | 140.10 | 24.29 | 48.24 | IP-10 | 112.35 | 218.42 | -49.95 |
| IL-2 | 0.73 | -12.80 | 13.44 | MMP-9 | 435.68 | 374.77 | 11.37 |
| IL-1ra | 17.94 | 33.04 | -12.81 | MMP-13 | -16.01 | 267.66 | -337.75 |
| IL-4 | 117.87 | 37.07 | 37.09 | PAI-1[B] | 2721.13 | 1969.94 | 26.63 |
| IL-5 | 189.94 | 55.89 | 46.23 | I-TAC | -4011.55 | -2982.15 | 26.32 |
| IL-6 | 507.08 | 96.10 | 67.70 | MMP-12 | 43.25 | 262.07 | -152.76 |
| IL-7 | 122.93 | 38.77 | 37.75 | HGF | -3019.71 | -2065.16 | 32.69 |
| TGF-α | 68.18 | 30.25 | 22.55 | MMP-7 | -50.98 | 129.70 | -368.60 |
| Fractalkine | 39.18 | 25.49 | 9.83 | EGF | 2392.73 | 2526.60 | -5.37 |
| IL-8 | 772.73 | 56.17 | 82.11 | sCD40 ligand | -33.54 | -22.74 | -16.25 |
| IL-10 | 42.52 | 45.16 | -1.85 | MMP-8 | -233.23 | -826.58 | -445.37 |
| IL-15 | 51.52 | 27.02 | 16.17 |  |  |  |  |

FIG. 5D

SIGNIFICANCE OF POPULATION DIFFERENCES EXPRESSED AS PROBABILITY OF STUDENT'S T VALUE FOR FEMALE POPULATIONS

| Biomarker | T AST vs. NO | T LC vs. NO | T AST vs. LC | Biomarker | T AST vs. NO | T LC vs. NO | T AST vs. LC |
|---|---|---|---|---|---|---|---|
| Adiponectin | 0.033 | 0.000 | 0.000 | IL-17 | 0.000 | 0.000 | 0.256 |
| Resistin | 0.000 | 0.000 | 0.157 | IL-1α | 0.001 | 0.369 | 0.035 |
| PAI-1[A] | 0.000 | 0.000 | 0.000 | IFN-γ | 0.000 | 0.000 | 0.042 |
| SE-selectin | 0.029 | 0.172 | 0.206 | G-CSF | 0.000 | 0.000 | 0.381 |
| sVCAM-1 | 0.000 | 0.000 | 0.000 | GM-CSF | 0.000 | 0.000 | 0.112 |
| sICAM-1 | 0.217 | 0.958 | 0.454 | TNF-α | 0.027 | 0.000 | 0.390 |
| MPO | 0.000 | 0.000 | 0.016 | MCP-1 | 0.012 | 0.000 | 0.213 |
| CRP | 0.986 | 0.000 | 0.000 | IL-12 (p40) | 0.000 | 0.000 | 0.302 |
| SAA | 0.116 | 0.000 | 0.000 | MIP-1α | 0.074 | 0.000 | 0.174 |
| SAP | 0.000 | 0.000 | 0.000 | MIP-1β | 0.000 | 0.000 | 0.157 |
| Leptin[1] | 0.000 | 0.000 | 0.695 | VEGF | 0.000 | 0.000 | 0.519 |
| GLP-1 | 0.022 | 0.131 | 0.056 | IL-12(p70) | 0.000 | 0.000 | 0.207 |
| Amylin (Total) | 0.353 | 0.003 | 0.003 | IL-13 | 0.000 | 0.000 | 0.079 |
| C-Peptide | 0.234 | 0.000 | 0.003 | MMP-2 | 0.479 | 0.946 | 0.626 |
| Insulin | 0.378 | 0.070 | 0.012 | MMP-1 | 0.000 | 0.000 | 0.000 |
| Sfas | 0.892 | 0.227 | 0.000 | MMP-3 | 0.912 | 0.000 | 0.000 |
| sFSI | 0.000 | 0.484 | 0.149 | Eotaxin | 0.000 | 0.000 | 0.002 |
| MIF | 0.000 | 0.000 | 0.795 | Leptin[2] | 0.000 | 0.000 | 0.147 |
| IL-1β | 0.044 | 0.000 | 0.199 | IP-10 | 0.000 | 0.000 | 0.000 |
| IL-2 | 0.989 | 0.653 | 0.371 | MMP-9 | 0.000 | 0.000 | 0.530 |
| IL-1ra | 0.206 | 0.000 | 0.000 | MMP-13 | 0.608 | 0.299 | 0.309 |
| IL-4 | 0.000 | 0.017 | 0.317 | PAI-1[B] | 0.000 | 0.000 | 0.002 |
| IL-5 | 0.000 | 0.005 | 0.211 | I-TAC | 0.000 | 0.000 | 0.008 |
| IL-6 | 0.004 | 0.001 | 0.086 | MMP-12 | 0.105 | 0.097 | 0.229 |
| IL-7 | 0.000 | 0.000 | 0.114 | HGF | 0.000 | 0.000 | 0.000 |
| TGF-α | 0.000 | 0.000 | 0.547 | MMP-7 | 0.000 | 0.000 | 0.000 |
| Fractalkine | 0.000 | 0.000 | 0.869 | EGF | 0.000 | 0.000 | 0.615 |
| IL-8 | 0.000 | 0.018 | 0.019 | sCD40 ligand | 0.402 | 0.418 | 0.155 |
| IL-10 | 0.000 | 0.000 | 0.001 | MMP-8 | 0.000 | 0.000 | 0.007 |
| IL-15 | 0.000 | 0.000 | 0.057 | | | | |

FIG. 5E

| COMPARISON OF PERCENT CHANGE IN MEAN FLUORESCENCE INTENSITY IN MALE AND FEMALE POPULATIONS |||||||
|---|---|---|---|---|---|---|
| Biomarker | AST men vs. women | LC men vs. women | NO men vs. women | Biomarker | AST men vs. women | LC men vs. women | NO men vs. women |
| Adiponectin | 0.10 | -18.14 | -10.90 | IL-17 | 30.64 | 3.96 | 19.90 |
| Resistin | -33.23 | 23.07 | 58.99 | IL-1α | 140.22 | 30.08 | -20.27 |
| PAI-1[A] | -15.46 | 23.16 | 134.12 | IFN-γ | -2.75 | -5.75 | 28.62 |
| SE-selectin | 3.83 | 8.93 | 52.93 | G-CSF | 80.57 | 7.77 | 18.99 |
| sVCAM-1 | 16.18 | -6.32 | -9.00 | GM-CSF | 69.08 | 1.12 | 14.94 |
| sICAM-1 | 10.07 | -0.30 | 12.53 | TNF-α | 155.04 | -49.29 | 56.20 |
| MPO | -16.10 | -2.85 | 1230.91 | MCP-1 | 79.54 | 7.27 | 61.07 |
| CRP | -22.08 | 7.21 | -15.82 | IL-12 (p40) | 37.24 | 2.10 | 16.05 |
| SAA | -8.51 | 22.59 | -27.43 | MIP-1α | 281.59 | -30.18 | 45.91 |
| SAP | 14.39 | 4.87 | 3.14 | MIP-1β | 52.27 | -28.41 | 57.17 |
| Leptin[1] | -72.48 | -32.39 | -72.76 | VEGF | 43.04 | 7.55 | 13.44 |
| GLP-1 | -82.09 | 23.23 | -6.65 | IL-12(p70) | 20.55 | -28.63 | 4.52 |
| Amylin (Total) | -72.43 | 49.59 | 26.27 | IL-13 | -7.67 | -3.21 | -36841.43 |
| C-Peptide | -17.03 | 7.58 | -22.79 | MMP-2 | -44.02 | 26.80 | -24.04 |
| Insulin | -57.45 | 14.56 | 6.48 | MMP-1 | -51.13 | 34.73 | 301.06 |
| Sfas | -34.05 | 8.59 | 16.69 | MMP-3 | -0.63 | 8.24 | 22.90 |
| sFSI | 46.15 | 50.64 | -18.92 | Eotaxin | -9.80 | 0.20 | 127.46 |
| MIF | 58.30 | 55.98 | 735.03 | Leptin[2] | -69.94 | -27.28 | -55.72 |
| IL-1β | 117.39 | -3.26 | 23.55 | IP-10 | -23.43 | 19.53 | -26.09 |
| IL-2 | 6.47 | -4.51 | -16.22 | MMP-9 | -24.71 | -11.86 | 169.56 |
| IL-1ra | -1.56 | -0.52 | 11.01 | MMP-13 | -49.86 | 118.12 | 103.36 |
| IL-4 | 78.82 | 27.65 | -13.02 | PAI-1[B] | -25.60 | 14.26 | 390.15 |
| IL-5 | 87.95 | 26.47 | 5.34 | I-TAC | -31.43 | 16.14 | -694.81 |
| IL-6 | 241.21 | 8.89 | 10.90 | MMP-12 | -41.95 | 46.11 | 54.62 |
| IL-7 | 76.56 | -37.27 | 23.96 | HGF | -28.37 | 39.00 | -1517.50 |
| TGF-α | 52.28 | 2.33 | 19.67 | MMP-7 | -15.42 | -3.46 | 30.36 |
| Fractalkine | 10.96 | -0.26 | 22.99 | EGF | 10.50 | 11.68 | 170.40 |
| IL-8 | 49.10 | 48.14 | 234.11 | sCD40 ligand | -47.84 | 29.97 | -16.57 |
| IL-10 | 12.51 | -36.60 | 25.00 | MMP-8 | -71.41 | 21.38 | -637.74 |
| IL-15 | 52.75 | -0.16 | 18.67 | | | | |

FIG. 6A

SIGNIFICANCE OF MALE AND FEMALE POPULATION DIFFERENCES EXPRESSED AS PROBABILITY OF STUDENT'S T VALUE

| Biomarker | T AST men vs. women | T LC men vs. women | T NO men vs. women | Biomarker | T AST men vs. women | T LC men vs. women | T NO men vs. women |
|---|---|---|---|---|---|---|---|
| Adiponectin | 0.991 | 0.004 | 0.150 | IL-17 | 0.000 | 0.599 | 0.000 |
| Resistin | 0.040 | 0.014 | 0.000 | IL-1α | 0.042 | 0.495 | 0.340 |
| PAI-1[A] | 0.001 | 0.000 | 0.000 | IFN-γ | 0.431 | 0.135 | 0.000 |
| SE-selectin | 0.729 | 0.501 | 0.000 | G-CSF | 0.000 | 0.322 | 0.000 |
| sVCAM-1 | 0.011 | 0.132 | 0.007 | GM-CSF | 0.000 | 0.746 | 0.007 |
| sICAM-1 | 0.130 | 0.954 | 0.037 | TNF-α | 0.107 | 0.171 | 0.000 |
| MPO | 0.082 | 0.774 | 0.000 | MCP-1 | 0.380 | 0.594 | 0.000 |
| CRP | 0.005 | 0.150 | 0.059 | IL-12 (p40) | 0.000 | 0.556 | 0.000 |
| SAA | 0.603 | 0.056 | 0.156 | MIP-1α | 0.181 | 0.066 | 0.000 |
| SAP | 0.001 | 0.448 | 0.319 | MIP-1β | 0.021 | 0.199 | 0.000 |
| Leptin[1] | 0.000 | 0.003 | 0.000 | VEGF | 0.000 | 0.107 | 0.000 |
| GLP-1 | 0.113 | 0.743 | 0.754 | IL-12(p70) | 0.463 | 0.112 | 0.938 |
| Amylin (Total) | 0.080 | 0.284 | 0.409 | IL-13 | 0.675 | 0.824 | 0.000 |
| C-Peptide | 0.014 | 0.402 | 0.000 | MMP-2 | 0.010 | 0.305 | 0.427 |
| Insulin | 0.101 | 0.577 | 0.731 | MMP-1 | 0.005 | 0.016 | 0.000 |
| Sfas | 0.000 | 0.235 | 0.607 | MMP-3 | 0.929 | 0.072 | 0.000 |
| sFSI | 0.100 | 0.303 | 0.123 | Eotaxin | 0.378 | 0.980 | 0.000 |
| MIF | 0.017 | 0.080 | 0.000 | Leptin[2] | 0.000 | 0.004 | 0.000 |
| IL-1β | 0.126 | 0.065 | 0.000 | IP-10 | 0.030 | 0.042 | 0.103 |
| IL-2 | 0.124 | 0.418 | 0.686 | MMP-9 | 0.007 | 0.172 | 0.000 |
| IL-1ra | 0.610 | 0.883 | 0.295 | MMP-13 | 0.334 | 0.522 | 0.094 |
| IL-4 | 0.018 | 0.140 | 0.068 | PAI-1[B] | 0.018 | 0.126 | 0.000 |
| IL-5 | 0.036 | 0.233 | 0.663 | I-TAC | 0.004 | 0.080 | 0.000 |
| IL-6 | 0.048 | 0.766 | 0.529 | MMP-12 | 0.114 | 0.549 | 0.097 |
| IL-7 | 0.000 | 0.157 | 0.000 | HGF | 0.002 | 0.019 | 0.000 |
| TGF-α | 0.000 | 0.549 | 0.000 | MMP-7 | 0.298 | 0.580 | 0.000 |
| Fractalkine | 0.001 | 0.936 | 0.000 | EGF | 0.512 | 0.348 | 0.000 |
| IL-8 | 0.340 | 0.060 | 0.000 | sCD40 ligand | 0.010 | 0.474 | 0.593 |
| IL-10 | 0.004 | 0.069 | 0.000 | MMP-8 | 0.319 | 0.346 | 0.000 |
| IL-15 | 0.000 | 0.954 | 0.000 | | | | |

FIG. 6B

PERCENT CHANGE IN MEAN CONCENTRATION IN THE FEMALE POPULATION

| Biomarker | LC vs. NO | AST vs. NO | AST vs. LC | Scalar Sum | Biomarker | LC vs. NO | AST vs. NO | AST vs. LC | Scalar Sum |
|---|---|---|---|---|---|---|---|---|---|
| I-TAC | 232.54 | 808.32 | 63.39 | 1104.24 | MMP-1 | 211.09 | -0.40 | -212.35 | 423.84 |
| PAI-1 | 236.98 | 331.62 | 21.93 | 590.52 | Fractalkine | -19.66 | -80.00 | -301.66 | 401.32 |
| MMP-7 | 84.44 | -63.12 | -400.06 | 547.62 | IL-1α | 71.64 | 260.31 | 52.36 | 384.32 |
| MMP-3 | 296.73 | 24.09 | -219.71 | 540.53 | CRP | 212.05 | 85.24 | -68.45 | 365.74 |
| IL-8 | -82.05 | 205.35 | 94.12 | 381.53 | MIP-1β | -94.59 | -97.96 | -164.40 | 356.96 |
| MPO | 146.60 | 208.72 | 20.12 | 375.44 | IP-10 | 137.95 | 151.54 | 5.40 | 294.88 |
| Leptin | 66.76 | 199.02 | 44.23 | 310.02 | IL-1ra | -99.93 | -99.96 | -67.00 | 266.89 |
| sFSI | -11.14 | 188.58 | 69.21 | 268.93 | MIP-1α | -85.14 | 90.57 | -57.53 | 233.24 |
| HGF | -25.19 | 161.40 | 71.38 | 257.97 | VEGF | -97.45 | -97.90 | -21.17 | 216.52 |
| Resistin | 5.74 | 110.38 | 49.74 | 165.86 | IFN-γ | 69.14 | 100.91 | 15.81 | 185.87 |
| C-Peptide | -34.06 | 58.58 | 58.42 | 151.06 | Adiponectin | 90.42 | 79.52 | -6.07 | 176.01 |
| MMP-13 | -33.46 | -57.79 | -57.65 | 148.91 | Eotaxin | 79.43 | 65.79 | -8.23 | 153.45 |
| SAP | -37.39 | -58.12 | -49.49 | 145.01 | IL-6 | 31.65 | 52.43 | 13.63 | 97.71 |
| sVCAM-1 | -14.50 | 30.75 | 34.61 | 79.87 | MMP-12 | 49.48 | 5.90 | -41.14 | 96.52 |
| MMP-8 | -6.98 | -3.33 | 3.78 | 14.08 | sICAM-1 | 19.75 | -13.48 | -38.41 | 71.64 |
| IL-10 | 607.39 | -88.77 | -6198.42 | 6894.58 | MIF | -33.32 | -32.99 | 0.49 | 66.79 |
| MMP-9 | 1467.27 | 3385.22 | 55.03 | 4907.52 | Sfas | 22.05 | 18.36 | -3.12 | 43.53 |
| G-CSF | 793.53 | 263.78 | -145.62 | 1202.93 | IL-12 (p40) | 75.26 | 219.85 | 45.21 | 340.31 |
| EGF | 627.08 | 408.97 | -42.85 | 1078.90 | IL-4 | -37.26 | 26.12 | 50.25 | 113.63 |
| MCP-1 | 477.55 | 324.18 | -36.16 | 837.89 | Insulin | -42.14 | -18.85 | 28.70 | 89.70 |
| SAA | 453.90 | 100.01 | -176.94 | 730.85 | | | | | |

FIG. 7A

SIGNIFICANCE OF POPULATION DIFFERENCES EXPRESSED AS PROBABILITY OF KRUKSAL-WALLIS FOR FEMALE PULATIONS

| Biomarker | LC vs. NO | AST vs. NO | AST vs. LC | Biomarker | LC vs. NO | AST vs. NO | AST vs. LC |
|---|---|---|---|---|---|---|---|
| I-TAC | 1.31E-19 | 2.50E-30 | 1.19E-11 | MMP-1 | 1.81E-13 | 0.143 | 7.91E-13 |
| PAI-1 | 1.01E-17 | 1.64E-21 | 0.030 | Fractalkine | 2.82E-49 | 0.391 | 0.008 |
| MMP-7 | 1.04E-12 | 9.55E-23 | 2.83E-29 | IL-1α | 0.218 | 1.67E-05 | 5.81E-04 |
| MMP-3 | 0.041 | 9.37E-07 | 2.16E-06 | CRP | 8.76E-47 | 1.78E-07 | 0.253 |
| IL-8 | 4.82E-32 | 0.004 | 0.004 | MIP-1β | 0.027 | 0.812 | 0.004 |
| MPO | 5.92E-36 | 3.36E-14 | 0.004 | IP-10 | 1.05E-19 | 4.53E-20 | 0.754 |
| Leptin | 1.48E-15 | 1.02E-15 | 4.03E-09 | IL-1ra | 2.09E-55 | 1.35E-09 | 0.332 |
| sFSI | 7.36E-35 | 1.77E-11 | 1.23E-19 | MIP-1α | 0.004 | 1.29E-04 | 0.238 |
| HGF | 0.001 | 7.52E-15 | 1.52E-19 | VEGF | 1.43E-05 | 6.72E-04 | 0.314 |
| Resistin | 8.18E-14 | 1.19E-12 | 3.57E-10 | IFN-γ | 3.77E-05 | 3.77E-05 | 0.638 |
| C-Peptide | 7.34E-40 | 0.004 | 4.76E-10 | Adiponectin | 2.00E-42 | 1.08E-11 | 0.316 |
| MMP-13 | 0.024 | 9.50E-08 | 1.11E-05 | Eotaxin | 3.41E-09 | 1.59E-09 | 0.313 |
| SAP | 8.57E-42 | 6.46E-07 | 0.031 | IL-6 | 1.94E-32 | 0.009 | 0.225 |
| sVCAM-1 | 6.40E-03 | 5.43E-07 | 2.43E-13 | MMP-12 | 2.05E-05 | 0.528 | 4.44E-05 |
| MMP-8 | 0.015 | 2.79E-04 | 1.12E-11 | sICAM-1 | 5.58E-44 | 0.009 | 0.184 |
| IL-10 | 3.35E-38 | 0.251 | 8.52E-06 | MIF | 1.16E-46 | 9.67E-04 | 0.109 |
| MMP-9 | 2.57E-13 | 2.35E-13 | 0.704 | Sfas | 8.55E-28 | 1.32E-07 | 0.708 |
| G-CSF | 2.31E-05 | 3.38E-04 | 0.363 | IL-12 (p40) | 0.19 | 0.077 | 0.002 |
| EGF | 1.43E-24 | 2.10E-24 | 0.298 | IL-4 | 0.252 | 0.003 | 0.071 |
| MCP-1 | 5.11E-19 | 6.55E-22 | 0.361 | Insulin | 1.73E-25 | 0.753 | 0.145 |
| SAA | 3.15E-40 | 4.84E-14 | 0.093 | | | | |

FIG. 7B

PERCENT CHANGE IN MEAN CONCENTRATION IN THE MALE POPULATION

| Biomarker | LC vs. NO | AST vs. NO | AST vs. LC | Scalar Sum | Biomarker | LC vs. NO | AST vs. NO | AST vs. LC | Scalar Sum |
|---|---|---|---|---|---|---|---|---|---|
| HGF | 31570.67 | 70709.80 | 55.27 | 102335.75 | MIP-1α | 167.51 | 556.86 | 59.27 | 783.64 |
| MMP-8 | 24387.41 | 3673.65 | -548.91 | 28609.97 | MMP-13 | 253.63 | 75.96 | -100.97 | 430.56 |
| I-TAC | 5284.92 | 20195.93 | 73.47 | 25554.31 | G-CSF | 218.18 | 11.35 | -185.74 | 415.28 |
| EGF | 3182.66 | 3895.15 | 17.83 | 7095.65 | IFN-γ | 66.22 | -57.48 | -290.89 | 414.58 |
| PAI-1 | 1766.61 | 2974.80 | 39.29 | 4780.71 | MMP-7 | 161.73 | -3.44 | -171.06 | 336.23 |
| MMP-1 | 2657.85 | 496.02 | -362.71 | 3516.58 | IP-10 | 165.05 | 158.57 | -2.51 | 326.13 |
| MPO | 858.94 | 1804.89 | 49.66 | 2713.49 | CRP | 81.49 | -35.15 | -179.84 | 296.48 |
| MIF | 687.69 | 491.62 | -33.14 | 1212.44 | Insulin | -24.90 | -56.95 | -74.46 | 156.32 |
| Eotaxin | 365.15 | 522.18 | 25.24 | 912.57 | VEGF | 72.02 | 51.88 | -13.26 | 137.15 |
| MMP-12 | 399.62 | 158.80 | -93.05 | 651.48 | SAP | -39.69 | -53.58 | -29.91 | 123.18 |
| SSA | 49.02 | -62.23 | -294.54 | 405.78 | Adiponectin | 43.04 | -9.06 | -57.29 | 109.39 |
| Resistin | 90.46 | 29.15 | -47.46 | 167.07 | sVCAM-1 | -15.22 | 16.68 | 27.34 | 59.24 |
| sFSI | -0.87 | 78.86 | 44.58 | 124.31 | Sfas | 13.76 | 6.21 | -7.11 | 27.08 |
| Leptin | -51.27 | -49.51 | 3.49 | 104.26 | IL-1ra | 24.34 | -42.18 | -115.05 | 181.57 |
| C-Peptide | -7.14 | 29.77 | 28.45 | 65.36 | IL-12 (p40) | -72.67 | 4.72 | 73.90 | 151.30 |
| MMP-9 | 10857.07 | 1705.79 | -506.77 | 13069.63 | MIP-1β | 4.75 | 64.53 | 36.34 | 105.61 |
| MCP-1 | 235.25 | 829.77 | 63.94 | 1128.96 | sICAM-1 | 9.18 | -31.45 | -59.29 | 99.93 |
| MMP-3 | 515.02 | 216.75 | -94.17 | 825.93 | | | | | |

FIG. 8A

SIGNIFICANCE OF POPULATION DIFFERENCES EXPRESSED AS PROBABILITY OF KRUKSAL-WALLIS MEANS VALUE FOR MALE POPULATIONS

| Biomarker | LC vs. NO | AST vs. NO | AST vs. LC | Biomarker | LC vs. NO | AST vs. NO | AST vs. LC |
|---|---|---|---|---|---|---|---|
| HGF | 5.68718E-58 | 1.25E-44 | 1.44E-10 | MIP-1α | 1.23E-09 | 9.06E-04 | 0.582 |
| MMP-8 | 7.13597E-36 | 0.003 | 4.08E-13 | MMP-13 | 4.07E-12 | 0.002 | 0.377 |
| I-TAC | 1.904E-63 | 1.22E-44 | 3.22E-08 | G-CSF | 0.119 | 0.002 | 6.22E-05 |
| EGF | 4.54971E-61 | 3.00E-31 | 0.006 | IFN-γ | 0.992 | 0.014 | 0.018 |
| PAI-1 | 9.65123E-52 | 3.91E-32 | 0.032 | MMP-7 | 2.98033E-28 | 0.213 | 4.52E-18 |
| MMP-1 | 2.591E-52 | 1.34E-09 | 2.27E-16 | IP-10 | 1.04E-31 | 1.87E-18 | 0.725 |
| MPO | 3.30E-47 | 3.03E-32 | 4.17E-11 | CRP | 1.04E-11 | 0.758 | 1.87E-9 |
| MIF | 3.05E-27 | 2.20E-29 | 0.006 | Insulin | 4.18E-04 | 3.54E-05 | 0.219 |
| Eotaxin | 2.54E-43 | 5.55E-28 | 0.001 | VEGF | 6.046E-13 | 2.61E-09 | 0.699 |
| MMP-12 | 7.21087E-32 | 1.39E-04 | 0.002 | SAP | 3.20E-07 | 1.22E-05 | 0.739 |
| SAA | 4.51E-19 | 0.002 | 1.23E-06 | Adiponectin | 6.95E-11 | 0.285 | 4.39E-08 |
| Resistin | 5.26E-16 | 0.011 | 3.40E-04 | sVCAM-1 | 0.674 | 9.79E-10 | 1.45E-15 |
| sFSI | 3.39E-21 | 0.019 | 3.88E-17 | Sfas | 2.65E-15 | 4.94E-08 | 0.245 |
| Leptin | 1.08E-10 | 0.013 | 8.32E-04 | IL-1ra | 6.40E-09 | 0.088 | 0.009 |
| C-Peptide | 9.13E-11 | 1.72E-02 | 1.07E-08 | IL-12 (p40) | 0.001 | 0.335 | 0.180 |
| MMP-9 | 6.48556E-33 | 4.61E-20 | 0.759 | MIP-1β | 3.79E-05 | 0.066 | 0.434 |
| MCP-1 | 2.78E-39 | 3.91E-21 | 0.186 | SICAM-1 | 0.723 | 2.17E-05 | 0.218 |
| MMP-3 | 5.09E-15 | 2.29E-05 | 0.170 | | | | |

FIG. 8B

```
                        SEQUENCE LISTING

<160> NUMBER OF SEQ ID NOS: 17

<210> SEQ ID NO 1
    <211> LENGTH: 319
    <212> TYPE: PRT
    <213> ORGANISM: Homo sapiens

<400> SEQUENCE: 1

Met Val Leu Ser Glu Leu Ala Ala Arg Leu Asn Cys Ala Glu Tyr Lys
    1               5                   10                  15

Asn Trp Val Lys Ala Gly His Cys Leu Leu Leu Leu Arg Ser Cys Leu
                    20                  25                  30

Gln Gly Phe Val Gly Arg Glu Val Leu Ser Phe His Arg Gly Leu Leu
                35                  40                  45

Ala Ala Ala Pro Gly Leu Gly Pro Arg Ala Val Cys Arg Gly Gly Ser
        50                  55                  60

Arg Cys Ser Pro Arg Ala Arg Gln Phe Gln Pro Gln Cys Gln Val Cys
    65                  70                  75                  80

Ala Glu Trp Lys Arg Glu Ile Leu Arg His His Val Asn Arg Asn Gly
                    85                  90                  95

Asp Val His Trp Gly Asn Cys Arg Pro Gly Arg Trp Pro Val Asp Ala
                    100                 105                 110

Trp Glu Val Ala Lys Ala Phe Met Pro Arg Gly Leu Ala Asp Lys Gln
                115                 120                 125

Gly Pro Glu Glu Cys Asp Ala Val Ala Leu Leu Ser Leu Ile Asn Ser
        130                 135                 140

Cys Asp His Phe Val Val Asp Arg Lys Lys Val Thr Glu Val Ile Lys
    145                 150                 155                 160

Cys Arg Asn Glu Ile Met His Ser Ser Glu Met Lys Val Ser Ser Thr
```

```
              165                 170                 175
Trp Leu Arg Asp Phe Gln Met Lys Ile Gln Asn Phe Leu Asn Glu Phe
            180                 185                 190

Lys Asn Ile Pro Glu Ile Val Ala Val Tyr Ser Arg Ile Glu Gln Leu
        195                 200                 205

Leu Thr Ser Asp Trp Ala Val His Ile Pro Glu Glu Asp Gln Arg Asp
    210                 215                 220

Gly Cys Glu Cys Glu Met Gly Thr Tyr Leu Ser Glu Ser Gln Val Asn
225                 230                 235                 240

Glu Ile Glu Met Gln Leu Leu Lys Glu Lys Leu Gln Glu Ile Tyr Leu
                245                 250                 255

Gln Ala Glu Glu Gln Glu Val Leu Pro Glu Glu Leu Ser Asn Arg Leu
            260                 265                 270

Glu Val Val Lys Glu Phe Leu Arg Asn Asn Glu Asp Leu Arg Asn Gly
        275                 280                 285

Leu Thr Glu Asp Met Gln Lys Leu Asp Ser Leu Cys Leu His Gln Lys
    290                 295                 300

Leu Asp Ser Gln Glu Pro Gly Arg Gln Thr Pro Asp Arg Lys Ala
305                 310                 315
```

<210> SEQ ID NO 2
<211> LENGTH: 57
<212> TYPE: PRT
<213> ORGANISM: Homo sapiens

<400> SEQUENCE: 2

```
Met Ser Cys Leu Met Val Glu Arg Cys Gly Glu Ile Leu Phe Glu Asn
1               5                   10                  15

Pro Asp Gln Asn Ala Lys Cys Val Cys Met Leu Gly Asp Ile Arg Leu
            20                  25                  30

Arg Gly Gln Thr Gly Val Arg Ala Glu Arg Arg Gly Ser Tyr Pro Phe
        35                  40                  45

Ile Asp Phe Arg Leu Leu Asn Ser Glu
    50                  55
```

<210> SEQ ID NO 3
<211> LENGTH: 62
<212> TYPE: PRT
<213> ORGANISM: Homo sapiens

<400> SEQUENCE: 3

```
Met Ile Arg Ser Lys Phe Arg Val Pro Arg Ile Leu His Val Leu Ser
1               5                   10                  15

Ala His Ser Gln Ala Ser Asp Lys Asn Phe Thr Ala Glu Asn Ser Glu
            20                  25                  30

Val Val Val Ser Ser Arg Thr Asp Val Ser Pro Met Lys Ser Asp Leu
        35                  40                  45

Leu Leu Pro Pro Ser Lys Pro Gly Cys Asn Asn Val Leu Asn
    50                  55                  60
```

<210> SEQ ID NO 4
<211> LENGTH: 146
<212> TYPE: PRT
<213> ORGANISM: Homo sapiens

<400> SEQUENCE: 4

```
Met Val Gln Gly Met Cys Ser Pro Ser Pro Phe Gly Thr Ser Arg Ala
1               5                   10                  15
```

```
Cys Thr Val Gly Thr Gln Val Asp Ser Arg Ser Leu Pro Trp Ala Leu
             20                  25                  30

Gly Ala Ser Ala Gln Arg Gly Asn Ile Pro Thr Ala Thr Cys Ala Arg
         35                  40                  45

Thr Ala Gly Thr Leu Arg Arg Gly Leu Gln Pro Gly Trp Gly Trp Glu
     50                  55                  60

Asp Phe Leu Asp Glu Gly Gln Pro Gly Phe Ser Ser Arg Met Ser Trp
 65                  70                  75                  80

Ser Arg Pro Pro Ala Gln Glu Gln Gly Ala Arg Gly Pro Ser Trp
             85                  90                  95

Val Arg Gly Leu Gly Gln Pro Thr Ala Ala Phe Glu Gln Gly Pro Arg
             100                 105                 110

Ser Ser Val Ser Pro Gln Trp Glu Gly Gly Gln Gly Pro Gly Glu
             115                 120                 125

Leu Gly Arg Lys His Leu Leu Gly Pro Ser Gln His Pro Thr Asp
         130                 135                 140

Arg His
145

<210> SEQ ID NO 5
<211> LENGTH: 1039
<212> TYPE: PRT
<213> ORGANISM: Homo sapiens

<400> SEQUENCE: 5

Met Ala Val Gln Leu Val Pro Asp Ser Ala Leu Gly Leu Leu Met Met
 1               5                  10                  15

Thr Glu Gly Arg Arg Cys Gln Val His Leu Leu Asp Asp Arg Lys Leu
             20                  25                  30

Glu Leu Leu Val Gln Pro Lys Leu Leu Ala Lys Glu Leu Leu Asp Leu
         35                  40                  45

Val Ala Ser His Phe Asn Leu Lys Glu Lys Glu Tyr Phe Gly Ile Ala
     50                  55                  60

Phe Thr Asp Glu Thr Gly His Leu Asn Trp Leu Gln Leu Asp Arg Arg
 65                  70                  75                  80

Val Leu Glu His Asp Phe Pro Lys Lys Ser Gly Pro Val Val Leu Tyr
             85                  90                  95

Phe Cys Val Arg Phe Tyr Ile Glu Ser Ile Ser Tyr Leu Lys Asp Asn
             100                 105                 110

Ala Thr Ile Glu Leu Phe Phe Leu Asn Ala Lys Ser Cys Ile Tyr Lys
         115                 120                 125

Glu Leu Ile Asp Val Asp Ser Glu Val Val Phe Glu Leu Ala Ser Tyr
     130                 135                 140

Ile Leu Gln Glu Ala Lys Gly Asp Phe Ser Ser Asn Glu Val Val Arg
145                 150                 155                 160

Ser Asp Leu Lys Lys Leu Pro Ala Leu Pro Thr Gln Ala Leu Lys Glu
             165                 170                 175

His Pro Ser Leu Ala Tyr Cys Glu Asp Arg Val Ile Glu His Tyr Lys
         180                 185                 190

Lys Leu Asn Gly Gln Thr Arg Gly Gln Ala Ile Val Asn Tyr Met Ser
     195                 200                 205

Ile Val Glu Ser Leu Pro Thr Tyr Gly Val His Tyr Tyr Ala Val Lys
 210                 215                 220

Asp Lys Gln Gly Ile Pro Trp Trp Leu Gly Leu Ser Tyr Lys Gly Ile
```

-continued

```
            225                 230                 235                 240
        Phe Gln Tyr Asp Tyr His Asp Lys Val Lys Pro Arg Lys Ile Phe Gln
                        245                 250                 255

Trp Arg Gln Leu Glu Asn Leu Tyr Phe Arg Glu Lys Lys Phe Ser Val
                        260                 265                 270

Glu Val His Asp Pro Arg Arg Ala Ser Val Thr Arg Thr Phe Gly
                        275                 280                 285

His Ser Gly Ile Ala Val His Thr Trp Tyr Ala Cys Pro Ala Leu Ile
                        290                 295                 300

Lys Ser Ile Trp Ala Met Ala Ile Ser Gln His Gln Phe Tyr Leu Asp
        305                 310                 315                 320

Arg Lys Gln Ser Lys Ser Lys Ile His Ala Ala Arg Ser Leu Ser Glu
                        325                 330                 335

Ile Ala Ile Asp Leu Thr Glu Thr Gly Thr Leu Lys Thr Ser Lys Leu
                        340                 345                 350

Ala Asn Met Gly Ser Lys Gly Lys Ile Ile Ser Gly Ser Ser Gly Ser
                        355                 360                 365

Leu Leu Ser Ser Gly Ser Gln Glu Ser Asp Ser Ser Gln Ser Ala Lys
                        370                 375                 380

Lys Asp Met Leu Ala Ala Leu Lys Ser Arg Gln Glu Ala Leu Glu Glu
        385                 390                 395                 400

Thr Leu Arg Gln Arg Leu Glu Glu Leu Lys Lys Leu Cys Leu Arg Glu
                        405                 410                 415

Ala Glu Leu Thr Gly Lys Leu Pro Val Glu Tyr Pro Leu Asp Pro Gly
                        420                 425                 430

Glu Glu Pro Pro Ile Val Arg Arg Ile Gly Thr Ala Phe Lys Leu
                        435                 440                 445

Asp Glu Gln Lys Ile Leu Pro Lys Gly Glu Glu Ala Glu Leu Glu Arg
                        450                 455                 460

Leu Glu Arg Glu Phe Ala Ile Gln Ser Gln Ile Thr Glu Ala Ala Arg
        465                 470                 475                 480

Arg Leu Ala Ser Asp Pro Asn Val Ser Lys Lys Leu Lys Lys Gln Arg
                        485                 490                 495

Lys Thr Ser Tyr Leu Asn Ala Leu Lys Lys Leu Gln Glu Ile Glu Asn
                        500                 505                 510

Ala Ile Asn Glu Asn Arg Ile Lys Ser Gly Lys Lys Pro Thr Gln Arg
                        515                 520                 525

Ala Ser Leu Ile Ile Asp Asp Gly Asn Ile Ala Ser Glu Asp Ser Ser
                        530                 535                 540

Leu Ser Asp Ala Leu Val Leu Glu Asp Glu Asp Ser Gln Val Thr Ser
        545                 550                 555                 560

Thr Ile Ser Pro Leu His Ser Pro His Lys Gly Leu Pro Pro Arg Pro
                        565                 570                 575

Pro Ser His Asn Arg Pro Pro Pro Gln Ser Leu Glu Gly Leu Arg
                        580                 585                 590

Gln Met His Tyr His Arg Asn Asp Tyr Asp Lys Ser Pro Ile Lys Pro
                        595                 600                 605

Lys Met Trp Ser Glu Ser Leu Asp Glu Pro Tyr Glu Lys Val Lys
                        610                 615                 620

Lys Arg Ser Ser His Ser His Ser Ser His Lys Arg Phe Pro Ser
        625                 630                 635                 640

Thr Gly Ser Cys Ala Glu Ala Gly Gly Gly Ser Asn Ser Leu Gln Asn
                        645                 650                 655
```

Ser Pro Ile Arg Gly Leu Pro His Trp Asn Ser Gln Ser Ser Met Pro
            660                 665                 670

Ser Thr Pro Asp Leu Arg Val Arg Ser Pro His Tyr Val His Ser Thr
        675                 680                 685

Arg Ser Val Asp Ile Ser Pro Thr Arg Leu His Ser Leu Ala Leu His
    690                 695                 700

Phe Arg His Arg Ser Ser Leu Glu Ser Gln Gly Lys Leu Leu Gly
705                 710                 715                 720

Ser Glu Asn Asp Thr Gly Ser Pro Asp Phe Tyr Thr Pro Arg Thr Arg
                725                 730                 735

Ser Ser Asn Gly Ser Asp Pro Met Asp Asp Cys Ser Ser Cys Thr Ser
            740                 745                 750

His Ser Ser Ser Glu His Tyr Tyr Pro Ala Gln Met Asn Ala Asn Tyr
        755                 760                 765

Ser Thr Leu Ala Glu Asp Ser Pro Ser Lys Ala Arg Gln Arg Gln Arg
    770                 775                 780

Gln Arg Gln Arg Ala Ala Gly Ala Leu Gly Ser Ala Ser Ser Gly Ser
785                 790                 795                 800

Met Pro Asn Leu Ala Ala Arg Gly Gly Ala Gly Ala Gly Ala
                805                 810                 815

Gly Gly Gly Val Tyr Leu His Ser Gln Ser Gln Pro Ser Ser Gln Tyr
        820                 825                 830

Arg Ile Lys Glu Tyr Pro Leu Tyr Ile Glu Gly Gly Ala Thr Pro Val
    835                 840                 845

Val Val Arg Ser Leu Glu Ser Asp Gln Glu Gly His Tyr Ser Val Lys
850                 855                 860

Ala Gln Phe Lys Thr Ser Asn Ser Tyr Thr Ala Gly Leu Phe Lys
865                 870                 875                 880

Glu Ser Trp Arg Gly Gly Gly Asp Glu Gly Asp Thr Gly Arg Leu
                885                 890                 895

Thr Pro Ser Arg Ser Gln Ile Leu Arg Thr Pro Ser Leu Gly Arg Glu
            900                 905                 910

Gly Ala His Asp Lys Gly Ala Gly Arg Ala Ala Val Ser Asp Glu Leu
        915                 920                 925

Arg Gln Trp Tyr Gln Arg Ser Thr Ala Ser His Lys Glu His Ser Arg
    930                 935                 940

Leu Ser His Thr Ser Ser Thr Ser Ser Asp Ser Gly Ser Gln Tyr Ser
945                 950                 955                 960

Thr Ser Ser Gln Ser Thr Phe Val Ala His Ser Arg Val Thr Arg Met
                965                 970                 975

Pro Gln Met Cys Lys Ala Thr Ser Ala Ala Leu Pro Gln Ser Gln Arg
            980                 985                 990

Ser Ser Thr Pro Ser Ser Glu Ile Gly Ala Thr Pro Pro Ser Ser Pro
        995                 1000                1005

His His Ile Leu Thr Trp Gln Thr Gly Glu Ala Thr Glu Asn Ser
    1010                1015                1020

Pro Ile Leu Asp Gly Ser Glu Ser Pro Pro His Gln Ser Thr Asp
    1025                1030                1035

Glu

<210> SEQ ID NO 6
<211> LENGTH: 244
<212> TYPE: PRT

<213> ORGANISM: Homo sapiens

<400> SEQUENCE: 6

```
Met Ala Ala Ala Ala Ser Pro Ala Ile Leu Pro Arg Leu Ala Ile Leu
1               5                   10                  15

Pro Tyr Leu Leu Phe Asp Trp Ser Gly Thr Gly Arg Ala Asp Ala His
            20                  25                  30

Ser Leu Trp Tyr Asn Phe Thr Ile Ile His Leu Pro Arg His Gly Gln
        35                  40                  45

Gln Trp Cys Glu Val Gln Ser Gln Val Asp Gln Lys Asn Phe Leu Ser
    50                  55                  60

Tyr Asp Cys Gly Ser Asp Lys Val Leu Ser Met Gly His Leu Glu Glu
65                  70                  75                  80

Gln Leu Tyr Ala Thr Asp Ala Trp Gly Lys Gln Leu Glu Met Leu Arg
                85                  90                  95

Glu Val Gly Gln Arg Leu Arg Leu Glu Leu Ala Asp Thr Glu Leu Glu
            100                 105                 110

Asp Phe Thr Pro Ser Gly Pro Leu Thr Leu Gln Val Arg Met Ser Cys
        115                 120                 125

Glu Cys Glu Ala Asp Gly Tyr Ile Arg Gly Ser Trp Gln Phe Ser Phe
    130                 135                 140

Asp Gly Arg Lys Phe Leu Leu Phe Asp Ser Asn Asn Arg Lys Trp Thr
145                 150                 155                 160

Val Val His Ala Gly Ala Arg Arg Met Lys Glu Lys Trp Glu Lys Asp
                165                 170                 175

Ser Gly Leu Thr Thr Phe Phe Lys Met Val Ser Met Arg Asp Cys Lys
            180                 185                 190

Ser Trp Leu Arg Asp Phe Leu Met His Arg Lys Lys Arg Leu Glu Pro
        195                 200                 205

Thr Ala Pro Pro Thr Met Ala Pro Gly Leu Ala Gln Pro Lys Ala Ile
    210                 215                 220

Ala Thr Thr Leu Ser Pro Trp Ser Phe Leu Ile Ile Leu Cys Phe Ile
225                 230                 235                 240

Leu Pro Gly Ile
```

<210> SEQ ID NO 7
<211> LENGTH: 536
<212> TYPE: PRT
<213> ORGANISM: Homo sapiens

<400> SEQUENCE: 7

```
Met Glu Ile Arg Gln His Glu Trp Leu Ser Ala Ser Pro His Glu Gly
1               5                   10                  15

Phe Glu Gln Met Arg Leu Lys Ser Arg Pro Lys Glu Pro Ser Pro Ser
            20                  25                  30

Leu Thr Arg Val Gly Ala Asn Phe Tyr Ser Ser Val Lys Gln Gln Asp
        35                  40                  45

Tyr Ser Ala Ser Val Trp Leu Arg Arg Lys Asp Lys Leu Glu His Ser
    50                  55                  60

Gln Gln Lys Cys Ile Val Ile Phe Ala Leu Val Cys Phe Ala Ile
65                  70                  75                  80

Leu Val Ala Leu Ile Phe Ser Ala Val Asp Ile Met Gly Glu Asp Glu
                85                  90                  95

Asp Gly Leu Ser Glu Lys Asn Cys Gln Asn Lys Cys Arg Ile Ala Leu
            100                 105                 110
```

```
Val Glu Asn Ile Pro Glu Gly Leu Asn Tyr Ser Glu Asn Ala Pro Phe
            115                 120                 125

His Leu Ser Leu Phe Gln Gly Trp Met Asn Leu Leu Asn Met Ala Lys
        130                 135                 140

Lys Ser Val Asp Ile Val Ser Ser His Trp Asp Leu Asn His Thr His
145                 150                 155                 160

Pro Ser Ala Cys Gln Gly Gln Arg Leu Phe Glu Lys Leu Leu Gln Leu
                165                 170                 175

Thr Ser Gln Asn Ile Glu Ile Lys Leu Val Ser Asp Val Thr Ala Asp
                180                 185                 190

Ser Lys Val Leu Glu Ala Leu Lys Leu Lys Gly Ala Glu Val Thr Tyr
            195                 200                 205

Met Asn Met Thr Ala Tyr Asn Lys Gly Arg Leu Gln Ser Ser Phe Trp
        210                 215                 220

Ile Val Asp Lys Gln His Val Tyr Ile Gly Ser Ala Gly Leu Asp Trp
225                 230                 235                 240

Gln Ser Leu Gly Gln Met Lys Glu Leu Gly Val Ile Phe Tyr Asn Cys
                245                 250                 255

Ser Cys Leu Val Leu Asp Leu Gln Arg Ile Phe Ala Leu Tyr Ser Ser
            260                 265                 270

Leu Lys Phe Lys Ser Arg Val Pro Gln Thr Trp Ser Lys Arg Leu Tyr
        275                 280                 285

Gly Val Tyr Asp Asn Glu Lys Lys Leu Gln Leu Gln Leu Asn Glu Thr
        290                 295                 300

Lys Ser Gln Ala Phe Val Ser Asn Ser Pro Lys Leu Phe Cys Pro Lys
305                 310                 315                 320

Asn Arg Ser Phe Asp Ile Asp Ala Ile Tyr Ser Val Ile Asp Asp Ala
                325                 330                 335

Lys Gln Tyr Val Tyr Ile Ala Val Met Asp Tyr Leu Pro Ile Ser Ser
                340                 345                 350

Thr Ser Thr Lys Arg Thr Tyr Trp Pro Asp Leu Asp Ala Lys Ile Arg
            355                 360                 365

Glu Ala Leu Val Leu Arg Ser Val Arg Val Arg Leu Leu Leu Ser Phe
370                 375                 380

Trp Lys Glu Thr Asp Pro Leu Thr Phe Asn Phe Ile Ser Ser Leu Lys
385                 390                 395                 400

Ala Ile Cys Thr Glu Ile Ala Asn Cys Ser Leu Lys Val Lys Phe Phe
                405                 410                 415

Asp Leu Glu Arg Glu Asn Ala Cys Ala Thr Lys Glu Gln Lys Asn His
            420                 425                 430

Thr Phe Pro Arg Leu Asn Arg Asn Lys Tyr Met Val Thr Asp Gly Ala
        435                 440                 445

Ala Tyr Ile Gly Asn Phe Asp Trp Val Gly Asn Asp Phe Thr Gln Asn
        450                 455                 460

Ala Gly Thr Gly Leu Val Ile Asn Gln Ala Asp Val Arg Asn Asn Arg
465                 470                 475                 480

Ser Ile Ile Lys Gln Leu Lys Asp Val Phe Glu Arg Asp Trp Tyr Ser
                485                 490                 495

Pro Tyr Ala Lys Thr Leu Gln Pro Thr Lys Gln Pro Asn Cys Ser Ser
                500                 505                 510

Leu Phe Lys Leu Lys Pro Leu Ser Asn Lys Thr Ala Thr Asp Asp Thr
        515                 520                 525
```

```
Gly Gly Lys Asp Pro Arg Asn Val
    530             535
```

<210> SEQ ID NO 8
<211> LENGTH: 344
<212> TYPE: PRT
<213> ORGANISM: Homo sapiens

<400> SEQUENCE: 8

```
Gln Asn Leu Pro Ser Ser Pro Ala Pro Ser Thr Ile Phe Ser Gly Gly
1               5                   10                  15

Phe Arg His Gly Ser Leu Ile Ser Ile Asp Ser Thr Cys Thr Glu Met
            20                  25                  30

Gly Asn Phe Asp Asn Ala Asn Val Thr Gly Glu Ile Glu Phe Ala Ile
        35                  40                  45

His Tyr Cys Phe Lys Thr His Ser Leu Glu Ile Cys Ile Lys Ala Cys
    50                  55                  60

Lys Asn Leu Ala Tyr Gly Glu Glu Lys Lys Lys Cys Asn Pro Tyr
65                  70                  75                  80

Val Lys Thr Tyr Leu Leu Pro Asp Arg Ser Gln Gly Lys Arg Lys
                85                  90                  95

Thr Gly Val Gln Arg Asn Thr Val Asp Pro Thr Phe Gln Glu Thr Leu
            100                 105                 110

Lys Tyr Gln Val Ala Pro Ala Gln Leu Val Thr Arg Gln Leu Gln Val
        115                 120                 125

Ser Val Trp His Leu Gly Thr Leu Ala Arg Arg Val Phe Leu Gly Glu
    130                 135                 140

Val Ile Ile Ser Leu Ala Thr Trp Asp Phe Glu Asp Ser Thr Thr Gln
145                 150                 155                 160

Ser Phe Arg Trp His Pro Leu Arg Ala Lys Ala Glu Lys Tyr Glu Asp
                165                 170                 175

Ser Val Pro Gln Ser Asn Gly Glu Leu Thr Val Arg Ala Lys Leu Val
            180                 185                 190

Leu Pro Ser Arg Pro Arg Lys Leu Gln Glu Ala Gln Glu Gly Thr Asp
        195                 200                 205

Gln Pro Ser Leu His Gly Gln Leu Cys Leu Val Val Leu Gly Ala Lys
    210                 215                 220

Asn Leu Pro Val Arg Pro Asp Gly Thr Leu Asn Ser Phe Val Lys Gly
225                 230                 235                 240

Cys Leu Thr Leu Pro Asp Gln Gln Lys Leu Arg Leu Lys Ser Pro Val
                245                 250                 255

Leu Arg Lys Gln Ala Cys Pro Gln Trp Lys His Ser Phe Val Phe Ser
            260                 265                 270

Gly Val Thr Pro Ala Gln Leu Arg Gln Ser Ser Leu Glu Leu Thr Val
        275                 280                 285

Trp Asp Gln Ala Leu Phe Gly Met Asn Asp Arg Leu Leu Gly Gly Thr
    290                 295                 300

Arg Leu Gly Ser Lys Gly Asp Thr Ala Val Gly Gly Asp Ala Cys Ser
305                 310                 315                 320

Leu Ser Lys Leu Gln Trp Gln Lys Val Leu Ser Ser Pro Asn Leu Trp
                325                 330                 335

Thr Asp Met Thr Leu Val Leu His
            340
```

<210> SEQ ID NO 9

<211> LENGTH: 263
<212> TYPE: PRT
<213> ORGANISM: Homo sapiens

<400> SEQUENCE: 9

Met Phe Arg Asn Gln Tyr Asp Asn Asp Val Thr Val Trp Ser Pro Gln
1               5                   10                  15

Gly Arg Ile His Gln Ile Glu Tyr Ala Met Glu Ala Val Lys Gln Gly
            20                  25                  30

Ser Ala Thr Val Gly Leu Lys Ser Lys Thr His Ala Val Leu Val Ala
        35                  40                  45

Leu Lys Arg Ala Gln Ser Glu Leu Ala Ala His Gln Lys Lys Ile Leu
50                  55                  60

His Val Asp Asn His Ile Gly Ile Ser Ile Ala Gly Leu Thr Ala Asp
65                  70                  75                  80

Ala Arg Leu Leu Cys Asn Phe Met Arg Gln Glu Cys Leu Asp Ser Arg
                85                  90                  95

Phe Val Phe Asp Arg Pro Leu Pro Val Ser Arg Leu Val Ser Leu Ile
            100                 105                 110

Gly Ser Lys Thr Gln Ile Pro Thr Gln Arg Tyr Gly Arg Arg Pro Tyr
        115                 120                 125

Gly Val Gly Leu Leu Ile Ala Gly Tyr Asp Asp Met Gly Pro His Ile
130                 135                 140

Phe Gln Thr Cys Pro Ser Ala Asn Tyr Phe Asp Cys Arg Ala Met Ser
145                 150                 155                 160

Ile Gly Ala Arg Ser Gln Ser Ala Arg Thr Tyr Leu Glu Arg His Met
                165                 170                 175

Ser Glu Phe Met Glu Cys Asn Leu Asn Glu Leu Val Lys His Gly Leu
            180                 185                 190

Arg Ala Leu Arg Glu Thr Leu Pro Ala Glu Gln Asp Leu Thr Thr Lys
        195                 200                 205

Asn Val Ser Ile Gly Ile Val Gly Lys Asp Leu Glu Phe Thr Ile Tyr
210                 215                 220

Asp Asp Asp Asp Val Ser Pro Phe Leu Glu Gly Leu Glu Glu Arg Pro
225                 230                 235                 240

Gln Arg Lys Ala Gln Pro Ala Gln Pro Ala Asp Glu Pro Ala Glu Lys
                245                 250                 255

Ala Asp Glu Pro Met Glu His
            260

<210> SEQ ID NO 10
<211> LENGTH: 287
<212> TYPE: PRT
<213> ORGANISM: Homo sapiens

<400> SEQUENCE: 10

Met Lys Asp Arg Leu Ala Glu Leu Leu Asp Leu Ser Lys Gln Tyr Asp
1               5                   10                  15

Gln Gln Phe Pro Asp Gly Asp Asp Glu Phe Asp Ser Pro His Glu Asp
            20                  25                  30

Ile Val Phe Glu Thr Asp His Ile Leu Glu Ser Leu Tyr Arg Asp Ile
        35                  40                  45

Arg Asp Ile Gln Asp Glu Asn Gln Leu Leu Val Ala Asp Val Lys Arg
50                  55                  60

Leu Gly Lys Gln Asn Ala Arg Phe Leu Thr Ser Met Arg Arg Leu Ser
65                  70                  75                  80

```
Ser Ile Lys Arg Asp Thr Asn Ser Ile Ala Lys Ala Ile Lys Ala Arg
                85                  90                  95

Gly Glu Val Ile His Cys Lys Leu Arg Ala Met Lys Glu Leu Ser Glu
            100                 105                 110

Ala Ala Glu Ala Gln His Gly Pro His Ser Ala Val Ala Arg Ile Ser
        115                 120                 125

Arg Ala Gln Tyr Asn Ala Leu Thr Leu Thr Phe Gln Arg Ala Met His
    130                 135                 140

Asp Tyr Asn Gln Ala Glu Met Lys Gln Arg Asp Asn Cys Lys Ile Arg
145                 150                 155                 160

Ile Gln Arg Gln Leu Glu Ile Met Gly Lys Glu Val Ser Gly Asp Gln
                165                 170                 175

Ile Glu Asp Met Phe Glu Gln Gly Lys Trp Asp Val Phe Ser Glu Asn
            180                 185                 190

Leu Leu Ala Asp Val Lys Gly Ala Arg Ala Ala Leu Asn Glu Ile Glu
        195                 200                 205

Ser Arg His Arg Glu Leu Leu Arg Leu Glu Ser Arg Ile Arg Asp Val
    210                 215                 220

His Glu Leu Phe Leu Gln Met Ala Val Leu Val Glu Lys Gln Ala Asp
225                 230                 235                 240

Thr Leu Asn Val Ile Glu Leu Asn Val Gln Lys Thr Val Asp Tyr Thr
                245                 250                 255

Gly Gln Ala Lys Ala Gln Val Arg Lys Ala Val Gln Tyr Glu Glu Lys
            260                 265                 270

Asn Pro Cys Arg Thr Leu Cys Cys Phe Cys Pro Cys Leu Lys
        275                 280                 285

<210> SEQ ID NO 11
<211> LENGTH: 244
<212> TYPE: PRT
<213> ORGANISM: Homo sapiens

<400> SEQUENCE: 11

Met Ala Ala Ala Ala Ser Pro Ala Ile Leu Pro Arg Leu Ala Ile Leu
1               5                   10                  15

Pro Tyr Leu Leu Phe Asp Trp Ser Gly Thr Gly Arg Ala Asp Ala His
            20                  25                  30

Ser Leu Trp Tyr Asn Phe Thr Ile Ile His Leu Pro Arg His Gly Gln
        35                  40                  45

Gln Trp Cys Glu Val Gln Ser Gln Val Asp Gln Lys Asn Phe Leu Ser
    50                  55                  60

Tyr Asp Cys Gly Ser Asp Lys Val Leu Ser Met Gly His Leu Glu Glu
65                  70                  75                  80

Gln Leu Tyr Ala Thr Asp Ala Trp Gly Lys Gln Leu Glu Met Leu Arg
                85                  90                  95

Glu Val Gly Gln Arg Leu Arg Leu Glu Leu Ala Asp Thr Glu Leu Glu
            100                 105                 110

Asp Phe Thr Pro Ser Gly Pro Leu Thr Leu Gln Val Arg Met Ser Cys
        115                 120                 125

Glu Cys Glu Ala Asp Gly Tyr Ile Arg Gly Ser Trp Gln Phe Ser Phe
    130                 135                 140

Asp Gly Arg Lys Phe Leu Leu Phe Asp Ser Asn Asn Arg Lys Trp Thr
145                 150                 155                 160

Val Val His Ala Gly Ala Arg Arg Met Lys Glu Lys Trp Glu Lys Asp
```

```
            165                 170                 175
Ser Gly Leu Thr Thr Phe Phe Lys Met Val Ser Met Arg Asp Cys Lys
            180                 185                 190

Ser Trp Leu Arg Asp Phe Leu Met His Arg Lys Arg Leu Glu Pro
            195                 200                 205

Thr Ala Pro Pro Thr Met Ala Pro Gly Leu Ala Gln Pro Lys Ala Ile
            210                 215                 220

Ala Thr Thr Leu Ser Pro Trp Ser Phe Leu Ile Ile Leu Cys Phe Ile
225                 230                 235                 240

Leu Pro Gly Ile

<210> SEQ ID NO 12
<211> LENGTH: 322
<212> TYPE: PRT
<213> ORGANISM: Homo sapiens

<400> SEQUENCE: 12

Met Ser Ala Lys Ser Arg Thr Ile Gly Ile Ile Gly Ala Pro Phe Ser
1               5                   10                  15

Lys Gly Gln Pro Arg Gly Gly Val Glu Glu Gly Pro Thr Val Leu Arg
            20                  25                  30

Lys Ala Gly Leu Leu Glu Lys Leu Lys Glu Gln Glu Cys Asp Val Lys
        35                  40                  45

Asp Tyr Gly Asp Leu Pro Phe Ala Asp Ile Pro Asn Asp Ser Pro Phe
    50                  55                  60

Gln Ile Val Lys Asn Pro Arg Ser Val Gly Lys Ala Ser Glu Gln Leu
65                  70                  75                  80

Ala Gly Lys Val Ala Glu Val Lys Lys Asn Gly Arg Ile Ser Leu Val
                85                  90                  95

Leu Gly Gly Asp His Ser Leu Ala Ile Gly Ser Ile Ser Gly His Ala
            100                 105                 110

Arg Val His Pro Asp Leu Gly Val Ile Trp Val Asp Ala His Thr Asp
        115                 120                 125

Ile Asn Thr Pro Leu Thr Thr Thr Ser Gly Asn Leu His Gly Gln Pro
    130                 135                 140

Val Ser Phe Leu Leu Lys Glu Leu Lys Gly Lys Ile Pro Asp Val Pro
145                 150                 155                 160

Gly Phe Ser Trp Val Thr Pro Cys Ile Ser Ala Lys Asp Ile Val Tyr
                165                 170                 175

Ile Gly Leu Arg Asp Val Asp Pro Gly Glu His Tyr Ile Leu Lys Thr
            180                 185                 190

Leu Gly Ile Lys Tyr Phe Ser Met Thr Glu Val Asp Arg Leu Gly Ile
        195                 200                 205

Gly Lys Val Met Glu Glu Thr Leu Ser Tyr Leu Leu Gly Arg Lys Lys
    210                 215                 220

Arg Pro Ile His Leu Ser Phe Asp Val Asp Gly Leu Asp Pro Ser Phe
225                 230                 235                 240

Thr Pro Ala Thr Gly Thr Pro Val Val Gly Gly Leu Thr Tyr Arg Glu
                245                 250                 255

Gly Leu Tyr Ile Thr Glu Glu Ile Tyr Lys Thr Gly Leu Leu Ser Gly
            260                 265                 270

Leu Asp Ile Met Glu Val Asn Pro Ser Leu Gly Lys Thr Pro Glu Glu
        275                 280                 285

Val Thr Arg Thr Val Asn Thr Ala Val Ala Ile Thr Leu Ala Cys Phe
```

```
                290                 295                 300
Gly Leu Ala Arg Glu Gly Asn His Lys Pro Ile Asp Tyr Leu Asn Pro
305                 310                 315                 320

Pro Lys

<210> SEQ ID NO 13
<211> LENGTH: 213
<212> TYPE: PRT
<213> ORGANISM: Homo sapiens

<400> SEQUENCE: 13

Met Asp Thr Glu Arg Val Gly Asp Gly Lys Gln His Arg Arg Lys Gln
1               5                   10                  15

Ser Gln Arg Leu Arg Trp Pro Cys Cys Leu Ala Leu Val Pro Asp Arg
            20                  25                  30

His Pro Ser Gln Leu Ser Ser Cys Thr Leu Cys Leu Leu Ala Ala Ala
        35                  40                  45

Ser Gln Trp Glu Ser Trp Ala His Phe Ser Lys Trp His Thr Glu Ala
    50                  55                  60

Ser Thr Gly Thr His Leu Gly Lys Ala Lys Ala Glu Gly Leu Gly Cys
65                  70                  75                  80

Thr Val Lys Asn Thr Pro Gln Leu Ser Ile Cys Glu Pro Ser His Phe
                85                  90                  95

Gly Pro Ser Phe Val His Ser Pro His Leu Leu Val Asp His Asp His
            100                 105                 110

Arg Ala Gly Ala Ala Thr Gly Arg Gly Gln Ala Gly Pro Ser Arg Ala
        115                 120                 125

Ser Ser Val Ser Pro Thr Phe Cys Pro Pro Thr Thr Ser His His Pro
    130                 135                 140

Val Cys Ala Lys Gly Thr Asp Pro Val Leu Val Leu Gln Glu Glu Glu
145                 150                 155                 160

Gln Asp Leu Asp Gly Glu Lys Gly Pro Ser Glu Gly Pro Glu Glu Glu
                165                 170                 175

Glu Asp Gly Glu Gly Phe Ser Phe Lys Tyr Ser Pro Gly Lys Leu Arg
            180                 185                 190

Gly Asn Gln Tyr Lys Lys Met Met Thr Lys Glu Glu Leu Glu Glu Glu
        195                 200                 205

Gln Arg Thr Glu Glu
    210

<210> SEQ ID NO 14
<211> LENGTH: 117
<212> TYPE: PRT
<213> ORGANISM: Homo sapiens

<400> SEQUENCE: 14

Gly Glu Ala Arg Gly Lys Leu Leu Gln Leu Ile Glu Gln Gln Lys Leu
1               5                   10                  15

Val Gly Leu Asn Leu Ser Pro Pro Met Ser Pro Val Gln Leu Pro Leu
            20                  25                  30

Arg Ala Trp Thr Glu Gly Ala Lys Arg Thr Ile Glu Val Ser Ile Pro
        35                  40                  45

Gly Ala Glu Ala Pro Glu Ser Ser Lys Cys Ser Thr Val Ser Pro Val
    50                  55                  60

Ser Gly Ile Asn Thr Arg Arg Ser Ser Gly Ala Thr Gly Asn Ser Cys
65                  70                  75                  80
```

```
Ser Pro Leu Asn Ala Thr Ser Gly Gly Arg Phe Thr Pro Leu Asn
                85                  90                  95

Pro Arg Ala Lys Ile Glu Lys Gln Asn Glu Glu Gly Trp Phe Ala Leu
            100                 105                 110

Ser Thr His Val Ser
        115

<210> SEQ ID NO 15
<211> LENGTH: 1046
<212> TYPE: PRT
<213> ORGANISM: Homo sapiens

<400> SEQUENCE: 15

Arg Gln Gly Gly Arg Pro Ser Ser Pro Gln Ala Ser Arg Ala Arg Gln
1               5                   10                  15

Leu Pro Ser Ile Glu Ile Gln Gln Trp Glu Gln Asn Leu Glu Lys Phe
            20                  25                  30

His Met Asp Leu Phe Arg Met Arg Cys Tyr Leu Ala Ser Leu Gln Gly
        35                  40                  45

Gly Glu Leu Pro Asn Pro Lys Ser Leu Leu Ala Ala Ser Arg Pro
    50                  55                  60

Ser Lys Leu Ala Leu Gly Arg Leu Gly Ile Leu Ser Val Ser Ser Phe
65              70                  75                  80

His Ala Leu Val Cys Ser Arg Asp Asp Ser Ala Leu Arg Lys Arg Thr
                85                  90                  95

Leu Ser Leu Thr Gln Arg Gly Arg Asn Lys Lys Gly Ile Phe Ser Ser
            100                 105                 110

Leu Lys Gly Leu Asp Thr Leu Ala Arg Lys Gly Lys Glu Lys Arg Pro
        115                 120                 125

Ser Ile Thr Gln Val Asp Glu Leu Leu His Ile Tyr Gly Ser Thr Val
130                 135                 140

Asp Gly Val Pro Arg Asp Asn Ala Trp Glu Ile Gln Thr Tyr Val His
145                 150                 155                 160

Phe Gln Asp Asn His Gly Val Thr Val Gly Ile Lys Pro Glu His Arg
                165                 170                 175

Val Glu Asp Ile Leu Thr Leu Ala Cys Lys Met Arg Gln Leu Glu Pro
            180                 185                 190

Ser His Tyr Gly Leu Gln Leu Arg Lys Leu Val Asp Asn Val Glu
        195                 200                 205

Tyr Cys Ile Pro Ala Pro Tyr Glu Tyr Met Gln Gln Val Tyr Asp
    210                 215                 220

Glu Ile Glu Val Phe Pro Leu Asn Val Tyr Asp Val Gln Leu Thr Lys
225                 230                 235                 240

Thr Gly Ser Val Cys Asp Phe Gly Phe Ala Val Thr Ala Gln Val Asp
                245                 250                 255

Glu Arg Gln His Leu Ser Arg Ile Phe Ile Ser Asp Val Leu Pro Asp
            260                 265                 270

Gly Leu Ala Tyr Gly Glu Gly Leu Arg Lys Gly Asn Glu Ile Met Thr
        275                 280                 285

Leu Asn Gly Glu Ala Val Ser Asp Leu Asp Leu Lys Gln Met Glu Ala
    290                 295                 300

Leu Phe Ser Glu Lys Ser Val Gly Leu Thr Leu Ile Ala Arg Pro Pro
305                 310                 315                 320

Asp Thr Lys Ala Thr Leu Cys Thr Ser Trp Ser Asp Ser Asp Leu Phe
```

```
            325                 330                 335
Ser Arg Asp Gln Lys Ser Leu Leu Pro Pro Asn Gln Ser Gln Leu
            340                 345                 350
Leu Glu Glu Phe Leu Asp Asn Phe Lys Lys Asn Thr Ala Asn Asp Phe
            355                 360                 365
Ser Asn Val Pro Asp Ile Thr Thr Gly Leu Lys Arg Ser Gln Thr Asp
370                 375                 380
Gly Thr Leu Asp Gln Val Ser His Arg Glu Lys Met Glu Gln Thr Phe
385                 390                 395                 400
Arg Ser Ala Glu Gln Ile Thr Ala Leu Cys Arg Ser Phe Asn Asp Ser
            405                 410                 415
Gln Ala Asn Gly Met Glu Gly Pro Arg Glu Asn Gln Asp Pro Pro Pro
            420                 425                 430
Arg Ser Leu Ala Arg His Leu Ser Asp Ala Asp Arg Leu Arg Lys Val
            435                 440                 445
Ile Gln Glu Leu Val Asp Thr Glu Lys Ser Tyr Val Lys Asp Leu Ser
            450                 455                 460
Cys Leu Phe Glu Leu Tyr Leu Glu Pro Leu Gln Asn Glu Thr Phe Leu
465                 470                 475                 480
Thr Gln Asp Glu Met Glu Ser Leu Phe Gly Ser Leu Pro Glu Met Leu
                    485                 490                 495
Glu Phe Gln Lys Val Phe Leu Glu Thr Leu Glu Asp Gly Ile Ser Ala
            500                 505                 510
Ser Ser Asp Phe Asn Thr Leu Glu Thr Pro Ser Gln Phe Arg Lys Leu
            515                 520                 525
Leu Phe Ser Leu Gly Gly Ser Phe Leu Tyr Tyr Ala Asp His Phe Lys
            530                 535                 540
Leu Tyr Ser Gly Phe Cys Ala Asn His Ile Lys Val Gln Lys Val Leu
545                 550                 555                 560
Glu Arg Ala Lys Thr Asp Lys Ala Phe Lys Ala Phe Leu Asp Ala Arg
                    565                 570                 575
Asn Pro Thr Lys Gln His Ser Ser Thr Leu Glu Ser Tyr Leu Ile Lys
            580                 585                 590
Pro Val Gln Arg Val Leu Lys Tyr Pro Leu Leu Leu Lys Glu Leu Val
            595                 600                 605
Ser Leu Thr Asp Gln Glu Ser Glu Glu His Tyr His Leu Thr Glu Ala
            610                 615                 620
Leu Lys Ala Met Glu Lys Val Ala Ser His Ile Asn Glu Met Gln Lys
625                 630                 635                 640
Ile Tyr Glu Asp Tyr Gly Thr Val Phe Asp Gln Leu Val Ala Glu Gln
                    645                 650                 655
Ser Gly Thr Glu Lys Glu Val Thr Glu Leu Ser Met Gly Glu Leu Leu
            660                 665                 670
Met His Ser Thr Val Ser Trp Leu Asn Pro Phe Leu Ser Leu Gly Lys
            675                 680                 685
Ala Arg Lys Asp Leu Glu Leu Thr Val Phe Val Phe Lys Arg Ala Val
            690                 695                 700
Ile Leu Val Tyr Lys Glu Asn Cys Lys Leu Lys Lys Lys Leu Pro Ser
705                 710                 715                 720
Asn Ser Arg Pro Ala His Asn Ser Thr Asp Leu Asp Pro Phe Lys Phe
                    725                 730                 735
Arg Trp Leu Ile Pro Ile Ser Ala Leu Gln Val Arg Leu Gly Asn Pro
            740                 745                 750
```

```
Ala Gly Thr Glu Asn Asn Ser Ile Trp Glu Leu Ile His Thr Lys Ser
        755                 760                 765

Glu Ile Glu Gly Arg Pro Glu Thr Ile Phe Gln Leu Cys Cys Ser Asp
770                 775                 780

Ser Glu Ser Lys Thr Asn Ile Val Lys Val Ile Arg Ser Ile Leu Arg
785                 790                 795                 800

Glu Asn Phe Arg Arg His Ile Lys Cys Glu Leu Pro Leu Glu Lys Thr
                805                 810                 815

Cys Lys Asp Arg Leu Val Pro Leu Lys Asn Arg Val Pro Val Ser Ala
                820                 825                 830

Lys Leu Ala Ser Ser Arg Ser Leu Lys Val Leu Lys Asn Ser Ser Ser
                835                 840                 845

Asn Glu Trp Thr Gly Glu Thr Gly Lys Gly Thr Leu Leu Asp Ser Asp
        850                 855                 860

Glu Gly Ser Leu Ser Ser Gly Thr Gln Ser Ser Gly Cys Pro Thr Ala
865                 870                 875                 880

Glu Gly Arg Gln Asp Ser Lys Ser Thr Ser Pro Gly Lys Tyr Pro His
                885                 890                 895

Pro Gly Leu Ala Asp Phe Ala Asp Asn Leu Ile Lys Glu Ser Asp Ile
                900                 905                 910

Leu Ser Asp Glu Asp Asp His Arg Gln Thr Val Lys Gln Gly Ser
                915                 920                 925

Pro Thr Lys Asp Ile Glu Ile Gln Phe Gln Arg Leu Arg Ile Ser Glu
        930                 935                 940

Asp Pro Asp Val His Pro Glu Ala Glu Gln Pro Gly Pro Glu Ser
945                 950                 955                 960

Gly Glu Gly Gln Lys Gly Gly Glu Gln Pro Lys Leu Val Arg Gly His
                965                 970                 975

Phe Cys Pro Ile Lys Arg Lys Ala Asn Ser Thr Lys Arg Asp Arg Gly
                980                 985                 990

Thr Leu Leu Lys Ala Gln Ile Arg His Gln Ser Leu Asp Ser Gln Ser
        995                 1000                1005

Glu Asn Ala Thr Ile Asp Leu Asn Ser Val Leu Glu Arg Glu Phe
        1010                1015                1020

Ser Val Gln Ser Leu Thr Ser Val Val Ser Glu Glu Cys Phe Tyr
        1025                1030                1035

Glu Thr Glu Ser His Gly Lys Ser
        1040                1045

<210> SEQ ID NO 16
<211> LENGTH: 232
<212> TYPE: PRT
<213> ORGANISM: Homo sapiens

<400> SEQUENCE: 16

Met Glu Asp Leu Glu Glu Asp Val Arg Phe Ile Val Asp Glu Thr Leu
1               5                   10                  15

Asp Phe Gly Gly Leu Ser Pro Ser Asp Ser Arg Glu Glu Asp Ile
        20                  25                  30

Thr Val Leu Val Thr Pro Glu Lys Pro Leu Arg Arg Gly Leu Ser His
        35                  40                  45

Arg Ser Asp Pro Asn Ala Val Ala Pro Ala Pro Gln Gly Val Arg Leu
    50                  55                  60

Ser Leu Gly Pro Leu Ser Pro Glu Lys Leu Glu Glu Ile Leu Asp Glu
```

-continued

```
                65                  70                  75                  80
Ala Asn Arg Leu Ala Ala Gln Leu Glu Gln Cys Ala Leu Gln Asp Arg
                    85                  90                  95

Glu Ser Ala Gly Glu Gly Leu Gly Pro Arg Arg Val Lys Pro Ser Pro
                100                 105                 110

Arg Arg Glu Thr Phe Val Leu Lys Asp Ser Pro Val Arg Asp Leu Leu
                115                 120                 125

Pro Thr Val Asn Ser Leu Thr Arg Ser Thr Pro Ser Pro Ser Ser Leu
            130                 135                 140

Thr Pro Arg Leu Arg Ser Asn Asp Arg Lys Gly Ser Val Arg Ala Leu
145                 150                 155                 160

Arg Ala Thr Ser Gly Lys Arg Pro Ser Asn Met Lys Arg Glu Ser Pro
                165                 170                 175

Thr Cys Asn Leu Phe Pro Ala Ser Lys Ser Pro Ala Ser Ser Pro Leu
                180                 185                 190

Thr Arg Ser Thr Pro Pro Val Arg Gly Arg Ala Gly Pro Ser Gly Arg
                195                 200                 205

Ala Ala Ala Ser Pro Pro Thr Pro Ile Arg Ser Val Leu Ala Pro Gln
            210                 215                 220

Pro Ser Thr Ser Asn Ser Gln Arg
225                 230

<210> SEQ ID NO 17
<211> LENGTH: 63
<212> TYPE: PRT
<213> ORGANISM: Homo sapiens

<400> SEQUENCE: 17

Met Leu Gly Gln Ser Ile Arg Arg Phe Thr Thr Ser Val Val Arg Arg
1               5                   10                  15

Ser His Tyr Glu Glu Gly Pro Gly Lys Asn Leu Pro Phe Ser Val Glu
                20                  25                  30

Asn Lys Trp Ser Leu Leu Ala Lys Met Cys Leu Tyr Phe Gly Ser Ala
            35                  40                  45

Phe Ala Thr Pro Phe Leu Val Val Arg His Gln Leu Leu Lys Thr
        50                  55                  60
```

METHODS OF IDENTIFICATION, ASSESSMENT, PREVENTION AND THERAPY OF LUNG DISEASES AND KITS THEREOF INCLUDING GENDER-BASED DISEASE IDENTIFICATION, ASSESSMENT, PREVENTION AND THERAPY

CROSS-REFERENCE TO RELATED APPLICATIONS

This application is a continuation of U.S. patent application Ser. No. 13/256/630, filed Aug. 7, 2012, which Granted as U.S. Pat. No. 9,933,429, which Issued on Apr. 3, 2018, which is a U.S. National Phase of International Patent Application No. PCT/US10/27243, filed Mar. 12, 2010, which is a Continuation-In-Part of U.S. Ser. No. 12/403,369, filed Mar. 12, 2009, which Granted as U.S. Pat. No. 8,541,183, which issued on Sep. 24, 2013, which claims benefit to U.S. Provisional Patent Application No. 61/237,198, filed Aug. 26, 2009, the contents of each are hereby incorporated by reference in their entireties.

BACKGROUND OF THE INVENTION

(a) Field of the Invention

The invention relates to the detection, identification, assessment, prevention, diagnosis, and treatment of lung disease using biomarkers and kits thereof. More specifically, the invention relates to the diagnosis of non-small cell lung cancers and reactive airway diseases by measuring and quantifying expression levels of specific biomarkers. The invention also relates to the identification of biomarkers present in human serum or other biological fluids, which, when found to be expressed at levels different from those found in the normal population, are indicative of pathologies associated with human lung tissues and the human respiratory system. By identifying the biomarkers associated with such pathologies, quantifying the expression levels of those biomarkers, and comparing the expression levels with those levels generally expected to present in a normal person's serum, it is possible to detect the presence of the pathologies early on in their progression through simple blood tests and characterize the progression of the pathology, as well as to differentiate among the pathologies.

(b) Description of the Related Art

Pathologies of the respiratory system, such as asthma and lung cancer, affect millions of Americans. In fact, the American Lung Association® reports that almost 20 million Americans suffer from asthma. The American Cancer Society, Inc. estimated 229,400 new cancer cases of the respiratory system and 164,840 deaths from cancers of the respiratory system in 2007 alone. While the five year survival rate of all cancer cases when the cancer is detected while still localized is 46%, the five year survival rate of lung cancer patients is only 13%. Correspondingly, only 16% of lung cancers are discovered before the disease has spread. Lung cancers are generally categorized as two main types based on the pathology of the cancer cells. Each type is named for the types of cells that were transformed to become cancerous. Small cell lung cancers are derived from small cells in the human lung tissues, whereas non-small-cell lung cancers generally encompass all lung cancers that are not small-cell type. Non-small cell lung cancers are grouped together because the treatment is generally the same for all non-small-cell types. Together, non-small-cell lung cancers, or NSCLCs, make up about 75% of all lung cancers.

A major factor in the low survival rate of lung cancer patients is the fact that lung cancer is difficult to diagnose early. Current methods of diagnosing lung cancer or identifying its existence in a human are restricted to taking X-rays, Computed Tomography (CT) scans and similar tests of the lungs to physically determine the presence or absence of a tumor. Therefore, the diagnosis of lung cancer is often made only in response to symptoms which have presented for a significant period of time, and after the disease has been present in the human long enough to produce a physically detectable mass.

Similarly, current methods of detecting asthma are typically performed long after the presentation of symptoms such as recurrent wheezing, coughing, and chest tightness. Current methods of detecting asthma are typically restricted to lung function tests such as spirometry tests or challenge tests. Moreover, these tests are often ordered by the physician to be performed along with a multitude of other tests to rule out other pathologies or reactive airway diseases such as chronic obstructive pulmonary disease (COPD), bronchitis, pneumonia, and congestive heart failure.

There does not exist in the art a simple, reliable method of diagnosing pathologies of human lung tissues early in their development. Furthermore, there is not a blood test available today which is capable of indicating the presence of a particular lung tissue pathology. It is therefore desirable to develop a method to determine the existence of lung cancers early in the disease progression. It is likewise desirable to develop a method to diagnose asthma and non-small cell lung cancer, and to differentiate them from each other and from other lung diseases such as infections, at the earliest appearance of symptoms. It is further desirable to identify specific proteins present in human blood which, when altered in terms of relative intensities of expression, are indicative of the presence of non-small cell lung cancers and/or reactive airway disease.

SUMMARY OF THE INVENTION

The present inventors have identified a number of biomarkers which are useful for characterizing the physiologic state of a subject with regard to lung diseases, such as non-small cell lung cancer or reactive airway disease. These biomarkers are presented in Tables 1-23.

Table 1A lists biomarkers whose expression level has been found to be different from the level in normal individuals when measured in individual with one or more lung diseases. Table 1B lists biomarkers whose expression level has been found to be different from the level in normal individuals when measured in individuals with either non-small cell lung cancer or reactive airway disease, and to show a differential expression level between non-small cell lung cancer and reactive airway disease. Table 1C lists biomarkers whose expression has been found to be different from the level in normal individuals when measured in individuals with non-small cell lung cancer or with reactive airway disease.

Table 2 lists biomarkers whose expression has been found to be different from the level in normal individuals when measured in individuals with reactive airway disease. Table 3 lists biomarkers whose expression has been and to be different from the level in normal individuals when measured in individuals with non-small cell lung cancer. Table 4 lists biomarkers whose expression levels have been found to be different when measured between individuals with non-small cell lung cancer and reactive airway disease.

Table 5A lists biomarkers whose expression level has been found to be different from the level in normal males when measured in males with one or more lung diseases. Table 5B lists biomarkers whose expression level has been found to be different from the level in normal males when measured in males with either non-small cell lung cancer or reactive airway disease, and to show a differential expression level between non-small cell lung cancer and reactive airway disease. Table 5C lists biomarkers whose expression has been found to be different from the level in normal males when measured in males with non-small cell lung cancer and reactive airway disease.

Table 6 lists biomarkers whose expression has been found to be different from the level in normal males when measured in males with reactive airway disease. Table 7 lists biomarkers whose expression has been found to be different from the level in normal males when measured in males with non-small cell lung cancer. Table 8 lists biomarkers whose expression levels have been found to be different when measured between males with non-small cell lung cancer and reactive airway disease.

Table 9A lists biomarkers whose expression level has been found to be different from the level in normal females when measured in females with one or more lung diseases. Table 9B lists biomarkers whose expression level has been found to be different from the level in normal females when measured in females with either non-small cell lung cancer or reactive airway disease, and to show a differential expression level between non-small cell lung cancer and reactive airway disease. Table 9C lists biomarkers whose expression has been found to be different from the level in normal females when measured in females with non-small cell lung cancer and reactive airway disease.

Table 10 lists biomarkers whose expression has been found to be different from the level in normal females when measured in females with reactive airway disease. Table 11 lists biomarkers whose expression has been found to be different from the level in normal females when measured in males with non-small cell lung cancer. Table 12 lists biomarkers whose expression levels have been found to be different when measured between females with non-small cell lung cancer and reactive airway disease.

Table 13A lists biomarkers whose expression significantly differs between male and female reactive airway disease populations. Table 13B lists biomarkers whose expression does not significantly differ between male and female reactive airway disease populations. Table 14A lists biomarkers whose expression significantly differs between male and female non-small cell lung cancer populations. Table 14B lists biomarkers whose expression does not significantly differ between male and female non-small cell lung cancer populations. Table 15A lists biomarkers ranked by relative standard deviation in fluorescence intensity for the normal population. Table 15B lists biomarkers ranked by relative standard deviator in fluorescence intensity for the normal female population. Table 15C lists biomarkers ranked by relative standard deviation in fluorescence intensity for the normal male population.

Table 16A lists biomarkers whose expression level has been found to be different from the level in normal males when measured in males with one or more lung diseases. Table 16B lists biomarkers whose expression level has been found to be different from the level in normal males when measured in males with either non-small cell lung cancer or reactive airway disease, and to show a differential expression level between non-small cell lung cancer and reactive airway disease. Table 16C lists biomarkers whose expression has been found to be different from the level in normal males when measured in males with non-small cell lung cancer and reactive airway disease.

Table 17 lists biomarkers whose expression has been found to be different from the level in normal males when measured in males with reactive airway disease. Table 18 lists biomarkers whose expression has been found to be different from the level in normal males when measured in males with non-small cell lung cancer. Table 19 lists biomarkers whose expression levels have been found to be different when measured between males with non-small cell lung cancer and reactive airway disease.

Table 20A lists biomarkers whose expression level has been found to be different from the level in normal females when measured in females with one or more diseases. Table 20B lists biomarkers whose expression level has been found to be different from the level in normal females when measured in females with either non-small cell lung cancer or reactive airway disease, and to show a differential expression level between non-small cell lung cancer and reactive airway disease. Table 20C lists biomarkers whose expression has been found to be different from the level in normal females when measured in females with non-small cell lung cancer and reactive airway disease.

Table 21 lists biomarkers whose expression has been found to be different from the level in normal females when measured in females with reactive airway disease. Table 22 lists biomarkers whose expression has been found to be different from the level in normal females when measured in females with non-small cell lung cancer. Table 23 lists biomarkers whose expression levels have been found to be different when measured between females with non-small cell lung cancer and reactive airway disease.

Significance for Tables 1-15 were determined using the Student's t test. Significance for Tables 16-23 were determined using the Kruskal-Wallis method.

Polypeptides comprising SEQ ID NOS: 1-17 are additional biomarkers whose expression has been found to change with one or more lung diseases.

The present invention provides various diagnostic, prognostic and therapeutic methods which depend on the identification of these biomarkers.

The invention provides for a method of physiological characterization in a subject comprising determining the extent of expression of at least one biomarker from any number of Tables 1-12 or 16-23 in a physiological sample of the subject, wherein the extent of expression of said at least one biomarker is indicative of a lung disease, such as of non-small cell lung cancer or reactive airway disease, or can assist in distinguishing lung diseases, such as of non-small cell lung cancer or reactive airway disease. The invention also provides for methods of physiological characterization in a subject comprising determining the extent of expression of at least one biomarker from Tables 13B, 14B, or 15B, which also appears on Tables 1-12 or 16-23 in a physiological sample of the subject, preferably the biomarker is at least one of biomarker nos. 1-10 of Tables 1-12 or 16-23, wherein the extent of expression of said at least one biomarker is indicative of a lung disease, such as of non-small cell lung cancer or reactive airway disease. Alternatively, or additionally, the extent of expression of the first order interactors of these biomarkers may be determined.

The invention provides for a method of physiological characterization in a subject comprising determining the extent of expression of SEQ ID NO: 12 in a physiological sample of the subject, wherein the extent of expression of SEQ ID NO: 12 is indicative of a lung disease, such as non-small cell lung cancer or reactive airway disease.

The invention provides for a method of physiological characterization in a subject comprising determining the extent of expression of at least one polypeptide selected from the group consisting of SEQ ID NOS: 1-17 in a physiological sample of the subject, and determining the extent of expression of at least one biomarker from any number of Tables 1-12 or 16-23, wherein the extent of expression of said least one polypeptide and said at least one biomarker from any number of Tables 1-12 or 16-23 is indicative of a lung disease, such as non-small cell lung cancer or reactive airway disease.

The invention provides for a method of diagnosing reactive airway disease in a subject comprising determining the extent of expression of at least one biomarker from Table 2, Table 6, Table 10, Table 17, and Table 21 in a physiological sample of the subject, wherein the extent of expression of said at least one biomarker is indicative of reactive airway disease.

The invention provides for a method of diagnosing non-small cell lung cancer in a subject comprising determining the extent of expression at least one biomarker from Table 3, Table 7, Table 11, Table 18, or Table 22 in a physiological sample of the subject, wherein the extent of expression of said at least one biomarker is indicative of the presence or development of non-small cell lung cancer.

The invention provides a diagnostic method to assist in differentiating the likelihood that a subject is at-risk of non-small cell lung cancer or of reactive airway disease comprising determining the extent of expression of at least one biomarker from Table 4, Table 8, Table 12, Table 19, or Table 23 in a physiological sample of the subject who is at-risk for at least one of non-small cell lung cancer or reactive airway disease, wherein the extent of expression of said at least one biomarker from Table 4, Table 8, Table 12, Table 19, or Table 23 assists in differentiating the likelihood that said subject is at-risk of non-small cell lung cancer or of reactive airway disease.

The invention provides a method for predicting the likelihood that a subject will respond to therapeutic intervention comprising determining the extent one expression of at least one biomarker described herein in a physiological sample of the subject, wherein the extent of expressions of said at least one biomarker assists in predicting a subject's response to said therapeutic intervention.

The invention also provides a method of monitoring a subject comprising determining a first extent of expression of at least one biomarker described herein in a physiological sample of the subject, a second extent of expression of said at least one biomarker in a physiological sample of the subject at a subsequent time to said first determination, and comparing said first extent of expression and said second extent of expression.

The invention also provides for methods of designing kits comprising selecting at least one biomarker described herein, selecting a means for determining the extent of expression of said at least one biomarker, and designing a kit comprising said means for determining the extent of expression.

The invention also provides for methods of designing kits comprising selecting at least one biomarker described herein, selecting detection agents for detecting said at least one biomarker, and designing a kit comprising said detection agents for detecting at least one biomarker.

The invention also provides kits comprising at least one biomarker described herein.

The invention also provides a kit comprising a means for determining the extent of expression of at least one polypeptide selected from the group consisting of SEQ ID NO: 12.

The invention also provides a kit comprising, detection agents for detecting at least one polypeptide selected from the group consisting of SEQ ID NO: 12.

The invention also provides a kit comprising, (a) means for determining the extent of expression of at least one polypeptide selected from the group consisting of SEQ ID NOS: 1-17, and (b) means for determining the extent of expression of at least one biomarker from anyone of Tables 1-12 or Tables 16-23.

The invention also provides a kit comprising, (a) detection agents for detecting at least one polypeptide selected from the group consisting of SEQ ID NOS: 1-17, and (b) detection agents for detecting at least one biomarker from anyone of Tables 1-12 or Tables 16-23.

The invention further provides for kits containing biomarkers and/or polypeptides from a plurality of the above Tables.

BRIEF DESCRIPTION OF THE DRAWINGS

FIG. 1A shows the average fluorescence intensity level of the biomarkers in the normal (NO) population from Example 1, as well as the standard deviation and relative standard deviation.

FIG. 1B shows the average fluorescence intensity level of the biomarkers in the non-small cell lung cancer (LC) population from Example 1, as well as the standard deviation and relative standard deviation.

FIG. 1C shows the average fluorescence intensity level of the biomarkers in the asthma (AST) population from Example 1, as well as the standard deviation and relative standard deviation.

FIG. 1D shows the percent change in the menu of fluorescence intensity for each of the biomarkers in the LC population v. NO population, AST population v. NO population, and the LC population v. AST population from Example 1.

FIG. 1E shows the probability associated with Student's t values obtained by comparing the mean fluorescence intensity and variability measured for each biomarker in the populations from Example 1, where the populations to be compared are LC population v. NO population, AST population v. NO population, and the LC population v. AST population, respectively.

FIG. 2A shows the average fluorescence intensity level of the biomarkers in the normal (NO) population from Example 2, as well as the standard deviation and relative standard deviation.

FIG. 2B shows the average fluorescence intensity level of the biomarkers in the non-small cell lung cancer (LC) population from Example 2, as well as the standard deviation and relative standard deviation.

FIG. 2C shows the average fluorescence intensity level of the biomarkers in the asthma (AST) population from Example 2, as well as the standard deviation and relative standard deviation.

FIG. 2D shows the percent change in the mean of fluorescence intensity for each of the biomarkers in the LC population v. NO population, AST population v. NO population, and the AST v. LC population from Example 2.

FIG. 2E shows the probability associated with Student's t values obtained by comparing the mean fluorescence intensity and variability measured for each biomarker in the populations from Example 2, where the populations to be compared are LC population v. NO population, AST population v. NO population, and the AST population v. LC population, respectively.

FIG. 3A shows the average fluorescence intensity level of the biomarkers in the normal (NO) population from Example 3, as well as the standard deviation and relative standard deviation.

FIG. 3B shows the average fluorescence intensity level of the biomarkers in the non-small cell lung cancer (LC) population from Example 3, as well as the standard deviation and relative standard deviation.

FIG. 3C shows the average fluorescence intensity level of the biomarkers in the asthma (AST)population from Example 3, as well as the standard deviation and relative standard deviation.

FIG. 3D shows the percent change in the mean of fluorescence intensity for each of the biomarkers in the AST population v. NO population, LC population v. NO populations, and the AST population v. LC population from Example 3.

FIG. 3E shows the probability associated with Student's t values obtained by comparing the mean fluorescence intensity and variability measured for each biomarker in the populations from Example 3, where the populations to be compared are AST population v. NO population, LC population v. NO population, and the AST v. LC population, respectively.

FIG. 4A shows the average fluorescence intensity level of the biomarkers in the normal (NO) female population from Example 3, as well as the standard deviation and relative standard deviation.

FIG. 4B shows the average fluorescence intensity level of the biomarkers in the non-small cell lung cancer (LC) female population from Example 3, as well as the standard deviation and relative standard deviation.

FIG. 4C shows the average fluorescence intensity level of the biomarkers in the asthma (AST) female population from Example 3, as well as the standard deviation and relative standard deviation.

FIG. 4D shows the percent change in the mean of fluorescence intensity for each of the biomarkers in the AST population v. NO female population, LC population v. NO female population, and the AST population v. LC female population from Example 3.

FIG. 4E shows the probability associated with Student's t values obtained by comparing the mean fluorescence intensity and variability measured for each biomarker in the female populations from Example 3, where the populations to be compared are AST population v. NO female population, LC population v. NO female population, and the AST population v. LC female population, respectively.

FIG. 5A shows the average fluorescence intensity level of the biomarkers in the normal (NO) male population from Example 3, as well as the standard deviation and relative standard deviation.

FIG. 5B shows the average fluorescence intensity level of the biomarkers in the non-small cell lung cancer (LC) male population from Example 3, as well as the standard deviation and relative standard deviation.

FIG. 5C shows the average fluorescence intensity level of the biomarkers in the asthma (AST) male population from Example 3, as well as the standard deviation and relative standard deviation.

FIG. 5D shows the percent change in the mean of fluorescence intensity for each of the biomarkers in the AST population v. NO male population, LC population v. NO male population, and the AST population v. LC male population Example 3.

FIG. 5E shows the probability associated with Student's t values obtained by comparing the mean fluorescence intensity and variability measured for each biomarker in the male populations from Example 3, where the populations to be compared are AST v. NO male populations, LC v. NO male populations, and the LC v. AST male populations, respectively.

FIG. 6A shows the percent change in the mean of fluorescence intensity for each of the biomarkers in the AST male population compared to the AST female population, the LC male population compared to the LC female population, and the NO male population compared to the NO female population from Example 3.

FIG. 6B shows the probability associated with Student's t values obtained by comparing the mean fluorescence intensity and variability measured for each biomarker in the male and female populations from Example 3, where the populations to be compared are the AST male and female populations, LC male and female populations, and the NO male and female populations, respectively.

FIG. 7A shows the percent change in the mean concentration of each of the biomarkers in the LC v. NO female populations, AST v. NO female populations, and the AST v. LC female populations of Example 3.

FIG. 7B shows the probability associated with the Kruskal-Wallis test calculated by comparing the concentration measured for each biomarker in the female populations of Example 3, where the populations to be compared are AST v. NO female populations, v. NO female populations, and the AST v. LC female populations, respectively.

FIG. 8A shows the percent change in the mean concentration of each of the biomarkers in the LC v. NO male populations, AST v. NO male populations, and the AST v. LC male populations of Example 3.

FIG. 8B shows the probability associated with the Kruskal-Wallis test calculated by comparing the concentration measured for each biomarker in the male populations of Example 3, where the populations to be compared are AST v. NO male populations, LC v. NO male populations, and the AST v. LC male populations, respectively.

DETAILED DESCRIPTION OF THE INVENTION

Figure 9:
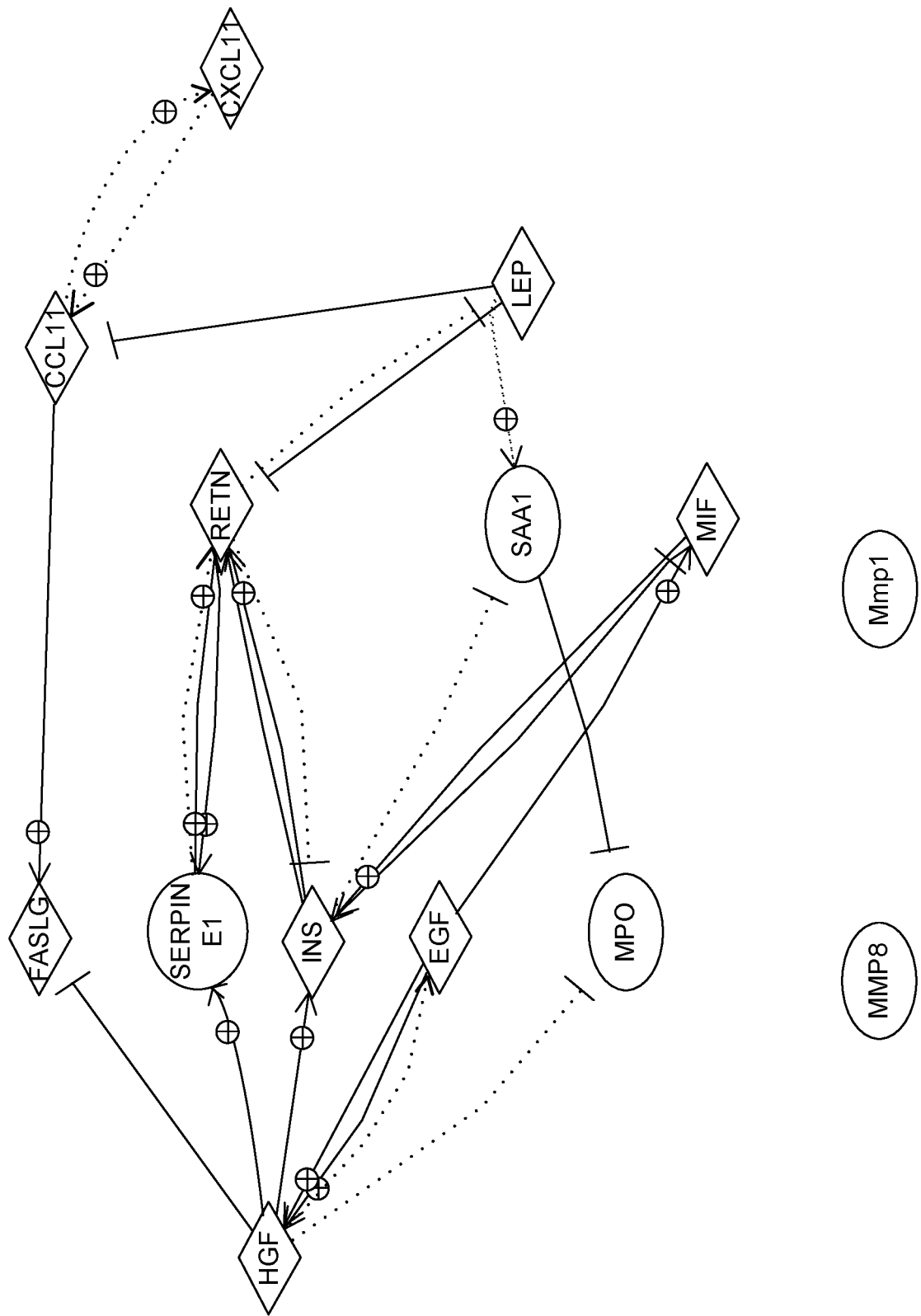
FIG. 9 shows relationships between the biomarkers of Table 16B.

The invention relates to various methods of detection, identification, assessment, prevention, diagnosis, and treatment of lung disease using biomarkers including gender-based disease detection, identification, assessment, prevention, and diagnosis, and treatment. These methods involve determining the extent of expression of specific biomarkers for which an altered expression is indicative of non-small cell lung cancer and/or reactive airway disease (e.g., asthma, chronic obstructive pulmonary disease, etc.). The invention also provides for various kits comprising detection agents for detecting these biomarkers, or means for determining the extent of expression of these biomarkers.

Definitions

As used herein, a "biomarker" or "marker" is a biological molecule that is objectively measured as a characteristic indicator of the physiological status of a biological system.

For purposes of the present disclosure biological molecules include ions, small molecules, peptides, proteins, peptides and proteins bearing post-translational modifications, nucleosides, nucleotides and polynucleotides including RNA and DNA, glycoproteins, lipoproteins, as well as various covalent and non-covalent modifications of these types of molecules. Biological molecules include any of these entities native to, characteristic of, and/or essential to the function of a biological system. The majority of biomarkers are polypeptides, although they may also be mRNA or modified mRNA which represents the pre-translation form of the gene product expressed as the polypeptide, or they may include post-translational modifications of the polypeptide.

As used herein, a "subject" means any animal, but is preferably a mammal, such as, for example, a human. In many embodiments, the subject will be a human patient having, or at-risk of having, a lung disease.

As used herein, a "physiological sample" includes samples from biological fluids and tissues. Biological fluids include whole blood, blood plasma, blood serum, sputum, urine, sweat, lymph, and alveolar lavage. Tissue samples include biopsies from solid lung tissue or other solid tissues, lymph node biopsy tissues, biopsies of metastatic foci. Method of obtaining physiological samples are well known.

As used herein, "therapeutic intervention" includes administration of one or more therapeutic agents such as a small molecule or macromolecule, radiation, surgery, or any combinations thereof.

As used herein, "detection agents" include reagents and systems that specifically detect the biomarkers described herein. Detection agents include reagents such as antibodies, nucleic acid probes, aptamers, lectins, or other reagents that have specific affinity for a particular marker or markers sufficient to discriminate between the particular marker and other markers which might be in samples of interest, and systems such as sensors, including sensors making use of bound or otherwise immobilized ligands as described above.

Identification of Biomarkers

The biomarkers of the invention were identified using two methods. First, identification of biomarkers indicative of non-small cell lung cancers and/or asthma was made by comparing the measured expression levels of fifty-nine selected biomarkers in the plasma of patients from populations who had been diagnosed with those respective pathologies to a population who had not been diagnosed with the pathologies, as confirmed by a physician. This method is detailed in Examples 1-3.

Second, biomarkers were identified using mass spectrometry. Identification of proteins indicative of non-small cell lung cancers and/or asthma was made by comparing the mass spectral data for tryptic peptide digests of samples obtained from patients in different physiological states. In particular, the data was the mass of peptide fragments, represented as graphical indications of the intensities of the pseudo or protonated molecular ion signals of peptides and proteins containing those fragments expressed across time in a single dimension. The expression levels of thousands of proteins were compared, resulting in the identification of seventeen proteins which were expressed in substantially differing intensities between populations of individuals not having any diagnosed lung tissue pathologies, populations of individuals having asthma, as diagnosed by a physician, and populations of individuals having non-small cell lung cancers, as diagnosed by a physician. This method is detailed in Examples 6 and 7.

First Order Interactors

To promote and control the multitude of cellular and organismal physiological functions necessary to maintain life, biological molecules must interact with each other. These interactions can be considered a type of communication. In this communication the various biological molecules can be considered messages. These molecules, as a necessary part of their signal transduction functions, necessarily interact with a broad variety of targets including other types of biological molecules.

One type of interacting molecule is commonly known as a receptor. Another type of direct intermolecular interaction is the binding of a co-factor to an enzyme. These intermolecular interactions form networks of signaling molecules that work together to carry out and control the essential life functions of cells and organisms. The particular biomarkers of this invention are linked physiologically to other biomarkers whose level increases or decreases in a fashion coordinated with the level of particular biomarkers. These other biomarkers are called "first order interactors" with respect to the particular biomarkers of the invention.

"First order interactors" are those molecular entities that interact directly with a particular biological molecule. For instance the drug morphine interacts directly with opiate receptors resulting ultimately in the diminishment of the sensation of pain. Thus, the opiate receptors are first order interactors under the definition of "first order interactor." First order interactors include both upstream and downstream direct neighbors for said biomarkers in the communication pathways in which they interact. These entities encompass proteins, nucleic acids and small molecules which may be connected by relationships that include but are not limited to direct (or indirect) regulation, expression, chemical reaction, molecular synthesis, binding, promoter binding, protein modification and molecular transport. Groups of biomarkers whose levels are coordinated are well known to those skilled in the art and those knowledgeable in physiology and cellular biology. Indeed, first order interactors for a particular biomarker are known in the art and can found using various databases and available bioinformatics software such as ARIADNE PATHWAY STUDIO, ExPASY Proteomics Server Qlucore Omics Explorer, Protein Prospector, PQuad, ChEMBL, and others. (see, e.g., ARIADNE PATHWAY STUDIO, Ariadne, Inc., <www.ariadne.genomics.com> or ChEMBL Database, European Bioinformatics Institute, European Molecular Biology Laboratory, <www.ebi.ac.uk>).

When the levels of the particular biomarkers of this invention are abnormal, levels of first order interactor biomarkers whose expression is coordinated with the particular biomarkers are also abnormal. Therefore, determination that levels of a particular biomarker are abnormal may be accomplished by measuring the level of a first order interactor coordinated therewith. The skilled person will of course confirm that the level of a first order interactor which is used in lieu or in addition to a particular biomarker will vary in a defined and reproducible way consistent with the behavior of the particular biomarker.

The invention provides that for any of the methods described herein, the methods to be performed with a particular biomarker may alternatively be performed with the first order interactors of that particular biomarker. For example, the invention provides for methods of physiological characterization comprising determining the extent of expression of HGF. As such, the invention also provides for methods of physiological characterization comprising determining the extent of expression of a first order interactor of HGF. The first order interactors of HGF include, but are not limited to those identified in Example 12.

Tables Identifying Significant Biomarkers

Table 1A lists biomarkers whose expression levels have a significant or marginally significant difference between at least one of AST v. NO populations, LC v. NO populations, and AST v. LC populations. Significance was determined as shown in Examples 1-3 using a Student's t test. Markers are listed in descending order based on the significance and magnitude of the difference in fluorescence intensity.

TABLE 1A

SIGNIFICANT BIOMARKERS FOR LUNG DISEASE

| No. | Biomarker |
|---|---|
| 1 | IL-13 |
| 2 | I-TAC |
| 3 | MCP-1 |
| 4 | MMP-1 |
| 5 | MPO |
| 6 | HGF |
| 7 | Eotaxin |
| 8 | MMP-9 |
| 9 | MMP-7 |
| 10 | IP-10 |
| 11 | SAA |
| 12 | Resistin |
| 13 | IL-5 |
| 14 | Leptin |
| 15 | sVCAM-1 |
| 16 | Adiponectin |
| 17 | CRP |
| 18 | C-Peptide |
| 19 | MMP-3 |
| 20 | SAP |
| 21 | IL-1ra |
| 22 | IL-15 |
| 23 | EGF |
| 24 | IL12 (p70) |
| 25 | MMP-8 |
| 26 | IL-8 |
| 27 | IL-6 |
| 28 | MMP-12 |
| 29 | PAI-1 |
| 30 | Amylin (Total) |
| 31 | IL-1α |
| 32 | sFSl |
| 33 | IL-4 |
| 34 | MIP-1β |
| 35 | IL-10 |
| 36 | SE-selectin |
| 37 | IL-17 |
| 38 | GM-CSF |
| 39 | G-CSF |
| 40 | TGF-α |
| 41 | IFN-γ |
| 42 | Fractalkine |
| 43 | VEGF |
| 44 | IL-7 |
| 45 | IL-12 (p40) |
| 46 | Sfas |
| 47 | MIF |
| 48 | IL-1β |
| 49 | IL-2 |
| 50 | MIP-1α |
| 51 | Insulin |
| 52 | GLP-1 |
| 53 | sCD40 ligand |

Table 1B lists biomarkers whose expression levels have a significant difference between the AST v. NO populations, LC v. NO populations, and AST v. LC populations. Significance was determined as shown in Examples 1-3 using a Student's t test. Marginally significant biomarkers are not included. Markers are listed in descending order based on the magnitude of the difference in fluorescence intensity.

TABLE 1B

SIGNIFICANT BIOMARKERS FOR LUNG DISEASE

| No. | Biomarker |
|---|---|
| 1 | IL-13 |
| 2 | I-TAC |
| 3 | MCP-1 |
| 4 | MMP-1 |
| 5 | MPO |
| 6 | HGF |
| 7 | Eotaxin |
| 8 | MMP-9 |
| 9 | MMP-7 |
| 10 | IP-10 |
| 11 | SAA |
| 12 | Resistin |
| 13 | IL-5 |
| 14 | Leptin |
| 15 | sVCAM-1 |
| 16 | Adiponectin |
| 17 | CRP |
| 18 | C-Peptide |
| 19 | MMP-3 |
| 20 | SAP |
| 21 | IL-1ra |
| 22 | IL-15 |

Table 1C lists biomarkers whose expression levels have a significant or marginally significant difference between the AST v. NO populations and LC v. NO populations. Significance was determined as shown in Examples 1-3 using a Student's t test. Markers are listed in descending order based on the magnitude of the difference in fluorescence intensity.

TABLE 1C

SIGNIFICANT BIOMARKERS FOR LUNG DISEASE

| No. | Biomarker |
|---|---|
| 1 | EGF |
| 2 | IL12 (p70) |
| 3 | IL-8 |
| 4 | IL-6 |
| 5 | MMP-12 |
| 6 | PAI-1 |
| 7 | Amylin (Total) |
| 8 | IL-4 |
| 9 | MIP-1β |
| 10 | IL-10 |
| 11 | SE-selectin |
| 12 | IL-17 |
| 13 | GM-CSF |
| 14 | G-CSF |
| 15 | TGF-α |
| 16 | IFN-γ |
| 17 | Fractalkine |
| 18 | VEGF |
| 19 | IL-12 (p40) |
| 20 | IL-7 |
| 21 | Insulin |

Table 2 lists biomarkers whose expression levels have a significant or marginally significant difference between the AST v. NO populations. Significance was determined as shown in Examples 1-3 using a Student's t test. Markers are listed in descending order based on the magnitude of the difference in fluorescence intensity.

TABLE 2

SIGNIFICANT BIOMARKERS INDICATIVE OF REACTIVE AIRWAY DISEASE

| No. | Biomarker |
|---|---|
| 1 | IL-13 |
| 2 | I-TAC |
| 3 | EGF |
| 4 | MCP-1 |
| 5 | HGF |
| 6 | MPO |
| 7 | IL12 (p70) |
| 8 | MMP-9 |
| 9 | IL-8 |
| 10 | Eotaxin |
| 11 | IL-6 |
| 12 | IP-10 |
| 13 | IL-1α |
| 14 | PAI-1 |
| 15 | Resistin |
| 16 | sFSl |
| 17 | IL-5 |
| 18 | Amylin (Total) |
| 19 | MMP-1 |
| 20 | MMP-12 |
| 21 | IL-4 |
| 22 | SAA |
| 23 | MMP-7 |
| 24 | IL-7 |
| 25 | sVCAM-1 |
| 26 | SE-selectin |
| 27 | Leptin |
| 28 | Adiponectin |
| 29 | IL-17 |
| 30 | CRP |
| 31 | GM-CSF |
| 32 | MIP-1β |
| 33 | TGF-α |
| 34 | IL-10 |
| 35 | Fractalkine |
| 36 | IFN-γ |
| 37 | C-Peptide |
| 38 | VEGF |
| 39 | G-CSF |
| 40 | IL-1ra |
| 41 | IL-15 |
| 42 | MMP-3 |
| 43 | IL-12 (p40) |
| 44 | SAP |
| 45 | Insulin |

Table 3 lists biomarkers whose expression levels have a significant or marginally significant difference between the LC v. NO populations. Significance was determined as shown in Examples 1-3 using a Student's t test. Markers are listed in descending order based on the magnitude of the difference in fluorescence intensity.

TABLE 3

SIGNIFICANT BIOMARKERS FOR NON-SMALL CELL LUNG CANCER (NSCLC)

| No. | Biomarker |
|---|---|
| 1 | IL-13 |
| 2 | EGF |
| 3 | I-TAC |
| 4 | MMP-1 |
| 5 | IL12 (p70) |
| 6 | Eotaxin |
| 7 | MMP-8 |
| 8 | MCP-1 |
| 9 | MPO |
| 10 | IP-10 |
| 11 | SAA |
| 12 | HGF |
| 13 | MMP-9 |
| 14 | MMP-12 |
| 15 | Amylin (Total) |
| 16 | PAI-1 |
| 17 | MMP-7 |
| 18 | IL-6 |
| 19 | MIP-1β |
| 20 | Adiponectin |
| 21 | IL-10 |
| 22 | CRP |
| 23 | Resistin |
| 24 | MIF |
| 25 | IL-5 |
| 26 | IL-4 |
| 27 | Leptin |
| 28 | SE-selectin |
| 29 | MIP-1α |
| 30 | C-Peptide |
| 31 | IL-1ra |
| 32 | SAP |
| 33 | G-CSF |
| 34 | IL-17 |
| 35 | MMP-3 |
| 36 | IFN-γ |
| 37 | TGF-α |
| 38 | sVCAM-1 |
| 39 | IL-15 |
| 40 | GM-CSF |
| 41 | Fractalkine |
| 42 | IL-1β |
| 43 | VEGF |
| 44 | GLP-1 |
| 45 | IL-7 |
| 46 | Insulin |
| 47 | IL-12 (p40) |
| 48 | IL-8 |

Table 4 lists biomarkers whose expression levels have a significant or marginally significant difference between the AST v. LC populations. Significance was determined as shown in Examples 1-3 using a Student's t test. Markers are listed in descending order based on the magnitude of the difference in fluorescence intensity.

TABLE 4

SIGNIFICANT BIOMARKERS DISTINGUISHING BETWEEN REACTIVE AIRWAY DISEASE AND NSCLC

| No. | Biomarker |
|---|---|
| 1 | MMP-7 |
| 2 | MMP-1 |
| 3 | SAA |
| 4 | MMP-8 |
| 5 | IL-8 |
| 6 | MCP-1 |
| 7 | Leptin |
| 8 | IL-1α |
| 9 | HGF |
| 10 | I-TAC |
| 11 | sVCAM-1 |
| 12 | MPO |
| 13 | sFSl |
| 14 | C-Peptide |
| 15 | IL-13 |
| 16 | Resistin |
| 17 | MMP-3 |
| 18 | IL-5 |
| 19 | SAP |
| 20 | Eotaxin |
| 21 | MMP-9 |

TABLE 4-continued

SIGNIFICANT BIOMARKERS DISTINGUISHING BETWEEN
REACTIVE AIRWAY DISEASE AND NSCLC

| No. | Biomarker |
|---|---|
| 22 | CRP |
| 23 | Adiponectin |
| 24 | IP-10 |
| 25 | IL-1ra |
| 26 | Sfas |
| 27 | IL-2 |
| 28 | IL-15 |
| 29 | IL12 (p70) |
| 30 | IL-6 |
| 31 | sCD40 ligand |
| 32 | VEGF |

Table 5A lists biomarkers whose expression levels have a significant or marginally significant difference between at least one of AST v. NO male populations, LC v. NO male populations, and AST v. LC male populations. Significance was determined as shown in Examples 1-3 using a Student's t test. Markers are listed in descending order based on the significance and magnitude of the difference in fluorescence intensity.

TABLE 5A

SIGNIFICANT BIOMARKERS FOR LUNG
DISEASE IN THE MALE POPULATION

| No. | Biomarker |
|---|---|
| 1 | I-TAC |
| 2 | MPO |
| 3 | HGF |
| 4 | MMP-1 |
| 5 | MMP-8 |
| 6 | Eotaxin |
| 7 | IL-8 |
| 8 | MMP-7 |
| 9 | PAI-1 |
| 10 | IP-10 |
| 11 | sVCAM-1 |
| 12 | IL-10 |
| 13 | Adiponectin |
| 14 | SAP |
| 15 | IFN-γ |
| 16 | IL-13 |
| 17 | EGF |
| 18 | MCP-1 |
| 19 | MIF |
| 20 | IL-12(p70) |
| 21 | MMP-9 |
| 22 | IL-6 |
| 23 | Amylin (Total) |
| 24 | SAA |
| 25 | IL-1α |
| 26 | TNF-α |
| 27 | IL-5 |
| 28 | Resistin |
| 29 | IL-1β |
| 30 | IL-7 |
| 31 | IL-4 |
| 32 | MIP-1β |
| 33 | Leptin |
| 34 | GM-CSF |
| 35 | G-CSF |
| 36 | TGF-α |
| 37 | IL-17 |
| 38 | CRP |
| 39 | IL-15 |
| 40 | VEGF |
| 41 | Fractalkine |
| 42 | MMP-3 |
| 43 | IL-12 (p40) |
| 44 | C-Peptide |
| 45 | IL-1ra |
| 46 | GLP-1 |
| 47 | MIP-1α |
| 48 | sFSl |
| 49 | Insulin |
| 50 | Sfas |
| 51 | SE-selectin |
| 52 | MMP-12 |

Table 5B lists biomarkers whose expression levels have a significant difference between the AST v. NO male populations, LC v. NO male populations, and AST v. LC male populations. Significance was determined as shown in Examples 1-3 using a Student's t test. Marginally significant biomarkers are not included. Markers are listed in descending order based on the magnitude of the difference in fluorescence intensity.

TABLE 5B

SIGNIFICANT BIOMARKERS FOR LUNG
DISEASE IN THE MALE POPULATION

| No. | Biomarker |
|---|---|
| 1 | I-TAC |
| 2 | MPO |
| 3 | HGF |
| 4 | MMP-1 |
| 5 | MMP-8 |
| 6 | Eotaxin |
| 7 | IL-8 |
| 8 | MMP-7 |
| 9 | PAI-1 |
| 10 | IP-10 |
| 11 | sVCAM-1 |
| 12 | IL-10 |
| 13 | Adiponectin |
| 14 | SAP |
| 15 | IFN-γ |

Table 5C lists biomarkers whose expression levels have a significant or marginally significant difference between the AST v. NO male populations and LC v. NO male populations. Significance was determined as shown in Examples 1-3 using a Student's t test. Markers are listed in descending order based on the magnitude of the difference in fluorescence intensity.

TABLE 5C

SIGNIFICANT BIOMARKERS FOR LUNG
DISEASE IN THE MALE POPULATION

| No. | Biomarker |
|---|---|
| 1 | IL-13 |
| 2 | EGF |
| 3 | MCP-1 |
| 4 | MIF |
| 5 | IL-12(p70) |
| 6 | MMP-9 |
| 7 | IL-6 |
| 8 | TNF-α |
| 9 | IL-5 |
| 10 | Resistin |
| 11 | IL-1β |
| 12 | IL-7 |

TABLE 5C-continued

SIGNIFICANT BIOMARKERS FOR LUNG
DISEASE IN THE MALE POPULATION

| No. | Biomarker |
|---|---|
| 13 | IL-4 |
| 14 | MIP-1β |
| 15 | Leptin |
| 16 | GM-CSF |
| 17 | G-CSF |
| 18 | TGF-α |
| 19 | IL-17 |
| 20 | IL-15 |
| 21 | VEGF |
| 22 | Fractalkine |
| 23 | IL-12 (p40) |
| 24 | MIP-1α |

Table 6 lists biomarkers whose expression levels have a significant or marginally significant difference between the AST v. NO male populations. Significance was determined as shown in Examples 1-3 using a Student's t test. Markers are listed in descending order based on the magnitude of the difference in fluorescence intensity.

TABLE 6

SIGNIFICANT BIOMARKERS FOR REACTIVE
AIRWAY DISEASE IN THE MALE POPULATION

| No. | Biomarker |
|---|---|
| 1 | IL-13 |
| 2 | I-TAC |
| 3 | MPO |
| 4 | HGF |
| 5 | EGF |
| 6 | MCP-1 |
| 7 | IL-8 |
| 8 | MIF |
| 9 | IL-6 |
| 10 | MMP-9 |
| 11 | IL-12(p70) |
| 12 | Eotaxin |
| 13 | IL-1α |
| 14 | PAI-1 |
| 15 | MMP-8 |
| 16 | TNF-α |
| 17 | IL-5 |
| 18 | MMP-1 |
| 19 | IL-1β |
| 20 | sFSl |
| 21 | Resistin |
| 22 | IL-7 |
| 23 | IL-4 |
| 24 | IP-10 |
| 25 | MIP-1β |
| 26 | GM-CSF |
| 27 | G-CSF |
| 28 | TGF-α |
| 29 | Leptin |
| 30 | IL-17 |
| 31 | sVCAM-1 |
| 32 | GLP-1 |
| 33 | IL-15 |
| 34 | MMP-7 |
| 35 | VEGF |
| 36 | IL-10 |
| 37 | Fractalkine |
| 38 | IL-12 (p40) |
| 39 | IFN-γ |
| 40 | Adiponectin |
| 41 | SE-selectin |
| 42 | SAP |
| 43 | MIP-1α |

Table 7 lists biomarkers whose expression levels have a significant or marginally significant difference between the LC v. NO male populations. Significance was determined as shown in Examples 1-3 using a Student's t test. Markers are listed in descending order based on the magnitude of the difference in fluorescence intensity.

TABLE 7

SIGNIFICANT BIOMARKERS FOR NSCLC
IN THE MALE POPULATION

| No. | Biomarker |
|---|---|
| 1 | IL-13 |
| 2 | I-TAC |
| 3 | EGF |
| 4 | MPO |
| 5 | HGF |
| 6 | MMP-1 |
| 7 | MMP-8 |
| 8 | MIF |
| 9 | Eotaxin |
| 10 | IL-12(p70) |
| 11 | MCP-1 |
| 12 | MMP-9 |
| 13 | PAI-1 |
| 14 | SAA |
| 15 | IP-10 |
| 16 | Amylin (Total) |
| 17 | MMP-7 |
| 18 | Resistin |
| 19 | IL-6 |
| 20 | MIP-1β |
| 21 | TNF-α |
| 22 | Leptin |
| 23 | IL-8 |
| 24 | IL-5 |
| 25 | CRP |
| 26 | IL-10 |
| 27 | Adiponectin |
| 28 | IL-7 |
| 29 | IL-4 |
| 30 | MMP-3 |
| 31 | G-CSF |
| 32 | MIP-1α |
| 33 | IL-17 |
| 34 | IFN-γ |
| 35 | IL-1ra |
| 36 | C-Peptide |
| 37 | TGF-α |
| 38 | IL-15 |
| 39 | Fractalkine |
| 40 | IL-1β |
| 41 | GM-CSF |
| 42 | sVCAM-1 |
| 43 | SAP |
| 44 | VEGF |
| 45 | IL-12 (p40) |
| 46 | Insulin |
| 47 | MMP-12 |

Table 8 lists biomarkers whose expression levels have a significant or marginally significant difference between the AST v. LC male populations. Significance was determined as shown in Examples 1-3 using a Student's t test. Markers are listed in descending order based on the magnitude of the difference in fluorescence intensity.

TABLE 8

SIGNIFICANT BIOMARKERS DISTINGUISHING
BETWEEN REACTIVE AIRWAY DISEASE AND
NSCLC IN THE MALE POPULATION

| No. | Biomarker |
|---|---|
| 1 | MMP-1 |
| 2 | MMP-8 |
| 3 | MMP-7 |
| 4 | Amylin (Total) |

TABLE 8-continued

SIGNIFICANT BIOMARKERS DISTINGUISHING BETWEEN REACTIVE AIRWAY DISEASE AND NSCLC IN THE MALE POPULATION

| No. | Biomarker |
|---|---|
| 5 | SAA |
| 6 | IL-8 |
| 7 | Insulin |
| 8 | IL-1α |
| 9 | sVCAM-1 |
| 10 | IP-10 |
| 11 | CRP |
| 12 | MPO |
| 13 | MMP-3 |
| 14 | Eotaxin |
| 15 | SAP |
| 16 | HGF |
| 17 | C-Peptide |
| 18 | I-TAC |
| 19 | Sfas |
| 20 | PAI-1 |
| 21 | IL-1ra |
| 22 | Adiponectin |
| 23 | IFN-γ |
| 24 | IL-10 |
| 25 | GLP-1 |
| 26 | IL-6 |
| 27 | IL-13 |
| 28 | IL-15 |

Table 9A lists biomarkers whose expression levels have a significant or marginally significant difference between at least one of AST v. NO female populations, LC v. NO female populations, and AST v. LC female populations. Significance was determined as shown in Examples 1-3 using a Student's t test. Markers are listed in descending order based on the significance and magnitude of the difference in fluorescence intensity.

TABLE 9A

SIGNIFICANT BIOMARKERS FOR LUNG DISEASE IN THE FEMALE POPULATION

| No. | Biomarker |
|---|---|
| 1 | I-TAC |
| 2 | Leptin |
| 3 | IP-10 |
| 4 | MMP-7 |
| 5 | SAA |
| 6 | MPO |
| 7 | Eotaxin |
| 8 | MMP-9 |
| 9 | Adiponectin |
| 10 | CRP |
| 11 | C-Peptide |
| 12 | sVCAM-1 |
| 13 | IL-15 |
| 14 | IL-1ra |
| 15 | IL-13 |
| 16 | EGF |
| 17 | IL-12(p70) |
| 18 | MCP-1 |
| 19 | MMP-1 |
| 20 | HGF |
| 21 | IL-8 |
| 22 | Resistin |
| 23 | sFSl |
| 24 | PAI-1 |
| 25 | MIF |
| 26 | SE-selectin |
| 27 | G-CSF |
| 28 | SAP |
| 29 | MMP-3 |
| 30 | GM-CSF |
| 31 | sICAM-1 |
| 32 | TNF-α |
| 33 | IL-10 |
| 34 | MIP-1β |
| 35 | IL-1α |
| 36 | sCD40 ligand |
| 37 | IL-6 |
| 38 | MMP-12 |
| 39 | MMP-2 |
| 40 | IL-5 |
| 41 | IL-4 |
| 42 | Sfas |
| 43 | MMP-8 |
| 44 | IL-1β |
| 45 | IL-12 (p40) |
| 46 | IL-2 |
| 47 | VEGF |
| 48 | TGF-α |
| 49 | IFN-γ |
| 50 | GLP-1 |
| 51 | Amylin (Total) |
| 52 | Insulin |

Table 9B lists biomarkers whose expression levels have a significant difference between the AST v. NO female populations, LC v. NO female populations, and AST v. LC female populations. Significance was determined as shown in Examples 1-3 using a Student's t test. Marginally significant biomarkers are not included. Markers are listed in descending order based on the magnitude of the difference in fluorescence intensity.

TABLE 9B

SIGNIFICANT BIOMARKERS FOR LUNG DISEASE IN THE FEMALE POPULATION

| No. | Biomarker |
|---|---|
| 1 | I-TAC |
| 2 | Leptin |
| 3 | IP-10 |
| 4 | MMP-7 |
| 5 | SAA |
| 6 | MPO |
| 7 | Eotaxin |
| 8 | MMP-9 |
| 9 | Adiponectin |
| 10 | CRP |
| 11 | C-Peptide |
| 12 | sVCAM-1 |
| 13 | IL-15 |
| 14 | IL-1ra |

Table 9C lists biomarkers whose expression levels have a significant or marginally significant difference between the AST v. NO female populations and LC v. NO female populations. Significance was determined as shown in Examples 1-3 using a Student's t test. Markers are listed in descending order based on the magnitude of the difference in fluorescence intensity.

TABLE 9C

SIGNIFICANT BIOMARKERS FOR LUNG DISEASE IN THE FEMALE POPULATION

| No. | Biomarker |
|---|---|
| 1 | IL-13 |
| 2 | EGF |
| 3 | IL-12(p70) |
| 4 | MCP-1 |
| 5 | PAI-1 |
| 6 | MIF |
| 7 | SE-selectin |
| 8 | G-CSF |
| 9 | GM-CSF |
| 10 | sICAM-1 |
| 11 | IL-2 |
| 12 | TGF-α |

Table 10 lists biomarkers whose expression levels have a significant or marginally significant difference between the AST v. NO female populations. Significance was determined as shown in Examples 1-3 using a Student's t test. Markers are listed in descending order based on the magnitude of the difference in fluorescence intensity.

TABLE 10

SIGNIFICANT BIOMARKERS FOR REACTIVE AIRWAY DISEASE IN THE FEMALE POPULATION

| No. | Biomarker |
|---|---|
| 1 | IL-13 |
| 2 | I-TAC |
| 3 | EGF |
| 4 | MCP-1 |
| 5 | Leptin |
| 6 | IL-12(p70) |
| 7 | IP-10 |
| 8 | MPO |
| 9 | HGF |
| 10 | MMP-9 |
| 11 | Eotaxin |
| 12 | SAA |
| 13 | Resistin |
| 14 | sFSl |
| 15 | PAI-1 |
| 16 | MMP-2 |
| 17 | MMP-7 |
| 18 | CRP |
| 19 | sCD40 ligand |
| 20 | MIF |
| 21 | SE-selectin |
| 22 | sVCAM-1 |
| 23 | IL-5 |
| 24 | C-Peptide |
| 25 | IL-4 |
| 26 | Adiponectin |
| 27 | Sfas |
| 28 | TNF-α |
| 29 | G-CSF |
| 30 | MIP-1β |
| 31 | MMP-3 |
| 32 | IL-15 |
| 33 | IL-12 (p40) |
| 34 | IL-2 |
| 35 | sICAM-1 |
| 36 | IL-1β |
| 37 | GM-CSF |
| 38 | IL-1ra |
| 39 | VEGF |
| 40 | GLP-1 |
| 41 | Amylin (Total) |
| 42 | IL-1α |
| 43 | Insulin |
| 44 | IL-6 |
| 45 | TGF-α |

Table 11 lists biomarkers whose expression levels have a significant or marginally significant difference between the LC v. NO female populations. Significance was determined as shown in Examples 1-3 using a Student's t test. Markers are listed in descending order based on the magnitude of the difference in fluorescence intensity.

TABLE 11

SIGNIFICANT BIOMARKERS FOR NSCLC IN THE FEMALE POPULATION

| No. | Biomarker |
|---|---|
| 1 | IL-13 |
| 2 | EGF |
| 3 | IL-12(p70) |
| 4 | I-TAC |
| 5 | SAA |
| 6 | IP-10 |
| 7 | MMP-1 |
| 8 | MCP-1 |
| 9 | Eotaxin |
| 10 | Leptin |
| 11 | MMP-9 |
| 12 | Adiponectin |
| 13 | MMP-7 |
| 14 | MPO |
| 15 | IL-8 |
| 16 | CRP |
| 17 | MMP-12 |
| 18 | MIF |
| 19 | SE-selectin |
| 20 | PAI-1 |
| 21 | SAP |
| 22 | IL-1ra |
| 23 | C-Peptide |
| 24 | sICAM-1 |
| 25 | sVCAM-1 |
| 26 | IL-15 |
| 27 | G-CSF |
| 28 | GM-CSF |
| 29 | IFN-γ |
| 30 | IL-2 |
| 31 | TGF-α |

Table 12 lists biomarkers whose expression levels have a significant or marginally significant difference between the AST v. LC female populations. Significance was determined as shown in Examples 1-3 using a Student's t test. Markers are listed in descending order based on the magnitude of the difference in fluorescence intensity.

TABLE 12

SIGNIFICANT BIOMARKERS DISTINGUISHING BETWEEN REACTIVE AIRWAY DISEASE AND NSCLC IN THE FEMALE POPULATION

| No. | Biomarker |
|---|---|
| 1 | MMP-7 |
| 2 | MMP-1 |
| 3 | IL-8 |
| 4 | IL-10 |
| 5 | SAA |

TABLE 12-continued

SIGNIFICANT BIOMARKERS DISTINGUISHING BETWEEN REACTIVE AIRWAY DISEASE AND NSCLC IN THE FEMALE POPULATION

| No. | Biomarker |
| --- | --- |
| 6 | HGF |
| 7 | I-TAC |
| 8 | Leptin |
| 9 | Resistin |
| 10 | sFSl |
| 11 | MPO |
| 12 | C-Peptide |
| 13 | sVCAM-1 |
| 14 | IL-1α |
| 15 | Adiponectin |
| 16 | MMP-8 |
| 17 | IL-15 |
| 18 | SAP |
| 19 | MMP-3 |
| 20 | MMP-9 |
| 21 | Eotaxin |
| 22 | IL-1ra |
| 23 | CRP |
| 24 | IP-10 |
| 25 | IL-6 |
| 26 | MIP-1β |
| 27 | IL-13 |
| 28 | IL-5 |
| 29 | PAI-1 |
| 30 | IFN-γ |

Table 13A lists biomarkers whose expression levels have a significant or marginally difference between male and female AST populations. Significance was determined as shown in Examples 1-3 using a Student's t test. Markers are listed in descending order based on the magnitude of the difference in fluorescence intensity.

TABLE 13A

BIOMARKERS WITH SIGNIFICANT DIFFERENCES BETWEEN MALE AND FEMALE REACTIVE AIRWAY DISEASE POPULATIONS

| No. | Biomarker |
| --- | --- |
| 1 | IL-6 |
| 2 | IL-1α |
| 3 | IL-5 |
| 4 | G-CSF |
| 5 | IL-4 |
| 6 | IL-7 |
| 7 | Leptin |
| 8 | GM-CSF |
| 9 | MIF |
| 10 | IL-15 |
| 11 | TGF-α |
| 12 | MIP-1β |
| 13 | MMP-1 |
| 14 | sCD40 ligand |
| 15 | MMP-2 |
| 16 | VEGF |
| 17 | IL-12 (p40) |
| 18 | Sfas |
| 19 | Resistin |
| 20 | I-TAC |
| 21 | IL-17 |
| 22 | HGF |
| 23 | MMP-9 |
| 24 | IP-10 |
| 25 | CRP |
| 26 | C-Peptide |
| 27 | sVCAM-1 |
| 28 | PAI-1 |
| 29 | SAP |
| 30 | IL-10 |

TABLE 13A-continued

BIOMARKERS WITH SIGNIFICANT DIFFERENCES BETWEEN MALE AND FEMALE REACTIVE AIRWAY DISEASE POPULATIONS

| No. | Biomarker |
| --- | --- |
| 31 | Fractalkine |
| 32 | Amylin (Total) |
| 33 | MPO |

Table 13B lists biomarkers whose expression levels have an insignificant difference between male and female AST populations. Significance was determined as shown in Examples 1-3 using a Student's t test. Markers are listed in descending order based on the magnitude of the difference in fluorescence intensity.

TABLE 13B

BIOMARKERS WITH INSIGNIFICANT DIFFERENCES BETWEEN MALE AND FEMALE REACTIVE AIRWAY DISEASE POPULATIONS

| No. | Biomarkers |
| --- | --- |
| 1 | Adiponectin |
| 2 | MMP-3 |
| 3 | IL-1ra |
| 4 | IFN-γ |
| 5 | SE-selectin |
| 6 | IL-2 |
| 7 | IL-13 |
| 8 | SAA |
| 9 | Eotaxin |
| 10 | sICAM-1 |
| 11 | EGF |
| 12 | MMP-7 |
| 13 | IL-12(p70) |
| 14 | MMP-12 |
| 15 | sFSl |
| 16 | IL-8 |
| 17 | MMP-13 |
| 18 | Insulin |
| 19 | MMP-8 |
| 20 | MCP-1 |
| 21 | GLP-1 |
| 22 | IL-1β |
| 23 | TNF-α |
| 24 | MIP-1α |

Table 14A lists biomarkers whose expression levels have a significant or marginally significant difference between male and female LC populations. Significance was determined as shown in Examples 1-3 using a Student's t test. Markers are listed in descending order based on the magnitude of the difference in fluorescence intensity.

TABLE 14A

BIOMARKERS WITH SIGNIFICANT DIFFERENCES BETWEEN MALE AND FEMALE NSCLC POPULATIONS

| No. | Biomarker |
| --- | --- |
| 1 | HGF |
| 2 | MMP-1 |
| 3 | Leptin |
| 4 | PAI-1 |
| 5 | Resistin |
| 6 | IP-10 |
| 7 | Adiponectin |
| 8 | MIF |
| 9 | IL-8 |
| 10 | IL-10 |

TABLE 14A-continued

BIOMARKERS WITH SIGNIFICANT DIFFERENCES
BETWEEN MALE AND FEMALE NSCLC POPULATIONS

| No. | Biomarker |
|---|---|
| 11 | MIP-1α |
| 12 | SAA |
| 13 | I-TAC |
| 14 | MMP-3 |
| 15 | IL-1β |

Table 14B lists biomarkers whose expression levels have an insignificant difference between male and female LC populations. Significance was determined as shown in Examples 1-3 using a Student's t test. Markers are listed in descending order based on the magnitude of the difference in fluorescence intensity.

TABLE 14B

BIOMARKERS WITH INSIGNIFICANT DIFFERENCES
BETWEEN MALE AND FEMALE NSCLC POPULATIONS

| No. | Biomarker |
|---|---|
| 1 | IL-15 |
| 2 | Eotaxin |
| 3 | Fractalkine |
| 4 | sICAM-1 |
| 5 | IL-1ra |
| 6 | GM-CSF |
| 7 | IL-12 (p40) |
| 8 | TGF-α |
| 9 | MPO |
| 10 | IL-13 |
| 11 | MMP-7 |
| 12 | IL-17 |
| 13 | IL-2 |
| 14 | SAP |
| 15 | IFN-γ |
| 16 | sVCAM-1 |
| 17 | CRP |
| 18 | MCP-1 |
| 19 | VEGF |
| 20 | C-Peptide |
| 21 | G-CSF |
| 22 | Sfas |
| 23 | IL-6 |
| 24 | SE-selectin |
| 25 | EGF |
| 26 | MMP-9 |
| 27 | Insulin |
| 28 | MMP-8 |
| 29 | GLP-1 |
| 30 | IL-5 |
| 31 | MMP-2 |
| 32 | IL-4 |
| 33 | MIP-1β |
| 34 | IL-12(p70) |
| 35 | sCD40 ligand |
| 36 | IL-1α |
| 37 | IL-7 |
| 38 | MMP-12 |
| 39 | TNF-α |
| 40 | Amylin (Total) |
| 41 | sFSl |
| 42 | MMP-13 |

Table 15A lists biomarkers ranked, in ascending order, by the relative standard deviation in fluorescence intensity for the normal population.

TABLE 15A

BIOMARKERS RANKED BY RELATIVE STANDARD
DEVIATION IN FLUORESCENCE INTENSITY
FOR THE NORMAL POPULATION

| No. | Biomarker |
|---|---|
| 1 | G-CSF |
| 2 | IL-15 |
| 3 | Fractalkine |
| 4 | TGF-α |
| 5 | SAP |
| 6 | IL-10 |
| 7 | VEGF |
| 8 | IL-12 (p40), free |
| 9 | sVCAM-1 |
| 10 | IL-17 |
| 11 | TNF-α |
| 12 | MMP-3 |
| 13 | IFN-γ |
| 14 | IL-1β |
| 15 | C-Peptide |
| 16 | IL-7 |
| 17 | GM-CSF |
| 18 | MIP-1β |
| 19 | sICAM-1 |
| 20 | MMP-7 |
| 21 | IL-4 |
| 22 | MCP-1 |
| 23 | Adiponectin |
| 24 | MIP-1α |
| 25 | Resistin |
| 26 | CRP |
| 27 | SE-selectin |
| 28 | IL-1ra |
| 29 | IL-5 |
| 30 | Eotaxin |
| 31 | PAI-1 |
| 32 | sFSl |
| 33 | Leptin |
| 34 | IL-6 |
| 35 | MMP-9 |
| 36 | IP-10 |
| 37 | Insulin |
| 38 | EGF |
| 39 | MMP-1 |
| 40 | GLP-1 |
| 41 | SAA |
| 42 | IL-1α |
| 43 | MIF |
| 44 | MMP-12 |
| 45 | Amylin (Total) |
| 46 | Sfas |
| 47 | MPO |
| 48 | IL-8 |
| 49 | sCD40 ligand |
| 50 | MMP-2 |
| 51 | HGF |
| 52 | MMP-13 |
| 53 | IL-2 |
| 54 | MMP-8 |
| 55 | IL12 p40 |
| 56 | IL-2 |
| 57 | I-TAC |

Table 15B lists biomarkers ranked, in ascending order, by the relative standard deviation in fluorescence intensity for the normal female population.

TABLE 15B

BIOMARKERS RANKED BY RELATIVE STANDARD
DEVIATION IN FLUORESCENCE INTENSITY
FOR THE NORMAL FEMALE POPULATION

| No. | Biomarker |
|---|---|
| 1 | G-CSF |
| 2 | IL-15 |

TABLE 15B-continued

BIOMARKERS RANKED BY RELATIVE STANDARD
DEVIATION IN FLUORESCENCE INTENSITY
FOR THE NORMAL FEMALE POPULATION

| No. | Biomarker |
|---|---|
| 3 | GM-CSF |
| 4 | IL-1ra |
| 5 | Fractalkine |
| 6 | IL-10 |
| 7 | IL-2 |
| 8 | TGF-α |
| 9 | VEGF |
| 10 | IL-12 (p40) |
| 11 | SAP |
| 12 | TNF-α |
| 13 | sVCAM-1 |
| 14 | IL-17 |
| 15 | MMP-3 |
| 16 | IL-7 |
| 17 | MIP-1β |
| 18 | C-Peptide |
| 19 | sICAM-1 |
| 20 | IFN-γ |
| 21 | MMP-7 |
| 22 | IL-1β |
| 23 | IL-4 |
| 24 | Adiponectin |
| 25 | Resistin |
| 26 | Sfas |
| 27 | MCP-1 |
| 28 | CRP |
| 29 | SE-selectin |
| 30 | MIP-1α |
| 31 | sFSl |
| 32 | Eotaxin |
| 33 | PAI-1 |
| 34 | IP-10 |
| 35 | IL-5 |
| 36 | MMP-2 |
| 37 | MMP-9 |
| 38 | IL-6 |
| 39 | MMP-1 |
| 40 | EGF |
| 41 | IL-12(p70) |
| 42 | MIF |
| 43 | Leptin |
| 44 | sCD40 ligand |
| 45 | HGF |
| 46 | Insulin |
| 47 | MPO |
| 48 | SAA |
| 49 | GLP-1 |
| 50 | IL-1α |
| 51 | MMP-8 |
| 52 | I-TAC |
| 53 | IL-8 |
| 54 | MMP-12 |
| 55 | IL-13 |
| 56 | Amylin (Total) |
| 57 | MMP-13 |

Table 15C lists biomarkers ranked, in ascending order, by the relative standard deviation in fluorescence intensity for the normal male population.

TABLE 15C

BIOMARKERS RANKED BY RELATIVE STANDARD
DEVIATION IN FLUORESCENCE INTENSITY
FOR THE NORMAL MALE POPULATION

| No. | Biomarker |
|---|---|
| 1 | IL-1β |
| 2 | IL-15 |
| 3 | G-CSF |
| 4 | MIP-1α |

TABLE 15C-continued

BIOMARKERS RANKED BY RELATIVE STANDARD
DEVIATION IN FLUORESCENCE INTENSITY
FOR THE NORMAL MALE POPULATION

| No. | Biomarker |
|---|---|
| 5 | TGF-α |
| 6 | Fractalkine |
| 7 | SAP |
| 8 | IFN-γ |
| 9 | IL-10 |
| 10 | sVCAM-1 |
| 11 | TNF-α |
| 12 | VEGF |
| 13 | IL-12 (p40) |
| 14 | MCP-1 |
| 15 | MIP-1β |
| 16 | C-Peptide |
| 17 | MMP-3 |
| 18 | IL-17 |
| 19 | IL-7 |
| 20 | sICAM-1 |
| 21 | MIF |
| 22 | GM-CSF |
| 23 | MMP-7 |
| 24 | IL-4 |
| 25 | Adiponectin |
| 26 | SE-selectin |
| 27 | CRP |
| 28 | Resistin |
| 29 | MMP-8 |
| 30 | HGF |
| 31 | Leptin |
| 32 | IL-5 |
| 33 | Eotaxin |
| 34 | MMP-9 |
| 35 | IL-1ra |
| 36 | PAI-1 |
| 37 | sFSl |
| 38 | IL-6 |
| 39 | Insulin |
| 40 | EGF |
| 41 | Amylin (Total) |
| 42 | MMP-1 |
| 43 | IL-8 |
| 44 | IP-10 |
| 45 | SAA |
| 46 | GLP-1 |
| 47 | MMP-12 |
| 48 | IL-1α |
| 49 | MMP-13 |
| 50 | sCD40 ligand |
| 51 | MMP-2 |
| 52 | Sfas |
| 53 | MPO |
| 54 | IL-2 |
| 55 | I-TAC |
| 56 | IL-12(p70) |
| 57 | IL-13 |

Table 16A lists biomarkers whose expression levels have a significant difference between at least one of AST v. NO male populations, LC v. NO male populations, and AST v. LC male populations. Significance was determined as shown in Example 4 using the Kruskal-Wallis method. Marginally significant biomarkers are not included. Markers are listed in descending order based on the significance and magnitude of the difference in fluorescence intensity.

TABLE 16A

SIGNIFICANT BIOMARKERS FOR LUNG
DISEASE IN THE MALE POPULATION

| No. | Biomarker |
|---|---|
| 1 | HGF |
| 2 | MMP-8 |

TABLE 16A-continued

SIGNIFICANT BIOMARKERS FOR LUNG DISEASE IN THE MALE POPULATION

| No. | Biomarker |
|---|---|
| 3 | I-TAC |
| 4 | EGF |
| 5 | PAI-1 |
| 6 | MMP-1 |
| 7 | MPO |
| 8 | MIF |
| 9 | Eotaxin |
| 10 | MMP-12 |
| 11 | SAA |
| 12 | Resistin |
| 13 | sFSl |
| 14 | Leptin |
| 15 | C-Peptide |
| 16 | MMP-9 |
| 17 | MCP-1 |
| 18 | MMP-3 |
| 19 | MIP-1α |
| 20 | MMP-13 |
| 21 | G-CSF |
| 22 | IFN-γ |
| 23 | MMP-7 |
| 24 | IP-10 |
| 25 | CRP |
| 26 | Insulin |
| 27 | VEGF |
| 28 | SAP |
| 29 | Adiponectin |
| 30 | sVCAM-1 |
| 31 | Sfas |
| 32 | IL-1ra |
| 33 | IL-12 (p40) |
| 34 | MIP-1β |
| 35 | sICAM-1 |

Table 16B lists biomarkers whose expression levels have a significant difference between the AST v. NO male populations, LC v. NO male populations, and AST v. LC male populations. Significance was determined as shown in Example 4 using the Kruskal-Wallis method. Marginally significant biomarkers are not included. Markers are listed in descending order based on the magnitude of the difference in fluorescence intensity.

TABLE 16B

SIGNIFICANT BIOMARKERS FOR LUNG DISEASE IN THE MALE POPULATION

| No. | Biomarker |
|---|---|
| 1 | HGF |
| 2 | MMP-8 |
| 3 | I-TAC |
| 4 | EGF |
| 5 | PAI-1 |
| 6 | MMP-1 |
| 7 | MPO |
| 8 | MIF |
| 9 | Eotaxin |
| 10 | MMP-12 |
| 11 | SAA |
| 12 | Resistin |
| 13 | sFSl |
| 14 | Leptin |
| 15 | C-Peptide |

Table 16C lists biomarkers whose expression levels have a significant difference between the AST v. NO male populations and LC NO male populations. Significance was determined as shown in Example 4 using the Kruskal-Wallis method. Marginally significant biomarkers are not included. Markers are listed in descending order based on the magnitude of the difference in fluorescence intensity.

TABLE 16C

SIGNIFICANT BIOMARKERS FOR LUNG DISEASE IN THE MALE POPULATION

| No. | Biomarker |
|---|---|
| 1 | HGF |
| 2 | MMP-8 |
| 3 | I-TAC |
| 4 | MMP-9 |
| 5 | EGF |
| 6 | PAI-1 |
| 7 | MMP-1 |
| 8 | MPO |
| 9 | MIF |
| 10 | MCP-1 |
| 11 | Eotaxin |
| 12 | MMP-3 |
| 13 | MIP-1α |
| 14 | MMP-12 |
| 15 | MMP-13 |
| 16 | IP-10 |
| 17 | VEGF |
| 18 | Resistin |
| 19 | sFSl |
| 20 | C-Peptide |
| 21 | Sfas |
| 22 | SAA |
| 23 | Insulin |
| 24 | SAP |
| 25 | Leptin |

Table 17 lists biomarkers whose expression levels have a significant difference between the AST v. NO male populations. Significance was determined as shown in Example 4 using the Kruskal-Wallis method. Marginally significant biomarkers are not included. Markers are listed in descending order based on the magnitude of the difference in fluoresce intensity.

TABLE 17

SIGNIFICANT BIOMARKERS FOR REACTIVE AIRWAY DISEASE IN THE MALE POPULATION

| No. | Biomarker |
|---|---|
| 1 | HGF |
| 2 | I-TAC |
| 3 | EGF |
| 4 | MMP-8 |
| 5 | PAI-1 |
| 6 | MPO |
| 7 | MMP-9 |
| 8 | MCP-1 |
| 9 | MIP-1α |
| 10 | Eotaxin |
| 11 | MMP-1 |
| 12 | MIF |
| 13 | MMP-3 |
| 14 | MMP-12 |
| 15 | IP-10 |
| 16 | sFSl |
| 17 | MMP-13 |
| 18 | VEGF |
| 19 | C-Peptide |
| 20 | Resistin |
| 21 | sVCAM-1 |
| 22 | G-CSF |
| 23 | Sfas |
| 24 | sICAM-1 |
| 25 | Leptin |
| 26 | SAP |
| 27 | Insulin |

TABLE 17-continued

SIGNIFICANT BIOMARKERS FOR REACTIVE
AIRWAY DISEASE IN THE MALE POPULATION

| No. | Biomarker |
|---|---|
| 28 | IFN-γ |
| 29 | SAA |

Table 18 lists biomarkers whose expression levels have a significant difference between the LC v. NO male populations. Significance was determined as shown in Example 4 using the Kruskal-Wallis method. Marginally significant biomarkers are not included. Markers are listed in descending order based on the magnitude of the difference in fluorescence intensity.

TABLE 18

SIGNIFICANT BIOMARKERS FOR NSCLC
IN THE MALE POPULATION

| No. | Biomarker |
|---|---|
| 1 | HGF |
| 2 | MMP-8 |
| 3 | MMP-9 |
| 4 | I-TAC |
| 5 | EGF |
| 6 | MMP-1 |
| 7 | PAI-1 |
| 8 | MPO |
| 9 | MIF |
| 10 | MMP-3 |
| 11 | MMP-12 |
| 12 | Eotaxin |
| 13 | MMP-13 |
| 14 | MCP-1 |
| 15 | MIP-1α |
| 16 | IP-10 |
| 17 | MMP-7 |
| 18 | Resistin |
| 19 | CRP |
| 20 | VEGF |
| 21 | SAA |
| 22 | Adiponectin |
| 23 | IL-1ra |
| 24 | Sfas |
| 25 | MIP-1β |
| 26 | sFSl |
| 27 | C-Peptide |
| 28 | Insulin |
| 29 | SAP |
| 30 | Leptin |
| 31 | IL-12 (p40) |
| 32 | |

Table 19 lists biomarkers whose expression levels have a significant difference between the AST v. LC male populations. Significance was determined as shown in Example 4 using the Kruskal-Wallis method. Marginally significant biomarkers are not included. Markers are listed in descending order based on the magnitude of the difference in fluorescence intensity.

TABLE 19

SIGNIFICANT BIOMARKERS DISTINGUISHING
BETWEEN REACTIVE AIRWAY DISEASE AND
NSCLC IN THE MALE POPULATION

| No. | Biomarker |
|---|---|
| 1 | I-TAC |
| 2 | HGF |
| 3 | MPO |
| 4 | sFSl |
| 5 | PAI-1 |
| 6 | C-Peptide |
| 7 | sVCAM-1 |
| 8 | Eotaxin |
| 9 | EGF |
| 10 | Leptin |
| 11 | MIF |
| 12 | Resistin |
| 13 | Adiponectin |
| 14 | MMP-12 |
| 15 | MMP-7 |
| 16 | CRP |
| 17 | G-CSF |
| 18 | IFN-γ |
| 19 | SAA |
| 20 | MMP-1 |
| 21 | MMP-8 |
| 22 | |

Table 20A lists biomarkers whose expression levels have a significant difference between at least one of AST v. NO female populations, LC v. NO female populations, and AST v. LC female populations. Significance was determined as shown in Example 4 using the Kruskal-Wallis method. Marginally significant biomarkers are not included. Markers are listed in descending order based on the significance and magnitude of the difference in fluorescence intensity.

TABLE 20A

SIGNIFICANT BIOMARKERS FOR LUNG
DISEASE IN THE FEMALE POPULATION

| No. | Biomarker |
|---|---|
| 1 | I-TAC |
| 2 | PAI-1 |
| 3 | MMP-7 |
| 4 | MMP-3 |
| 5 | IL-8 |
| 6 | MPO |
| 7 | Leptin |
| 8 | sFSl |
| 9 | HGF |
| 10 | Resistin |
| 11 | C-Peptide |
| 12 | MMP-13 |
| 13 | SAP |
| 14 | sVCAM-1 |
| 15 | MMP-8 |
| 16 | IL-10 |
| 17 | MMP-9 |
| 18 | G-CSF |
| 19 | EGF |
| 20 | MCP-1 |
| 21 | SAA |
| 22 | MMP-1 |
| 23 | Fractalkine |
| 24 | IL-1α |
| 25 | CRP |
| 26 | MIP-1β |
| 27 | IP-10 |
| 28 | IL-1ra |
| 29 | MIP-1α |
| 30 | VEGF |
| 31 | IFN-γ |
| 32 | Adiponectin |
| 33 | Eotaxin |
| 34 | IL-6 |

TABLE 20A-continued

SIGNIFICANT BIOMARKERS FOR LUNG
DISEASE IN THE FEMALE POPULATION

| No. | Biomarker |
|---|---|
| 35 | MMP-12 |
| 36 | sICAM-1 |
| 37 | MIF |
| 38 | Sfas |
| 39 | IL-12 (p40) |
| 40 | IL-4 |
| 41 | Insulin |

Table 20B lists biomarkers whose expression levels have a significant difference between the AST v. NO female populations, LC v. NO female populations, and AST v. LC female populations. Significance was determined as shown in Example 4 using the Kruskal-Wallis method. Marginally significant biomarkers are not included. Markers are listed in descending order based on the magnitude of the difference in fluorescence intensity.

TABLE 20B

SIGNIFICANT BIOMARKERS FOR LUNG
DISEASE IN THE FEMALE POPULATION

| No. | Biomarker |
|---|---|
| 1 | I-TAC |
| 2 | PAI-1 |
| 3 | MMP-7 |
| 4 | MMP-3 |
| 5 | IL-8 |
| 6 | MPO |
| 7 | Leptin |
| 8 | sFSl |
| 9 | HGF |
| 10 | Resistin |
| 11 | C-Peptide |
| 12 | MMP-13 |
| 13 | SAP |
| 14 | sVCAM-1 |
| 15 | MMP-8 |

Table 20C lists biomarkers whose expression levels have a significant difference between the AST v. NO female populations and LC v. NO female populations. Significance was determined as shown in Example 4 using the Kruskal-Wallis method. Marginally significant biomarkers are not included. Markers are listed in descending order based on the magnitude of the difference in fluorescence intensity.

TABLE 20C

SIGNIFICANT BIOMARKERS FOR LUNG
DISEASE IN THE FEMALE POPULATION

| No. | Biomarker |
|---|---|
| 1 | MMP-9 |
| 2 | G-CSF |
| 3 | I-TAC |
| 4 | EGF |
| 5 | MCP-1 |
| 6 | PAI-1 |
| 7 | SAA |
| 8 | MPO |
| 9 | MMP-3 |
| 10 | CRP |
| 11 | IP-10 |
| 12 | Leptin |
| 13 | sFSl |

TABLE 20C-continued

SIGNIFICANT BIOMARKERS FOR LUNG
DISEASE IN THE FEMALE POPULATION

| No. | Biomarker |
|---|---|
| 14 | IFN-γ |
| 15 | Adiponectin |
| 16 | Eotaxin |
| 17 | HGF |
| 18 | IL-8 |
| 19 | Resistin |
| 20 | IL-6 |
| 21 | Sfas |
| 22 | C-Peptide |
| 23 | MMP-7 |
| 24 | sVCAM-1 |
| 25 | sICAM-1 |
| 26 | MMP-8 |
| 27 | MIF |
| 28 | MMP-13 |
| 29 | SAP |
| 30 | MIP-1α |
| 31 | VEGF |
| 32 | IL-1ra |

Table 21 lists biomarkers whose expression levels have a significant difference between the AST v. NO female populations. Significance was determined as shown in Example 4 using the Kruskal-Wallis method. Marginally significant biomarkers are not included. Markers are listed in descending order based on the magnitude of the difference in fluorescence intensity.

TABLE 21

SIGNIFICANT BIOMARKERS FOR REACTIVE AIRWAY
DISEASE IN THE FEMALE POPULATION

| No. | Biomarker |
|---|---|
| 1 | MMP-9 |
| 2 | I-TAC |
| 3 | EGF |
| 4 | PAI-1 |
| 5 | MCP-1 |
| 6 | G-CSF |
| 7 | IL-1α |
| 8 | MPO |
| 9 | IL-8 |
| 10 | Leptin |
| 11 | sFSl |
| 12 | HGF |
| 13 | IP-10 |
| 14 | Resistin |
| 15 | IFN-γ |
| 16 | SAA |
| 17 | CRP |
| 18 | Adiponectin |
| 19 | Eotaxin |
| 20 | C-Peptide |
| 21 | IL-6 |
| 22 | sVCAM-1 |
| 23 | IL-4 |
| 24 | MMP-3 |
| 25 | Sfas |
| 26 | MMP-8 |
| 27 | sICAM-1 |
| 28 | MIF |
| 29 | MMP-13 |
| 30 | SAP |
| 31 | MMP-7 |
| 32 | MIP-1α |
| 33 | VEGF |
| 34 | IL-1ra |

Table 22 lists biomarkers whose expression levels have a significant difference between the LC v. NO female populations. Significance was determined as shown in Example 4 using the Kruskal-Wallis method. Marginally significant biomarkers are not included. Markers are listed in descending order based on the magnitude of the difference in fluorescence intensity.

TABLE 22

SIGNIFICANT BIOMARKERS FOR NSCLC IN THE FEMALE POPULATION

| No. | Biomarker |
|---|---|
| 1 | MMP-9 |
| 2 | G-CSF |
| 3 | EGF |
| 4 | IL-10 |
| 5 | MCP-1 |
| 6 | SAA |
| 7 | MMP-3 |
| 8 | PAI-1 |
| 9 | I-TAC |
| 10 | CRP |
| 11 | MMP-1 |
| 12 | MPO |
| 13 | IP-10 |
| 14 | Adiponectin |
| 15 | MMP-7 |
| 16 | Eotaxin |
| 17 | IFN-γ |
| 18 | Leptin |
| 19 | MMP-12 |
| 20 | IL-6 |
| 21 | Sfas |
| 22 | sICAM-1 |
| 23 | Resistin |
| 24 | MMP-8 |
| 25 | sFSl |
| 26 | sVCAM-1 |
| 27 | Fractalkine |
| 28 | HGF |
| 29 | MIF |
| 30 | MMP-13 |
| 31 | C-Peptide |
| 32 | SAP |
| 33 | Insulin |
| 34 | IL-8 |
| 35 | MIP-1α |
| 36 | MIP-1β |
| 37 | VEGF |
| 38 | IL-1ra |

Table 23 lists biomarkers whose expression levels have a significant difference between the AST v. LC female populations. Significance was determined as shown in Example 4 using the Kruskal-Wallis method. Marginally significant biomarkers are not included. Markers are listed in descending order based on the magnitude of the difference in fluorescence intensity.

TABLE 23

SIGNIFICANT BIOMARKERS DISTINGUISHING BETWEEN REACTIVE AIRWAY DISEASE AND NSCLC IN THE FEMALE POPULATION

| No. | Biomarker |
|---|---|
| 1 | IL-8 |
| 2 | HGF |
| 3 | sFSl |
| 4 | I-TAC |
| 5 | C-Peptide |
| 6 | IL-1α |
| 7 | Resistin |
| 8 | IL-12 (p40) |
| 9 | Leptin |
| 10 | sVCAM-1 |

TABLE 23-continued

SIGNIFICANT BIOMARKERS DISTINGUISHING BETWEEN REACTIVE AIRWAY DISEASE AND NSCLC IN THE FEMALE POPULATION

| No. | Biomarker |
|---|---|
| 11 | PAI-1 |
| 12 | MPO |
| 13 | MMP-8 |
| 14 | MMP-12 |
| 15 | SAP |
| 16 | MMP-13 |
| 17 | MIP-1β |
| 18 | MMP-1 |
| 19 | MMP-3 |
| 20 | Fractalkine |
| 21 | MMP-7 |
| 22 | IL-10 |

Determining the Extent of Expression

Extent of expression generally relates to a quantitative measurement of an expression product which is typically a protein or polypeptide. The invention contemplates determining the extent of expression at the RNA (pre-transitional) or protein level (which may include post-translational modification). In particular, the invention contemplates determining changes in biomarker concentrations reflected in an increase or decrease in the level of transcription, translation, post-transcriptional modification, or the extent or degree of degradation of protein, where these changes are associated with a particular disease state or disease progression.

Samples are collected to ensure that the extent of expression in a subject is proportional to the concentration of said biomarker in the sample. Measurements are made so that the measured value is proportional to the concentration of the biomarker in the sample. Thus, the measured value is proportional to the extent of expression. Selecting sampling techniques and measurement techniques which meet these requirements is within the skill of the art.

Typically, the extent of expression of at least one biomarker indicative of a lung disease is a level of at least one biomarker that differs by a statistically significant degree from the average expression level in normal individuals; in other words, at least one biomarker is statistically deviant from the normal. Statistical significance and deviation may be determined using any known method for comparing means of populations or comparing a measured value to the mean value for a population. Such methods include the Student's t tests for single and multiple markers considered together, analysis of variance (ANOVA), etc.

As an alternative to, or in combination with determining the extent of expression, methods described herein involve determining whether the level of a biomarker falls within a normal level (e.g., range) or is outside the normal level (i.e. abnormal). Those who measure levels of biological molecules in physiological samples routinely determine the normal level of a particular biomarkers in the population they regularly measure, typically described as the normal range of values as determined by the particular laboratory. Thus, the skilled person will inevitable be familiar with normal levels of a particular biomarker and can determine whether the level of the biomarker is outside of the normal level or range.

More typically, the extent of expression of at least one biomarker indicative of a lung disease is a level of at least one biomarker also differs by a magnitude sufficient such that the differences are analytically significant from the average expression level in normal individuals such that a diagnosis, prognosis, and/or assessment of a lung disease may be determined. Those of skill in the art understand that greater differences in magnitude are preferred to assist in the diagnosis, prognosis, and/or assessment of a lung disease. See Instrumental Methods of Analysis, Seventh Edition, 1988.

Many proteins expressed by a normal subject will be expressed to a greater or lesser extent in subjects having a disease or condition, such as non-small cell lung cancer or asthma. One of skill in the art will appreciate that most diseases manifest changes in multiple, different biomarkers. As such, disease may be characterized by a pattern of expression a plurality of markers. Indeed, changes in a pattern of expression for a plurality of biomarkers may be used in various diagnostic and prognostic methods, as well as monitoring, therapy selection, and patient assessment methods. The invention provides for such methods. These methods comprise determining a pattern of expression of a plurality of markers for a particular physiologic state, or determining changes in such a pattern which correlate to changes in physiologic state, as characterized by any technique for suitable pattern recognition.

Numerous methods of determining the extent of expression are known in the art. Means for determining expression include but are not limited to radio-immuno assay, enzyme-linked immunosorbent assay (ELISA), high pressure liquid chromatography with radiometric or spectrometric detection via absorbance of visible or ultraviolet light, mass spectrometric qualitiative and quantitative analysis, western blotting, 1 or 2 dimensional gel electrophoresis with quantitative visualization by means of detection radioactive, fluorescent or chemiluminescent probes or nuclei, antibody-based detection with absorptive or fluorescent photometry, quantitation by luminescence of any of a number of chemiluminescent reporter systems, enzymatic assays, immunoprecipitation or immuno-capture assays, solid and liquid phase immunoassays, protein arrays or chips, DNA arrays or chips, plate assays, assays that use molecules having binding affinity that permit discrimination such as aptamers and molecular imprinted polymers, and any other quantitative analytical determination of the concentration of a biomarker by any other suitable technique, instrumental actuation of any of the described detection techniques or instrumentation.

The step of determining the extent of expression may be performed by any means for determining expression known in the art, especially those means discussed herein. In preferred embodiments, the step of determining the extent of expression comprises performing an immunoassays with antibodies.

Selection of Biomarkers for Determination

One of skill in the art would readily be able to select appropriate antibodies for use in the present invention. The antibody chosen is preferably selective for an antigen of interest, possesses a high binding specificity for said antigen, and has minimal cross-reactivity with other antigens. The ability of an antibody to bind to an antigen of interest may be determined, for example, by known methods such as enzyme-linked immunosorbent assay (ELISA), flow cytometry, and immunohistochemistry. Preferably, the antigen of interest to which the antibody binds is differentially present in cells or biological samples taken from diseased patients as opposed to cells or biological samples taken from healthy patients. The differential presence of the antigen in different populations may be determined by comparing the binding of the antibody to samples taken from each of the populations of interest (e.g., the diseased population versus the healthy population). See, e.g., Examples 1-4; see also FIGS. 1-8. For example, the antigen of interest may be determined to be expressed at higher levels in cancer cells than in non-cancer cells. See, e.g., Examples 1-4; see also FIGS. 1-8. Furthermore, the antibody should have a relatively high binding specificity for the antigen of interest. The binding specificity of the antibody may be determined by known methods such as immunoprecipitation or by an in vitro binding assay, such as radioimmunoassay (RIA) or ELISA. Disclosure of methods for selecting antibodies capable of binding antigens of interest with high binding specificity and minimal cross-reactivity are provided, for example, in U.S. Pat. No. 7,288,249, which is hereby incorporated by reference in its entirety.

The invention provides for various methods comprising the step of determining the extent of expression of one or more biomarkers described herein. In one embodiment, the method comprises determining the extent of expression of any of the biomarkers from any number of Tables 1-14 or 16-23. The biomarkers in Tables 1-14 and 16-23 are generally listed in decreasing order of the extent of expression. The biomarkers closer to the top of these Tables generally show more sensitivity (e.g., detect differences at lower levels). Using such biomarkers may assist in discriminating between disease conditions. The biomarkers in Table 15 are listed in ascending order based on the relative standard deviation in fluorescence intensity. The biomarkers closer to the top of Table 15 are also generally more sensitive due to a lower degree of variance other than the variance which is due to the presence of a disease state. In particular, these biomarkers have less overall variability and thus are helpful in reducing background noise when comparing the extent of expression of diseased individuals as compared to the extent of expression in normal individuals.

Consequently, a preferred method comprises determining the extent of expression of biomarker nos. 1-20 of a particular Table, or the total list of biomarkers if the Table contains less than 20. Alternatively, this mode comprises determining the extent of expression of biomarker nos. 1-10, more preferably biomarker nos. 1-8 even more preferably biomarker nos. 1-6, and most preferably biomarker nos. 1-4, or a subset of the biomarkers in any of these groups. In another embodiment, the method composes determining the extent of expression of any combination of biomarkers from a particular Table. In another embodiment, the method comprises determining the extent of expression of any combination of a plurality of biomarkers from biomarker nos. 1-20 (or the maximum list if less than 20) of a particular Table, preferably any combination of a plurality of biomarkers from biomarker nos. 1-10, more preferably any combination of a plurality of biomarkers from biomarker nos. 1-8, even more preferably any combination of biomarkers from biomarker nos. 1-6, and most preferably any combination of a plurality of biomarkers from biomarker nos. 1-4, or a subset of the biomarkers in any of these groups. In a preferred mode, the method comprises determining the extent of expression of any of a particular subset of three biomarkers selected from biomarker nos. 1-6, 1-8, 1-10, 1-15, or 1-20 of a particular Table. Alternatively, the method comprises determining the extent of expression of any of a particular subset of four, five, six or seven biomarkers selected from biomarker nos. 1-8, 1-10, 1-15, or 1-20 of a particular Table. Alternatively, the method comprises determining the extent of expression of any of a particular subset of eight, nine, ten, eleven, twelve, or thirteen biomarkers selected from biomarker nos. 1-15 or 1-20 of a particular Table. Of course, the skilled person will recognize that it is within the contemplation of this invention to contemporaneously determine the extent of expression of other biomarkers whether or not associated with the disease of interest.

The determination of expression levels for a plurality of biomarkers facilitates the observation of a pattern of changes in expression, and such patterns provide for more sensitive and more accurate diagnoses than detection of individual biomarkers. For example, a pattern of changes would include a plurality of particular biomarkers that are simultaneously expressed at abnormal levels. A pattern of changes may also comprise abnormal elevation of some particular biomarkers simultaneously with abnormal reduction in other particular biomarkers. The skilled person will observe such patterns in the data presented in the Figures included herein. (see Discussion in Example 4 below). Such determination may be performed in a multiplex or matrix-based format such as a multiplexed immunoassay.

In another embodiment, the method comprises determining the extent of expression of any of the biomarkers from at least two Tables (e.g., Table 2 and Table 3). In another embodiment, the method comprises determining the extent of expression of biomarker nos. 1-20 (or the maximum list if less than 20) of a particular Table and biomarker nos. 1-20 (or the maximum list if less than 20) from a different Table, preferably biomarker nos. 1-10 from one or both Tables, more preferably biomarker nos. 1-8 from one or both Tables, even more preferably biomarker nos. 1-6 from one or both Tables, and most preferably biomarker nos. 1-4 from one or both Tables, or a subset of the biomarkers in any of these groups. In another embodiment, the method comprises determining the extent of expression of any combination of a plurality of biomarkers from a particular Table and a different Table. In another embodiment, the method comprises determining the extent of expression of any combination of a plurality biomarkers from biomarker nos. 1-20 (or the maximum list if less than 20) of a particular Table and any combination of a plurality of biomarkers from biomarker nos. 1-20 (or the maximum list if less than 20) from a different Table, preferably any combination of a plurality of biomarkers from biomarker nos. 1-10 from one or both Tables, more preferably any combination of a plurality of biomarkers from biomarker nos. 1-8 from one or both Tables, even more preferably any combination of a plurality of biomarkers from biomarker nos. 1-6 from one or both Tables, and most preferably any combination of a plurality of biomarkers from biomarker nos. 1-4 from one or both Tables, or a subset of the biomarkers in any of these groups. In another embodiment, the plurality of biomarker(s) from one Table are not present in any of the other Tables. In a preferred mode, the method comprises determining the extent of expression of any of a particular subset of three biomarkers selected from biomarker nos. 1-6, 1-8, 140, 1-15, or 1-20 of a particular Table and any of a particular subset of three biomarkers selected from biomarker nos. 1-6, 1-8, 1-10, 1-15, or 1-20 from a different Table. Alternatively, the method comprises determining the extent of expression of any of a particular subset of four, five, six, or seven biomarkers selected from biomarker nos. 1-8 1-10, 1-15, or 1-20 of a particular Table and any of a particular subset of four, five, six, or seven biomarkers selected from biomarker nos. 1-8, 1-10, 1-15, or 1-20 of a different Table. Alternatively, the method comprises determining the extent of expression of any of a particular subset of eight, nine, ten, eleven, twelve, or thirteen biomarkers selected from biomarker nos. 1-15 or 1-20 of a particular Table and any of a particular subset of eight, nine, ten, eleven, twelve, or thirteen biomarkers selected from biomarker nos. 1-15 or 1-20 of a different Table. Of course, the skilled person will recognize that it is within the contemplation of this invention to contemporaneously determine the extent of expression of other biomarkers whether or not associated with the disease of interest.

It will be understood that the same types of combinations are applicable when the method comprises determining the extent of expression of any of the biomarkers from at least three different Tables (e.g., Table 2, Table 3, and Table 4). For example, in one embodiment, the method comprises determining the extent of expression of any combination of a plurality of biomarkers from biomarker nos. 1-20 (or the maximum list if less than 20) of a first Table, any combination of a plurality of biomarkers from biomarker nos. 1-20 (or the maximum list if less than 20) from a second Table, and any combination of a plurality of biomarkers from biomarker nos. 1-20 (or the maximum list if less than 20) of a third Table, preferably any combination of a plurality of biomarkers from biomarker nos. 1-10 from each Table, more preferably any combination of a plurality of biomarkers from biomarker nos. 1-8 from each Table, even more preferably any combination of a plurality of biomarkers from biomarker nos. 1-6 from each Table, and most preferably any combination of a plurality of biomarkers from biomarker nos. 1-4 from each Table. In a preferred mode, the method comprises determining the extent of expression of any of a particular subset of three biomarkers selected from biomarker nos. 1-6, 1-8, 1-10, 1-15, or 1-20 of a first Table, any of a particular subset of three biomarkers selected from biomarker nos. 1-6, 1-8 1-10, 1-45, or 1-20 of a second Table, and any a particular subset of three biomarkers selected from biomarker nos. 1-6, 1-8, 1-10, 1-15, or 1-20 of a third Table. Alternatively, the method comprises determining the extent of expression of any of a particular subset of four, five, six, or seven biomarkers selected from biomarker nos. 1-8, 1-10, 1-15, or 1-20 of a first Table, any of a particular subset of tour, five, six, or seven biomarkers selected from biomarker nos. 1-8, 1-10, 1-15, or 1-20 of a second Table, and any of a particular subset of four, five, six, or seven biomarkers selected from biomarker nos. 1 8, 1-10, 1-15, or 1-20 of a third Table. Alternatively, the method comprises determining the extent of expression of any of a particular subset of eight, nine, ten, eleven, twelve, or thirteen biomarkers selected from biomarker nos. 1-15 or 1-20 of a first Table, any of a particular subset of eight, nine, ten, eleven, twelve, or thirteen biomarkers selected from biomarker nos. 1-15 or 1-20 of a second Table, and any of a particular subset of eight, nine, ten, eleven, twelve, or thirteen biomarkers selected from biomarker nos. 1-15 or 1-20 of a third Table. Of course, the skilled person will recognize that it is within the contemplation of this invention to contemporaneously determine the extent of expression of other biomarkers whether or not associated with the disease of interest.

The determination of expression levels for a plurality of biomarkers facilitates the observation of a pattern of changes in expression, and such patterns provide for more sensitive and more accurate diagnoses than detection individual biomarkers. This determination may be performed in a multiplex or matrix based format such as a multiplexed immunoassay.

In other embodiments, the extent of expression of no more than 5, 10, 15, 20, 25, 30, 35, or 40 are determined.

Selection of biomarkers for use in a diagnostic or prognostic assay may be facilitated using known relationships between particular biomarkers and their first order interactors. Many, if not all, of the biomarkers identified by the present inventors (see Tables 1-23) participate in various communications pathways of the cell or the organism. Deviation of one component of a communication pathway from normal is expected to be accompanied by related deviations in other members of the communication pathway. The skilled worker can readily link members of a communication pathway using various databases and available bioinformatics software (see, e.g., ARIADNE PATHWAY STUDIO, Ariadne, Inc., <www.ariadne.genomics.com> or ChEMBL Database, European Bioinformatics Institute, European Molecular Biology Laboratory, <www.ebi-.ac.uk>). A diagnostic method based on determining whether the levels of a plurality of biomarkers are abnormal where the plurality of biomarkers includes some biomarkers which are not in the same communication pathway as others in the plurality is likely to maximize the information collected by measuring the biomarker levels.

It will also be understood that the various combination of biomarkers previously discussed are also applicable to methods for designing kits and the kits described herein.

It will be appreciated that the selection criteria discussed above, including the preference for selecting particular subsets of markers, may be employed for any of the methods described herein with respect to those Tables associated with the particular methods.

Methods of Physiological Characterization

The present invention is directed to methods for physiological characterization of individuals in various populations as described below. As used herein, a method of physiological characterization according to the methods of this invention include methods of diagnosing particular diseases, methods of predicting the likelihood that an individual will respond to therapeutic intervention, methods of monitoring an individual's reaction to therapeutic intervention, methods of determining whether an individual is at-risk for an individual disease, methods for determining the degree of risk for a particular disease, methods of categorizing a patient's degree of severity of disease, and methods for differentiating between diseases having some symptoms in common. In general, these methods rely on determining the extent of expression of particular biomarkers as described above.

A. General Population

The invention provides for methods of physiological characterization in a subject. In one embodiment, the invention provides for a method of physiological characterization in a subject comprising determining the extent of expression of at least one biomarker from Table 1A in a physiological sample of the subject where the extent of expression of the at least one biomarker is indicative of lung disease such as reactive airway disease or non-small cell lung cancer, or assists in distinguishing between reactive airway disease and non-small cell lung cancer. In another embodiment, the method comprises determining the extent of expression of at least one biomarker from Table 1B where the extent of expression of the at least one biomarker is indicative of reactive airway disease or non-small cell lung cancer, or assists in distinguishing between reactive airway disease and non-small cell lung cancer. In another embodiment, the method comprises determining the extent of expression of at least one biomarker from Table 1C where the extent of expression of the at least one biomarker is indicative of reactive airway disease or non-small cell lung cancer.

In another embodiment, the method comprises determining the extent of expression of SEQ ID NO: 12. In another embodiment, the method comprises determining the extent of expression of SEQ NO: 12 and any one of SEQ ID NOS: 1-11 and 13-17.

In a preferred embodiment, the invention provides for methods of physiological characterization in a subject comprising determining the extent of expression of a plurality of biomarkers from Table 1A in a physiological sample of the subject, where a pattern of expression of the plurality of markers correlate to a physiologic state or condition, or changes in a disease state (e.g., stages in non-small cell lung cancer) or condition. In another preferred embodiment, a pattern of expression of a plurality of biomarkers from Table 1A is indicative of a lung disease such as non-small cell lung cancer or reactive airway disease, or assists in distinguishing between reactive airway disease or non-small cell lung cancer. Preferably, the plurality of biomarkers are selected based on the low probability of erroneous pattern classification based on the value of Student's t as calculated in the Examples. In another preferred embodiment, patterns of expression of biomarkers from Table 1A correlate to an increased likelihood that a subject has or may have a particular disease or condition. In a more preferred embodiment, methods of determining the extent of expression of a plurality of biomarkers from Table 1A in a subject detect an increase in the likelihood that a subject is developing, has or may have a lung disease such as non-small cell lung cancer or reactive airway disease (e.g., asthma). Patterns of expression may be characterized by any technique known in the art for pattern recognition. The plurality of biomarkers may comprise any of the combinations of biomarkers described above with respect to Table 1A.

The invention also provides for a method of physiological characterization in a subject comprising determining the extent of expression of SEQ ID NO: 12 in a physiological sample of the subject, wherein the extent of expression of SEQ ID NO: 12 is indicative of the lung disease of non-small cell lung cancer or reactive airway disease. In a preferred embodiment, a pattern of expression of a plurality of markers of SEQ ID NO: 12 and any one of SEQ ID NOS: 1-11 and 13-17 are determined and used as described herein.

In another aspect, the invention provides for a method of physiological characterization in a subject comprising, (a) obtaining a physiological sample of the subject; (b) determining the extent of expression in said subject of at least one polypeptide selected from the group consisting of SEQ ID NOS: 1-17, and (c) determining the extent of expression in said subject of at least one biomarker from Table 1A, wherein the extent of expression of both the polypeptide and the biomarker from Table 1A is indicative of a lung disease of non-small cell lung cancer or reactive airway disease. In another embodiment, a pattern of expression of a plurality of markers of SEQ ID NOS: 1-17, and a plurality of biomarkers from Table 1A are determined and used as described herein.

In one embodiment, the subject is at-risk for the lung disease of non-small cell cancer or reactive airway disease (e.g., asthma, chronic obstructive pulmonary disease, etc.). Subjects "at-risk" include those individuals who are a symptomatic but are more likely than the bulk of the population to develop the disease, because of personal or family history, behavior, exposure to disease causing agents (e.g., carcinogens), or some other reason. "At-risk" individuals are traditionally identified by aggregating the risk factors determined for the individual. The present invention provides for enhanced detection of "at-risk" individuals by determining the extent of expression of relevant biomarkers. In one embodiment, levels of particular biomarkers associated with the disease (particularly biomarkers from Table 2 or Table 3)

are determined for an individual, and levels which differ from those expected for the normal population suggest that the individual is "at-risk." In another embodiment, the number of relevant biomarkers (from Table 2 or Table 3 as appropriate to the disease) which deviate statistically from normal is determined, with a greater number of deviant markers indicating greater risk.

The embodiments described above refer to the biomarkers of Table 1A. It will be appreciated, however, that the biomarkers of Table 1B or 1C may be substituted for the biomarkers of Table 1A in any of the described embodiments. It will also be appreciated that the plurality of biomarkers to be determined in these particular methods may be selected from the identified tables using the criteria discussed above in the section entitled "Selection of Biomarkers for Determination."

B. Male Population

The invention provides for a method of physiological characterization in a male subject. In one embodiment, the invention provides for a method of physiological characterization in a male subject comprising obtaining a sample from said male subject, and determining the extent of expression of at least one biomarker from Table 5A or 16A in a physiological sample of the male subject where the extent of expression of the at least one biomarker is indicative of lung disease such as reactive airway disease or non-small cell lung cancer, or assists in distinguishing between reactive airway disease and non-small cell lung cancer. In another embodiment, the method comprises determining the extent of expression of at least one biomarker from Table 5B or 16B where the extent of expression of the at least one biomarker is indicative of reactive airway disease or non-small cell lung cancer, or assists in distinguishing between reactive airway disease and non-small cell lung cancer. In another embodiment, the method comprises determining the extent of expression of at least one biomarker from Table 5C or 16C where the extent of expression of the at least one biomarker is indicative of reactive airway disease or non-small cell lung cancer.

In a preferred embodiment, the invention provides for methods of physiological characterization in a male subject comprising determining the extent of expression a plurality of biomarkers from Table 5A or 16A in a physiological sample of the male subject, where a pattern of expression of the plurality of markers correlate to a physiologic state or condition, or changes in a disease state (e.g., stages in non-small cell lung cancer) or condition. In another preferred embodiment, a pattern of expression of a plurality of biomarkers from Table 5A or 16A is indicative of a lung disease such as non-small cell lung cancer or reactive airway disease, or assists distinguishing between reactive airway disease or non-small cell lung cancer. Preferably, the plurality of biomarkers are selected based on the low probability of erroneous pattern classification based on the value of Student's t as calculated in the Examples. In another preferred embodiment, patterns of expression of biomarkers from Table 5A or 16A correlate to an increased likelihood that a male subject has or may have a particular disease or condition. In a more preferred embodiment, methods of determining the extent of expression of a plurality of biomarkers from Table 5A or 16A in a male subject detect an increase in the likelihood that a male subject is developing, has or may have a lung disease such as non-small cell lung cancer or reactive airway disease (e.g., asthma). Patterns of expression may be characterized by any technique known in the art for pattern recognition. The plurality biomarkers may comprise any of the combinations of biomarkers described above with respect to Table 5A or 16A.

In another aspect, the invention provides for a method of physiological characterization in a male subject comprising, (a) obtaining a physiological sample of the male subject; (b) determining the extent of expression in said subject of at least one polypeptide selected from the group consisting of SEQ ID NOS: 1-17, and (c) determining the extent of expression in said subject of at least one biomarker from Table 5A or 16A, wherein the extent of expression of both the polypeptide and the biomarker from Table 5A or 16A is indicative of a lung disease of non-small cell lung cancer or reactive airway disease. In another embodiment, a pattern of expression of a plurality of markers of SEQ ID NOS: 1-17, and a plurality of biomarkers from Table 5A or 16A are determined and used as described herein.

In one embodiment, the male subject is at-risk for the lung disease of non-small cell cancer or reactive airway disease (e.g., asthma, chronic obstructive pulmonary disease, etc.). "At-risk" subjects and individuals are discussed above. In one embodiment, levels of particular biomarkers associated with the disease (particularly biomarkers from Tables 6, 7, 17 or 18) are determined for an male individual, and levels which differ from those expected for the normal population suggest that the male individual is "at-risk."0 In another embodiment, the number of relevant biomarkers (from Tables 6, 7, 17 or 18 as appropriate to the disease) which deviate statistically from normal is determined, with a greater number of deviant markers indicating greater risk.

The embodiments described above refer to the biomarkers of Table 5A or 16A. It will be appreciated, however, that the biomarkers of Table 5B or 5C may be substituted for the biomarkers of Table 5A, and that the biomarkers of Table 16B or 16C may be substituted for the biomarkers of Table 16A in any of the described embodiments. It will also be appreciated that the plurality of biomarkers to be determined in these particular methods may be selected from the identified tables using the criteria discussed above in the section entitled "Selection of Biomarkers for Determination."

C. Female Population

The invention provides for a method of physiological characterization in a female subject. In one embodiment, the invention provides for a method of physiological characterization in a female subject comprising obtaining a sample from said female subject, and determining the extent of expression of at least one biomarker from Table 9A or 20A in a physiological sample of the female subject where the extent of expression of the at least one biomarker is indicative of lung disease such as reactive airway disease or non-small cell lung cancer, or assists in distinguishing between reactive airway disease and non-small cell lung cancer. In another embodiment, the method comprises determining the extent of expression of at least one biomarker from Table 9B or 20B where the extent of expression of the at least one biomarker is indicative of reactive airway disease or non-small cell lung cancer, or assists in distinguishing between reactive airway disease and non-small cell lung cancer. In another embodiment, the method comprises determining the extent of expression of at least one biomarker from Table 9C or 20C where the extent of expression of the at least one biomarker is indicative of reactive airway disease or non-small cell lung cancer.

In a preferred embodiment, the invention provides for methods of physiological characterization in a female subject comprising determining the extent of expression of a plurality of biomarkers from Table 9A or 20A in a physiological sample of the female subject, where a pattern of expression of the plurality of markers correlate to a physiologic state or condition, or changes in a disease state (e.g., stages in non-small cell lung cancer) or condition. In another preferred embodiment, a pattern of expression of a plurality of biomarkers from Table 9A or 20A is indicative of a lung disease such as non-small cell lung cancer or reactive airway disease, or assists in distinguishing between reactive airway disease or non-small cell lung cancer. Preferably, the plurality of biomarkers are selected based on the low probability of erroneous pattern classification based on the value Student's t as calculated in the Examples. In another preferred embodiment, patterns of expression of biomarkers from Table 9A or 20A correlate to an increased likelihood that a female subject has or may have a particular disease or condition. In a more preferred embodiment, methods of determining the extent of expression of a plurality of biomarkers from Table 9A or 20A in a female subject detect an increase in the likelihood that a female subject is developing, has or may have a lung disease such as non-small cell lung cancer or reactive airway disease (e.g., asthma). Patterns of expression may be characterized by any technique known in the art for pattern recognition. The plurality of biomarkers may comprise any of the combinations of biomarkers described above with respect to Table 9A or 20A.

In another aspect, the invention provides for a method of physiological characterization in a female subject comprising, (a) obtaining a physiological sample of the female subject; (b) determining the extent of expression in said subject of at least one polypeptide selected from the group consisting of SEQ ID NOS: 1-17, and (c) determining the extent of expression in said subject of at least one biomarker from Table 9A or 20A, wherein the extent of expression of both the polypeptide and the biomarker from Table 9A or 20A is indicative of a lung disease of non-small cell lung cancer or reactive airway disease. In another embodiment, a pattern of expression of a plurality of markers of SEQ ID NOS: 1-17, and a plurality of biomarkers from Table 9A or 20A are determined and used as described herein.

In one embodiment, the female subject is at-risk for the lung disease of non-small cell cancer or reactive airway disease (e.g., asthma, chronic obstructive pulmonary disease, etc.). "At-risk" subjects and individuals are discussed above. In one embodiment, levels of particular biomarkers associated with the disease (particularly biomarkers from Tables 10, 11, 21, or 22) are determined for an female individual, and levels which differ from those expected for the normal population suggest that the male individual is "at-risk." In another embodiment, the number of relevant biomarkers (from Tables 10, 11, 21, or 22 as appropriate to the disease) which deviate statistically from normal is determined, with a greater number of deviant markers indicating greater risk.

The embodiments described above refer to the biomarkers of Table 9A or 20A. It will be appreciated, however, that the biomarkers of Table 9B or 9C may be substituted for the biomarkers of Table 9A, and that the biomarkers of Table 20B or 20C may be substituted for the biomarkers of Table 9A in any of the described embodiments. It will also be appreciated that the plurality of biomarkers to be determined in these particular methods may be selected from the identified tables using the criteria discussed above in the section entitled "Selection of Biomarkers for Determination."

Lung Disease

The invention provides for various diagnostic and prognostic methods for lung disease. In particular, the invention provides methods of diagnosing reactive airway disease and in particular diseases associated with over reactive $TH_2$ and $TH_{17}$ cells. Reactive airway diseases include asthma, chronic obstructive pulmonary disease, allergic rhinitis, cystic fibrosis, bronchitis, or other diseases manifesting hyperreactivity to various physiological and/or environmental stimuli. In particular, the invention provides for methods of diagnosing asthma and chronic obstructive pulmonary disease, more particularly diagnosing asthma.

The invention also provides methods of diagnosing non-small cell lung cancer. These methods include determining the extent of expression of a least one biomarker described herein, wherein the biomarker(s) is indicative of the presence or development of non-small lung cancer. For example, the extent of expression of biomarkers described herein may be used to determine the extent of progression of non-small lung cancer, the presence of pre-cancerous lesions, or staging of non-small lung cancer.

In particular embodiments, the subject is selected from those individuals who exhibit one or more symptoms of non-small cell lung cancer or reactive airway disease. Symptoms may include cough, shortness of breath, wheezing, chest pain, and hemoptysis; shoulder pain that travels down the outside of the arm or paralysis of the vocal cords leading to hoarseness; invasion of the esophagus may lead to difficulty swallowing. If a large airway is obstructed, collapse of a portion of the lung may occur and cause infections leading to abscesses or pneumonia. Metastases to the bones may produce excruciating pain. Metastases to the brain may cause neurologic symptoms including blurred vision headaches, seizures, or symptoms commonly associated with stroke such as weakness or loss of sensation in parts of the body. Lung cancers often produce symptoms that result from production of hormone-like substances by the tumor cells. A common paraneoplastic syndrome seen in NSCLC is the production parathyroid hormone like substances which cause calcium in the bloodstream to be elevated. Asthma typically produces symptoms such as coughing, especially at night, wheezing, shortness of breath and feelings of chest tightness, pain or pressure. Thus, it is apparent that many of the symptoms of asthma are common to NSCLC.

Methods of Diagnosing Reactive Airway Disease

The present invention is directed to methods of diagnosing reactive airway disease in individuals in various populations as described below. In general, these methods rely on determining the extent of expression of particular biomarkers as described herein.

A. General Population

The invention provides for a method of diagnosing reactive airway disease in a subject comprising, (a) obtaining a physiological sample of the subject; and (b) determining the extent of expression in said subject of at least one biomarker from Table 2, wherein the extent of expression of said at least one biomarker is indicative of reactive airway disease.

In a preferred embodiment, the invention provides for methods of diagnosing reactive airway disease in a subject comprising determining the extent of expression of a plurality of biomarkers from Table 2 in a physiological sample of the subject, wherein a pattern of expression of the plurality of markers are indicative of reactive airway disease or correlate to changes in a reactive airway disease state. In another preferred embodiment, patterns of expression correlate to an increased likelihood that a subject has or may have reactive airway disease. Patterns of expression may be characterized by any technique known in the art for pattern recognition. The plurality of biomarkers may comprise any of the combinations of biomarkers described above with respect to Table 2. Indeed, it will be appreciated that the plurality of biomarkers to be determined in these particular methods may be selected from the identified tables using the criteria discussed above in the section entitled "Selection of Biomarkers for Determination."

In one embodiment, the subject is at-risk for reactive airway disease. In one embodiment, levels particular biomarkers associated with reactive airway disease are determined for an individual, and levels which differ from those expected for the normal population suggest that the individual is "at-risk." In another embodiment, the number of relevant biomarkers from Table 2 which deviate statistically from normal is determined, with a greater number of deviant markers indicating greater risk of reactive airway disease. In another embodiment, the subject is selected from those individuals who exhibit one or more symptoms reactive airway disease.

In any of the above embodiments, the preferred biomarkers for use in this method comprise at least one biomarker from Table 13B. More preferably, all of the biomarkers in this embodiment are found in Table 13B.

B. Male Population

The invention provides for a method of diagnosing reactive airway disease in a male subject comprising, (a) obtaining a physiological sample of the male subject; and (b) determining the extent of expression in said subject of at least one biomarker from Table 6 or 17, wherein the extent of expression of said at least one biomarker is indicative of reactive airway disease.

In a preferred embodiment, the invention provides for methods of diagnosing reactive airway disease in a male subject comprising determining the extent of expression of a plurality of biomarkers from Table 6 or 17 in a physiological sample of the male subject, wherein a pattern of expression of the plurality of markers are indicative of reactive airway disease or correlate to changes in a reactive airway disease state. In another preferred embodiment, patterns of expression correlate to an increased likelihood that a male subject has or may have reactive airway disease. Patterns of expression may be characterized by any technique known in the art for pattern recognition. The plurality of biomarkers may comprise any of the combinations of biomarkers described above with respect to Table 6 or 17. Indeed, it will be appreciated that the plurality of biomarkers to be determined in these particular methods may be selected from the identified tables using the criteria discussed above in the section entitled "Selection of Biomarkers for Determination."

In one embodiment, the male subject is at risk for reactive airway disease. In one embodiment, levels of particular biomarkers associated with reactive airway disease are determined for a male individual, and levels which differ from those expected for the normal male population suggest that the individual is "at-risk." In another embodiment, the number of relevant biomarkers from Table 6 which deviate statistically from normal is determined, with a greater number of deviant markers indicating greater risk of reactive airway disease. In another embodiment, the male subject is selected from those individuals who exhibit one or more symptoms of reactive airway disease.

In another embodiment, the biomarkers for use in this method comprise at least one biomarker from Table 13A.

C. Female Population

The invention provides for a method of diagnosing reactive airway disease in a female subject comprising, (a) obtaining a physiological sample of the female subject; and (b) determining the extent of expression in said subject of at least one biomarker from Table 10 or 21, wherein the extent of expression of said at least one biomarker is indicative of reactive airway disease.

In a preferred embodiment, the invention provides for methods of diagnosing reactive airway disease in a female subject comprising determining the extent of expression of a plurality of biomarkers from Table 10 or 21 in a physiological sample of the female subject, wherein a pattern of expression of the plurality of markers are indicative of reactive airway disease or correlate to changes in a reactive airway disease state. In another preferred embodiment, patterns of expression correlate to an increased likelihood that a female subject has or may have reactive airway disease. Patterns of expression may be characterized by any technique known in the art for pattern recognition. The plurality of biomarkers may comprise any of the combinations of biomarkers described above with respect to Table 10 or 21. Indeed, it will be appreciated that the plurality of biomarkers to be determined in these particular methods may be selected from the identified tables using the criteria discussed above in the section entitled "Selection of Biomarkers for Determination."

In one embodiment, the female subject is at-risk for reactive airway disease. In one embodiment, levels of popular biomarkers associated with reactive airway disease are determined for a female individual, and levels which differ from those expected for the normal female population suggest that the individual is "at-risk." In another embodiment, the number of relevant biomarkers from Table 10 or 21 which deviate statistically from normal is determined, with a greater number of deviant markers indicating greater risk of reactive airway disease. In another embodiment, the female subject is selected from those individuals who exhibit one or more symptoms of reactive airway disease.

In another embodiment, the biomarkers for use in this method compose at least one biomarker from Table 13A.

Methods of Diagnosing Non-Small Cell Lung Cancer

The present invention is directed to methods of diagnosing non-small cell lung cancer in individuals in various populations as described below. In general, these methods rely on determining the extent of expression of particular biomarkers as described herein.

A. General Population

The invention provides for a method of diagnosing non-small cell lung cancer in a subject comprising, (a) obtaining a physiological sample of the subject; and (b) determining the extent of expression in said subject of at least one biomarker from Table 3, wherein the extent of expression of said at least one biomarker is indicative of the presence or development of non-small cell lung cancer.

In a preferred embodiment, the invention provides for methods of diagnosing non-small cell lung cancer in a subject comprising determining the extent of expression of a plurality of biomarkers from Table 3 in a physiological sample of the subject, wherein a pattern of expression of the plurality of markers are indicative of non-small cell lung cancer or correlate to a changes in a non-small cell lung cancer disease state (i.e., clinical or diagnostic stages). In another preferred embodiment, patterns of expression correlate to an increased likelihood that a subject has or may have non-small cell lung cancer. Patterns of expression may be characterized by any technique known in the art for pattern recognition. The plurality of biomarkers may comprise any of the combinations of biomarkers described above with respect to Table 3. Indeed, it will be appreciated that the plurality of biomarkers to be determined in these particular methods may be selected from the identified tables using the criteria discussed above in the section entitled "Selection of Biomarkers for Determination."

In one embodiment, the subject is at-risk for non-small cell lung cancer. In one embodiment, levels of particular biomarkers associated with non-small cell cancer are determined for an individual, and levels which differ from those expected for the normal population suggest that the individual is "at-risk." In another embodiment, the number of relevant biomarkers from Table 3 which deviate statistically from normal is determined, with a greater number of deviant markers indicating greater risk of non-small cell cancer. In another embodiment, the subject is selected from those individuals who exhibit one or more symptoms of non-small cell lung cancer.

In any of the above embodiments, the preferred biomarkers for use in this method comprise at least one biomarker from Table 14B. More preferably, all of the biomarkers in this embodiment are found in Table 14B.

B. Male Population

The invention also provides for a method of diagnosing non-small cell lung cancer in a male subject comprising, (a) obtaining a physiological sample of the male subject; and (b) determining the extent of expression in said subject of at least one biomarker from Table 7 or 18, wherein the extent of expression of said at least one biomarker is indicative of the presence or development of non-small cell lung cancer.

In a preferred embodiment, the invention provides for methods of diagnosing non-small cell lung cancer in a male subject comprising determining the extent of expression of a plurality of biomarkers from Table 7 or 18 in a physiological sample of the male subject, wherein a pattern of expression of the plurality of markers are indicative of non-small cell lung cancer or correlate to a changes in a non-small cell lung cancer disease state (e.g., stages). In another preferred embodiment, patterns of expression correlate to an increased likelihood that a subject has or may have non-small cell lung cancer. Patterns of expression may be characterized by any technique known in the art or pattern recognition. The plurality of biomarkers may comprise any of the combinations of biomarkers described above with respect to Table 7 or 18. Indeed, it will be appreciated that the plurality biomarkers to be determined in these particular methods may be selected from the identified tables using the criteria discussed above in the section entitled "Selection of Biomarkers for Determination."

In one embodiment, the male subject is at-risk for non-small cell lung cancer. In one embodiment, levels of particular biomarkers associated with non-small cell cancer are determined for a male individual, and levels which differ from those expected for the normal male population suggest that the individual is "at-risk." In another embodiment, the number of relevant biomarkers from Table 7 which deviate statistically from normal is determined, with a greater number of deviant markers indicating greater risk of non-small cell cancer. In another embodiment, the male subject is selected from those individuals who exhibit one or more symptoms of non-small cell lung cancer.

In another embodiment, the biomarkers for use in this method comprise at least one biomarker from Table 14A.

C. Female Population

The invention also provides for a method of diagnosing non-small cell lung cancer in a female subject comprising, (a) obtaining a physiological sample of the female subject; and (b) determining the extent of expression in said subject of at least one biomarker from Table 11 or 22, wherein the extent of expression of said at least one biomarker is indicative of the presence or development of non-small cell lung cancer.

In a preferred embodiment, the invention provides for methods of diagnosing non-small cell lung cancer in a female subject comprising determining the extent of expression of a plurality of biomarkers from Table 11 or 22 in a physiological sample of the female subject, wherein a pattern of expression of the plurality of markers are indicative of non-small cell lung cancer or correlate to a changes in a non-small cell lung cancer disease state (e.g., stages). In another preferred embodiment, patterns of expression correlate to an increased likelihood that a female subject has or may have non-small cell lung cancer. Patterns of expression may be characterized by any technique known in the art for pattern recognition. The plurality of biomarkers may comprise any of the combinations of biomarkers described above with respect to Table 11 or 22. Indeed, it will be appreciated that the plurality of biomarkers to be determined in these particular methods may be selected from the identified tables using the criteria discussed above in the section entitled "Selection of Biomarkers for Determination."

In one embodiment, the female subject is at-risk for non-small cell lung cancer. In one embodiment, levels of particular biomarkers associated with non-small cell cancer are determined for a female individual, and levels which differ from those expected for the normal female population suggest that the individual is "at-risk." In another embodiment, the number of relevant biomarkers from Table 11 or 22 which deviate statistically from normal is determined, with a greater number of deviant markers indicating greater risk of non-small cell cancer. In another embodiment, the female subject is selected from those individuals who exhibit one or more symptoms of non-small cell lung cancer.

In another embodiment, the biomarkers for use in this method comprise at least one biomarker from Table 14A.

Methods of Discriminating Between Non-Cell Lung Cancer and Reactive Airway Disease The present invention is directed to methods of diagnosing lung disease in individuals in various populations as described below. In general, these methods rely on determining the extent of expression of particular biomarkers that discriminate between the indication of reactive airway disease and non-small cell lung cancer.

A. General Population

The invention also provides for a method of diagnosing a lung disease in a subject comprising determining the extent of expression in said subject of at least one biomarker from Table 4, wherein the extent of expression of said at least one biomarker from Table 4 assists in discriminating between the indication of reactive airway disease and non-small cell lung cancer. In one embodiment, the subject has been diagnosed as having reactive airway disease and/or non-small cell lung cancer. For example, the diagnosis may have been determined by the extent of expression of at least one biomarker in a physiological sample of the subject, where the extent of expression of the at least one biomarker is indicative of reactive airway disease and/or non-small cell lung cancer.

The invention also provides for a method of diagnosing a lung disease in a subject comprising, (a) obtaining a physiological sample of the subject; and (b) determining the extent of expression in said subject of at least one biomarker from Table 4, at least one biomarker from Table 2, and at least one biomarker from Table 3, wherein (i) said at least one biomarker from each of Table 2, Table 3, and Table 4 is not identical, (ii) the extent of expression of said at least one biomarker from Table 2 and Table 3 is indicative of the lung disease of reactive airway disease and non-small cell lung cancer, respectively; and (iii) the extent of expression of said at least one biomarker from Table 4 assists in discriminating between the indication of non-small cell lung cancer and reactive airway disease. Preferably, the method includes at least one marker from each Table which is not present in either of the other Tables.

In a preferred embodiment, the method comprises determining the extent of expression of a plurality of biomarkers from Table 4, and preferably also a plurality of biomarkers from Table 2, and a plurality of biomarkers from Table 3. In another preferred embodiment, patterns of expression correlate to an increased likelihood that a subject has non-small lung cancer or reactive airway disease. Patterns of expression may be characterized by any technique known in the art for pattern recognition. The plurality of biomarkers may comprise any of the combinations of biomarkers described above with respect to Table 2, Table 3, and Table 4. Indeed, it will be appreciated that the plurality of biomarkers to be determined in these particular methods may be selected from the identified tables using the criteria discussed above in the section entitled "Selection of Biomarkers for Determination."

In one embodiment, the subject is at-risk for non-small cell lung cancer and/or reactive airway disease. In another embodiment, the subject is selected from those individuals who exhibit one or more symptoms of non-small lung cancer and/or reactive airway disease.

The invention also provides a diagnostic method to assist in differentiating the likelihood that a subject is at-risk of developing or suffering from non-small cell lung cancer or reactive airway disease comprising, (a) obtaining a physiological sample of the subject who is at-risk for non-small cell lung cancer or reactive airway disease; and (b) determining the extent of expression in said subject of at least one biomarker from Table 4, wherein the extent of expression of said at least one biomarker from Table 4 assists in differentiating the likelihood that said subject is at risk of non-small cell lung cancer or reactive airway disease.

In a preferred embodiment, the method comprises determining the extent of expression of a plurality of biomarkers from Table 4. In another preferred embodiment, patterns of expression correlate to an increased likelihood that a subject has non-small lung cancer or reactive airway disease. Patterns of expression may be characterized by any technique known in the art for pattern recognition. The plurality of biomarkers may comprise any of the combinations of biomarkers described above with respect to Table 4. Indeed, it will be appreciated that the plurality of biomarkers to be determined in these particular methods may be selected from the identified tables using the criteria discussed above in the section entitled "Selection of Biomarkers for Determination."

In one embodiment, the subject is selected from those individuals who exhibit one or more symptoms of non-small lung cancer or reactive airway disease. Methods of relating to "at-risk" subjects are described above and methods related thereto are contemplated herein.

B. Male Population

The invention also provides for a method of diagnosing a lung disease in a male subject comprising determining the extent of expression in said subject of at least one biomarker from Table 8 or 19, wherein the extent of expression of said at least one biomarker from Table 8 or 19 assists in discriminating between the indication of reactive airway disease and non-small cell lung cancer. In one embodiment, the male subject has been diagnosed as having reactive airway disease and/or non-small cell lung cancer. For example, the diagnosis may have been determined by the extent of expression of at least one biomarker in a physiological sample of the male subject, where the extent of expression of the at least one biomarker is indicative of reactive airway disease and/or non-small cell lung cancer.

The invention also provides for a method of diagnosing a lung disease in a male subject comprising, (a) obtaining a physiological sample of the male subject; and (b) determining the extent of expression in said subject of at least one biomarker from Table 8, at least one biomarker from Table 6, and at least one biomarker from Table 7, wherein (i) said at least one biomarker from each of Table 6, Table 7, and Table 8 is not identical, (ii) the extent of expression of said a least one biomarker from Table 6 and Table 7 is indicative of the lung disease of reactive airway disease and non-small cell lung cancer, respectively; and (iii) the extent of expression of said at least one biomarker from Table 8 assists in discriminating between the indication of non-small cell lung cancer and reactive airway disease. Preferably, the method includes at least one marker from each Table which is not present in either of the other Tables.

The invention also provides for a method of diagnosing a lung disease in a male subject comprising, (a) obtaining a physiological sample of the male subject; and (b) determining the extent of expression in said subject of at least one biomarker from Table 19, at least one biomarker from Table 18, and at least one biomarker Table 17, wherein (i) said at least one biomarker from each of Table 17, Table 18, and Table 19 is not identical, (ii) the extent of expressions aid at least one biomarker from Table 17 and Table 18 is indicative of the lung disease of reactive airway disease and non-small cell lung cancer, respectively; and (iii) the extent of expression of said at least one biomarker from Table 19 assists in discriminating between the indication of non-small cell lung cancer and reactive airway disease. Preferably, the method includes at least one marker from each Table which is not present in either of the other Tables.

In a preferred embodiment, the method comprises determining the extent of expression of a plurality of biomarkers from Table 8, and preferably also a plurality of biomarkers from Table 6, and a plurality of biomarkers from Table 7. In another preferred embodiment, patterns of expression correlate to an increased likelihood that a male subject has non-small lung cancer or reactive airway disease. Patterns of expression may be characterized by any technique known in the art for pattern recognition. The plurality of biomarkers may comprise any of the combinations of biomarkers described above with respect to Table 6, Table 7, and Table 8. Indeed, it will be appreciated that the plurality of biomarkers to be determined in these particular methods may be selected from the identified tables using the criteria discussed above in the section entitled "Selection of Biomarkers for Determination."

In a preferred embodiment, the method comprises determining the extent of expression of a plurality of biomarkers from Table 19, and preferably also a plurality of biomarkers from Table 17, and a plurality of biomarkers from Table 18. In another preferred embodiment, patterns of expression correlate to an increased likelihood that a male subject has non-small lung cancer or reactive airway disease. Patterns of expression may be characterized by any technique known in the art for pattern recognition. The plurality biomarkers may comprise any of the combinations of biomarkers described above with respect to Table 17, Table 18, and Table 19. Indeed, it will be appreciated that the plurality of biomarkers to be determined in these particular methods may be selected from the identified tables using the criteria discussed above in the section entitled "Selection of Biomarkers for Determination."

In one embodiment, the male subject is at-risk for non-small cell lung cancer and/or reactive airway disease. In another embodiment, the male subject is selected from those individuals who exhibit one or more symptoms of non-small lung cancer and/or reactive airway disease.

The invention also provides a diagnostic method to assist in differentiating the likelihood that a male subject is at-risk of developing or suffering from non-small cell lung cancer or reactive airway disease comprising, (a) obtaining a physiological sample of the male subject who is at-risk for non-small cell lung cancer or reactive airway disease; and (b) determining the extent of expression in said subject of at least one biomarker from Table 8 or 19, wherein the extent of expression of said a least one biomarker from Table 8 or 19 assists in differentiating the likelihood that said subject is at risk of non-small cell lung cancer or reactive airway disease.

In a preferred embodiment, the method comprises determining the extent of expression of a plurality of biomarkers from Table 8. In another preferred embodiment, patterns of expression correlate to an increased likelihood that a male subject has non-small lung cancer or reactive airway disease. Patterns of expression may be characterized by any technique known in the art for pattern recognition. The plurality of biomarkers may comprise any of the combinations of biomarkers described above with respect to Table 8 or 19. Indeed, it will be appreciated that the plurality of biomarkers to be determined in these particular methods may be selected from the identified tables using the criteria discussed above in the section entitled "Selection of Biomarkers for Determination."

In one embodiment, the male subject is selected from those individuals who exhibit one or more symptoms of non-small lung cancer or reactive airway disease. Methods of relating to "at-risk" subjects are described above and methods related thereto are contemplated herein.

B. Female Population

The invention also provides for a method of diagnosing a lung disease in a female subject comprising determining the extent of expression in said subject of at least one biomarker from Table 12 or 23, wherein the extent of expression of said at least one biomarker from Table 12 or 23 assists in discriminating between the indication of reactive airway disease and non-small cell lung cancer. In one embodiment, the female subject has been diagnosed as having reactive airway disease and/or non-small cell lung cancer. For example, the diagnosis may have been determined by the extent of expression of at least one biomarker in a physiological sample of the female subject, where the extent of expression of the at least one biomarker is indicative of reactive airway disease and/or non-small cell lung cancer.

The invention also provides for a method of diagnosing a lung disease in a female subject comprising, (a) obtaining a physiological sample of the female subject; and (b) determining the extent of expression in said subject of at least one biomarker from Table 12, at least one biomarker from Table 10, and least one biomarker from Table 11, wherein (i) said at least one biomarker from each of Table 10, Table 11, and Table 12 is not identical, (ii) the extent of expression of said at least one biomarker from Table 10 and Table 11 is indicative of the lung disease of reactive airway disease and non-small cell lung cancer, respectively; and (iii) the extent of expression of said at least one biomarker from Table 12 assists in discriminating between the indication of non-small cell lung cancer and reactive airway disease. Preferably, the method includes at least one marker from each Table which is not present in either of the other Tables.

The invention also provides for a method of diagnosing a lung disease in a female subject comprising, (a) obtaining a physiological sample of the female subject; and (b) determining the extent of expression in said subject of at least one biomarker from Table 23, at least one biomarker from Table 21, and at least one biomarker from Table 22, wherein (i) said at least one biomarker from each of Table 21, Table 22, and Table 23 is not identical, (ii) the extent of expression of said at least one biomarker from Table 21 and Table 22 is indicative of the lung disease of reactive airway disease and non-small cell lung cancer, respectively; and (iii) the extent of expression of said at least one biomarker from Table 23 assists in discriminating between the indication of non-small cell lung cancer and reactive airway disease. Preferably, the method includes at least one marker from each Table which is not present in either of the other Tables.

In a preferred embodiment, the method comprises determining the extent of expression of a plurality of biomarkers from Table 12, and preferably also a plurality of biomarkers from Table 10, and a plurality of biomarkers from Table 11. In another preferred embodiment, patterns of expression correlate to an increased likelihood that a male subject has non-small cancer or reactive airway disease. Patterns of expression may be characterized by any technique known in the art for pattern recognition. The plurality of biomarkers may comprise any of the combinations of biomarkers described above with respect to Table 10, Table 11, and Table 12. Indeed, it will be appreciated that the plurality of biomarkers to be determined in these particular methods may be selected from the identified tables using the criteria discussed above in the section entitled "Selection of Biomarkers for Determination."

In a preferred embodiment, the method comprises determining the extent of expression of a plurality of biomarkers from Table 23, and preferably also a plurality of biomarkers from Table 21, and a plurality of biomarkers from Table 22. In another preferred embodiment, patterns of expression correlate to an increased likelihood that a male subject has non-small lung cancer or reactive airway disease. Patterns of expression may be characterized by any technique known in the art for pattern recognition. The plurality of biomarkers may comprise any of the combinations of biomarkers described above with respect to Table 21, Table 22, and Table 23. Indeed, it will be appreciated that the plurality of biomarkers to be determined in these particular methods may be selected from the identified tables using the criteria discussed above in the section entitled "Selection of Biomarkers for Determination."

In one embodiment, the female subject is at-risk for non-small cell lung cancer and/or reactive airway disease. In another embodiment, the female subject is selected from those individuals who exhibit one or more symptoms of non-small lung cancer and/or reactive airway disease.

The invention also provides a diagnostic method to assist in differentiating the likelihood that a female subject is at-risk of developing or suffering from non-small cell lung cancer or reactive airway disease comprising, (a) obtaining a physiological sample of the female subject who is at-risk for non-small cell lung cancer or reactive airway disease; and (b) determining the extent of expression in said subject of at least one biomarker from Table 12 or 23, wherein the extent of expression of said at least one biomarker from Table 12 or 23 assists in differentiating the likelihood that said subject is at risk of non-small cell lung cancer or reactive airway disease.

In a preferred embodiment, the method comprises determining the extent of expression of a plurality of biomarkers from Table 12 or 23. In another preferred embodiment, patterns of expression correlate to an increased likelihood that a female subject has non-small lung cancer or reactive airway disease. Patterns of expression may be characterized by any technique known in the art for pattern recognition. The plurality of biomarkers may comprise any of the combinations of biomarkers described above with respect to Table 12 or 23. Indeed, it will be appreciated that the plurality biomarkers to be determined in these particular methods may be selected from the identified tables using the criteria discussed above in the section entitled "Selection of Biomarkers for Determination."

In one embodiment, the female subject is selected from those individuals who exhibit one or more symptoms of non-small lung cancer or reactive airway disease. Methods of relating to "at-risk" subjects are described above and methods related thereto are contemplated herein.

In any of the methods described herein which use biomarkers selected from more than one Table for the purpose of discriminating between, e.g., different disease states or different populations, analysis of the results for the biomarkers from individuals may be performed simultaneously or sequentially.

Methods of Monitoring Therapy

The present invention is directed to methods of monitoring therapy in individuals in various populations as described below. In general, these methods rely on determining the extend expression of particular biomarkers.

A. General Population

The invention also provides a method of monitoring a subject comprising (a) determining a first extent of expression in said subject of at least one biomarker from Table 1A in a sample obtained from the subject; (b) determining a second extent of expression in said subject of said at least one biomarker from Table 1A using a second sample obtained from the subject at a different time than said first extent of expression; and (d) comparing said first extent of expression and said second extent of expression. Typically, the subject has experienced therapeutic intervention between the time the first and second samples were obtained. Detecting of changes in the pattern of expression between the first and second determinations may be considered to reflect effects of the therapeutic intervention. This embodiment is also useful to identify particular biomarkers which exhibit changes in their extent of expression in response to particular therapeutic interventions.

In a preferred embodiment, the method comprises determining the extent of expression of a plurality of biomarkers from Table 1A. The plurality of biomarkers may comprise any of the combinations of biomarkers described above with respect to Table 1A. Indeed, it will be appreciated that the plurality of biomarkers to be determined in these particular methods may be selected from the identified tables using the criteria discussed above in the section entitled "Selection of Biomarkers for Determination."

The embodiments described above refer to the biomarkers of Table 1A. It will be appreciated, however, that the biomarkers of Table 1B, Table 1C, Table 2, Table 3, or Table 4 may be substituted for the biomarkers of Table 1A in any of the described embodiments.

B. Male Population

The invention also provides a method of monitoring a male subject comprising (a) determining a first extent of expression in said male subject of at least one biomarker from Table 5A or 16A in a sample obtained from the male subject; (b) determining a second extent of expression in said male subject of said at least one biomarker from Table 1A or 16A using a second sample obtained from the male subject at a different time than said first extent of expression; and (d) comparing said first extent of expression and said second extent of expression. Typically, the male subject has experienced therapeutic intervention between the time the first and second samples were obtained. Detecting of changes in the pattern of expression between the first and second determinations may be considered to reflect effects of the therapeutic intervention. This embodiment is also useful to identify particular biomarkers which exhibit changes in their extent of expression in response to particular therapeutic interventions.

In a preferred embodiment, the method comprises determining the extent of expression of a plurality of biomarkers from Table 5A or 16A. The plurality biomarkers may comprise any of the combinations of biomarkers described above with respect to Table 5A or 16A. Indeed, it will be appreciated that the plurality of biomarkers to be determined in these particular methods may be selected from the identified tables using the criteria discussed above in the section entitled "Selection of Biomarkers for Determination."

The embodiments described above refer to the biomarkers of Table 5A or 16A. It will be appreciated, however, that the biomarkers of Table 5B, Table 5C, Table 6, Table 7, Table 8, or Table 16B, Table 16C, Table 17, Table 18, or Table 19 may be substituted for the biomarkers of Table 5A or 16A in any of the described embodiments.

C. Female Population

The invention also provides a method of monitoring a female subject comprising (a) determining a first extent of expression in said female subject of at least one biomarker from Table 9A or 20A in a sample obtained from the female subject; (b) determining second extent of expression in said female subject of said at least one biomarker from Table 9A or 20A using a second sample obtained from the female subject at a different time than said first extent of expression; and (d) comparing said first extent of expression and said second extent of expression. Typically, the female subject has experienced therapeutic intervention between the time the first and second samples obtained. Detecting of changes in the pattern of expression between the first and second determinations may be considered to reflect effects of the therapeutic intervention. This embodiment is also useful to identify particular biomarkers which exhibit changes in their extent of expression in response to particular therapeutic interventions.

In a preferred embodiment, the method comprises determining the extent of expression of a plurality of biomarkers from Table 9A or 20A. The plurality of biomarkers may comprise any of the combinations of biomarkers described above with respect to Table 9A or 20A. Indeed, it will be appreciated that the plurality of biomarkers to be determined in these particular methods may be selected from the identified tables using the criteria discussed above in the section entitled "Selection of Biomarkers for Determination."

The embodiments described above refer to the biomarkers of Table 9A or 20A. It will be appreciated, however, that the biomarkers of Table 9B, Table 9C, Table 10, Table 11, Table 12, Table 20B, Table 20C, Table 21, Table 22, or Table 23 may be substituted for the biomarkers of Table 9A or 20A in any of the described embodiments.

Methods of Predicting a Subject's Response to Therapeutic Intervention

The present invention is directed to methods of predicting a subject's response to therapeutic intervention in various populations as described below. In general, these methods rely on determining the extent of expression of particular biomarkers.

A. General Population

The invention also provides a method for predicting a subject's response to therapeutic intervention comprising, (a) obtaining a physiological sample of the subject; and (b) determining the extent of expression in said subject of at least one biomarker from Table 1A, wherein the extent of expression of said at least one biomarker from Table 1A assists in predicting a subject's response to said therapeutic intervention. Preferred biomarkers for use in this embodiment are those biomarkers shown to be responsive to the therapeutic intervention of interest by monitoring a population of subjects. This embodiment may also be used for selection of those patients more likely to be responsive to therapy.

In a preferred embodiment, the method comprises determining the extent of expression of a plurality of biomarkers from Table 1A. The plurality of biomarkers may comprise any of the combinations of biomarkers described above with respect to Table 1A. Indeed, it will be appreciated that the plurality of biomarkers to be determined in these particular methods may be selected from the identified tables using the criteria discussed above in the section entitled "Selection of Biomarkers for Determination."

The embodiments described above refer to the biomarkers of Table 1A. It will be appreciated, however, that the biomarkers of Table 1B, Table 1C, Table 2, Table 3, or Table 4 may be substituted for the biomarkers of Table 1A in any of the described embodiments.

B. Male Population

The invention also provides a method for predicting a male subject's response to therapeutic intervention comprising, (a) obtaining a physiological sample of the male subject; and (b) determining the extent of expression in said male subject of at least one biomarker from Table 5A or 16A, wherein the extent of expression of said at least one biomarker from Table 5A or 16A assists in predicting a male subject's response to said therapeutic intervention. Preferred biomarkers for use in this embodiment are those biomarkers shown to be responsive to the therapeutic intervention of interest by monitoring a population of male subjects. This embodiment may also be used for selection of those male patients more likely to be responsive to therapy.

In a preferred embodiment, the method comprises determining the extent of expression of a plurality of biomarkers from Table 5A or 16A. The plurality of biomarkers may comprise any of the combinations of biomarkers described above with respect to Table 5A or 16A. Indeed, it will be appreciated that the plurality of biomarkers to be determined in these particular methods may be selected from the identified tables using the criteria discussed above in the section entitled "Selection of Biomarkers for Determination."

The embodiments described above refer to the biomarkers of Table 5A or 16A. It will be appreciated, however, that the biomarkers of Table 5B, Table 5C, Table 6, Table 7, Table 8, Table 16B, Table 16C, Table 17, Table 18, or Table 19 may be substituted for the biomarkers of Table 5A or 16A in any of the described embodiments.

C. Female Population

The invention also provides a method for predicting a female subject's response to therapeutic intervention comprising, (a) obtaining a physiological sample of the female subject; and (b) determining the extent of expression in said female subject of at least one biomarker from Table 9A or 20A, wherein the extent of expression of said at least one biomarker from Table 9A or 20A assists in predicting a female subject response to said therapeutic intervention. Preferred biomarkers for use in this embodiment are those biomarkers shown to be responsive to the therapeutic intervention of interest by monitoring a population of female subjects. This embodiment may also be used for selection of those female patients more likely to be responsive to therapy.

In a preferred embodiment, the method comprises determining the extent of expression of a plurality of biomarkers from Table 9A or 20A. The plurality of biomarkers may comprise any of the combinations of biomarkers described above with respect to Table 9A or 20A. Indeed, it will be appreciated that the plurality of biomarkers to be determined in these particular methods may be selected from the identified tables using the criteria discussed above in the section entitled "Selection Biomarkers for Determination."

The embodiments described above refer to the biomarkers of Table 9A or 20A. It will be appreciated, however, that the biomarkers of Table 9B, Table 9C, Table 10, Table 11, Table 12, Table 20B, Table 20C, Table 21, Table 22, or Table 23 may be substituted for the biomarkers of Table 9A or 20A in any of the described embodiments.

Methods of Designing Kits

A. General Population

The invention also provides a method for designing a kit for assisting in diagnosing a lung disease in a subject comprising (a) selecting at least one biomarker from Table 1A; (b) selecting a means for determining the extent of expression of said least one biomarker; and (c) designing a kit comprising said means for determining the extent of expression.

The invention also provides a method for designing a kit for diagnosing non-small cell lung cancer or reactive airway disease in a subject comprising (a) selecting at least one biomarker from Table 1B; (b) selecting a means for determining the extent of expression of said at least one biomarker; and (c) designing a kit comprising said means for determining the extent of expression.

The invention also provides a method for designing a kit for diagnosing non-small cell lung cancer or reactive airway disease in a subject comprising (a) selecting at least one biomarker from Table 1C; (b) selecting a means for determining the extent of expression of said at least one biomarker; and (c) designing a kit comprising said means for determining the extent of expression.

The invention also provides a method for designing a kit for diagnosing reactive airway disease in a subject comprising (a) selecting at least one biomarker from Table 2; (b) selecting a means for determining the extent of expression of said at least one biomarker; and (c) designing a kit comprising said means for determine the extent of expression.

The invention also provides a method for designing a kit for diagnosing non-small cell lung cancer in a subject comprising (a) selecting at least one biomarker from Table 3; (b) selecting a means for determining the extent of expression of said at least one biomarker; and (c) designing a kit comprising said means for determining the extent of expression.

The invention also provides a method for designing a kit for assisting in diagnosing a lung disease in a subject comprising (a) selecting at least one biomarker from Table 4; (b) selecting a means for determining the extent of expression of said at least one biomarker; and (c) designing a kit comprising said means for determining the extent of expression.

In the above methods, steps (b) and (c) may alternatively be performed by (b) selecting detection agents for detecting said at least one biomarker, and (c) designing a kit comprising said detection agents for detecting at least one biomarker.

The invention also provides methods for designing kits comprising selecting at least one biomarker from more than one Table. For example, the invention provides a method for designing kit comprising selecting at least one biomarker from Table 2 and at least one biomarker from Table 3. In another example, the invention provides a method for designing kit comprising selecting at least one biomarker from Table 2, at least one biomarker from Table 3, and at least one biomarker from Table 4. It will be understood that these methods also comprise steps (b) and (c) as previously described.

It will be appreciated that the plurality of biomarkers to be determined in these particular methods may be selected from the identified tables using the criteria discussed above in the section entitled "Selection of Biomarkers for Determination."

B. Male Population

The invention also provides a method for designing a kit for assisting in diagnosing a lung disease in a male subject comprising (a) selecting at least one biomarker from Table 5A or 16A; (b) selecting a means for determining the extent of expression of said at least one biomarker; and (c) designing a kit comprising said means for determining the extent of expression.

The invention also provides a method for designing a kit for diagnosing non-small cell lung cancer or reactive airway disease in a male subject comprising (a) selecting at least one biomarker from Table 5B or 16B; (b) selecting a means for determining the extent of expression of said at least one biomarker; and (c) designing a kit comprising said means for determining the extent of expression.

The invention also provides a method for designing a kit for diagnosing non-small cell lung cancer or reactive airway disease in a male subject comprising (a) selecting at least one biomarker from Table 5C or 16C; (b) selecting a means for determining the extent of expression of said at least one biomarker; and (c) designing a comprising means for determining the extent of expression.

The invention also provides a method for designing a kit for diagnosing reactive airway disease in a male subject comprising (a) selecting at least one biomarker from Table 6 or 17; (b) selecting a means for determining the extent of expression of said at least one biomarker; and (c) designing a kit comprising said means for determining the extent of expression.

The invention also provides a method for designing a kit for diagnosing non-small cell lung cancer in a male subject comprising (a) selecting at least one biomarker from Table 7 or 18; (b) selecting a means for determining the extent of expression of said at least one biomarker; and (c) designing a kit comprising said means for determining the extent of expression.

The invention also provides a method for designing a kit for assisting in diagnosing a lung disease in a male subject comprising (a) selecting at least one biomarker from Table 8 or 19; (b) selecting a means for determining the extent of expression of said at least one biomarker; and (c) designing a kit comprising said means for determining the extent of expression.

In the above methods, steps (b) and (c) may alternatively be performed by (b) selecting detection agents for detecting said at least one biomarker, and (c) designing a kit comprising said detection agents for detecting at least one biomarker.

The invention also provides methods for designing kits comprising selecting at least one biomarker from more than one Table. For example, the invention provides a method for designing kit comprising selecting at least one biomarker from Table 6 and at least one biomarker from Table 7. In another example, the invention provides a method for designing kit comprising selecting at least one biomarker from Table 6, at least one biomarker from Table 7, and at least one biomarker from Table 8. In another example, the invention provides a method for designing kit comprising selecting at least one biomarker from Table 17 and at least one biomarker from Table 18. In another example, the invention provides a method for designing kit comprising selecting at least one biomarker from Table 17, at least one biomarker from Table 18, and at least one biomarker from Table 19. It will be understood that these methods also comprise steps (b) and (c) as previously described.

It will be appreciated that the plurality of biomarkers to be determined in these particular methods may be selected from the identified tables using the criteria discussed above in the section entitled "Selection of Biomarkers for Determination."

C. Female Population

The invention also provides a method for designing a kit for assisting in diagnosing a lung disease in a female subject comprising (a) selecting at least one biomarker from Table 9A or 20A; (b) selecting a means for determining the extent of expression of said at least one biomarker; and (c) designing a kit comprising said means for determining the extent of expression.

The invention also provides a method for designing a kit for diagnosing non-small cell lung cancer or reactive airway disease in a female subject comprising (a) selecting at least one biomarker from Table 9B or 20B; (b) selecting a means for determining the extent of expression of said at least one biomarker; and (c) designing a kit comprising said means for determining the extent of expression.

The invention also provides a method for designing a kit for diagnosing non-small cell lung cancer or reactive airway disease in a female subject composing (a) selecting at least one biomarker from Table 9C or 20C; (b) selecting a means for determining the extent of expression of said at least one biomarker; and (c) designing a kit comprising said means for determining the extent of expression.

The invention also provides a method for designing a kit for diagnosing reactive airway disease in a female subject comprising (a) selecting at least one biomarker from Table 10 or 21; (b) selecting a means for determining the extent of expression of said at least one biomarker; and (c) designing a kit comprising said means for determining the extent of expression.

The invention also provides a method for designing a kit for diagnosing non-small cell lung cancer in a female subject comprising (a) selecting at least one biomarker from Table 11 or 22; (b) selecting a means for determining the extent of expression of said at least one biomarker; and (c) designing a kit comprising said means for determining the extent of expression.

The invention also provides a method for designing a kit for assisting in diagnosing a lung disease in a female subject comprising (a) selecting at least one biomarker from Table 12 or 23; (b) selecting a means for determining the extent of expression of said at least one biomarker; and (c) designing a kit comprising said means for determining the extent of expression.

In the above methods, steps (b) and (c) may alternatively be performed by (b) selecting detection agents for detecting said at least one biomarker, and (c) designing a kit comprising said detection agents for detecting at least one biomarker.

The invention also provides methods for designing kits comprising selecting at least one biomarker from more than one Table. For example, the invention provides a method for designing kit comprising selecting at least one biomarker from Table 10 and at least one biomarker from Table 11. In another example, the invention provides a method for designing kit comprising selecting at least one biomarker from Table 10, at least one biomarker from Table 11, and at least one biomarker from Table 12. In another example, the invention provides a method for designing kit comprising selecting at least one biomarker from Table 21 and at least one biomarker from Table 22. In another example, the invention provides a method for designing kit comprising selecting at least one biomarker Table 21, at least one biomarker from Table 22, and at least one biomarker from Table 23. It will be understood that these methods also comprise steps (b) and (c) as previously described.

It will be appreciated that the plurality of biomarkers to be determined in these particular methods may be selected from the identified tables using the criteria discussed above in the section entitled "Selection of Biomarkers for Determination."

Kits

The invention provides kits comprising means for determining the extent of expression of at least one of the biomarkers described herein. The invention also provides kits comprising detection agents for detecting at least one biomarker described herein.

The invention provides a kit comprising means for determining the extent of expression of at least one biomarker from Table 1A. The invention provides a kit comprising detection agents for detecting at least one biomarker from Table 1A.

The invention also provides a kit comprising means for determining the extent of expression of SEQ ID NO: 12. In one embodiment, the kit comprises means for determining the extent of expression of SEQ ID NO: 12 and any combination of SEQ ID NOS: 1-11 and 13-17.

The invention also provides a kit comprising, detection agents for detecting SEQ ID NO: 12. In one embodiment, the kit comprises detection agents for detecting SEQ ID NO: 12 and any combination of SEQ ID NOS: 1-11 and 13-17.

The invention also provides a kit comprising means for determining the extent of expression of at least one polypeptide selected from the group consisting of SEQ ID NOS: 1-17 and means for determining the extent of expression of at least one biomarker from Table 1A.

The invention also provides a kit comprising, detection agents for detecting at least one polypeptide selected from the group consisting of SEQ ID NOS: 1-17, and detection agents for detecting at least one biomarker from Table 1A.

The embodiments described above refer to the biomarkers of Table 1A. It will be appreciated, however, that the biomarkers of Table 1B, Table 1C, Table 2, Table 3, Table 4, Table 5A, Table 5B, Table 5C, Table 6, Table 7, Table 8, Table 9A, Table 9B, Table 9C, Table 10, Table 11, Table 12, Table 16A, Table 16B, Table 16C, Table 17, Table 18, Table 19, Table 20A, Table 20B, Table 20C, Table 21, Table 22, or Table 23 may be substituted for the biomarkers of Table 1A in any of the described kits.

The invention also provides a kit comprising, (a) first means for determining the extent of expression of at least one biomarker from Table 2; and (b) second means for determining the extent of expression of at least one biomarker from Table 3, wherein said at least one biomarker from Table 2 and Table 3 are not identical.

The invention also provides a kit comprising, (a) detection agents for detecting at least one biomarker from Table 2; and (b) detection agents for detecting at least one biomarker from Table 3, wherein said at least one biomarker from Table 2 and Table 3 are not identical.

The invention also provides a kit comprising, (a) first means for determining the extent of expression of at least one biomarker from Table 2; (b) second means for determining the extent of expression of at least one biomarker from Table 3; and (c) third means for determining the extent of expression of at least one biomarker from Table 4, wherein said at least one biomarker from Table 2, Table 3, and Table 4 are not identical.

The invention also provides a kit comprising, (a) detection agents for detecting at least one biomarker from Table 2; (b) detection agents detecting at least one biomarker from Table 3; and (c) detection agents for detecting at least one biomarker from Table 4, wherein said at least one biomarker from Table 2, Table 3, and Table 4 are not identical.

The embodiments described above refer to the biomarkers of Table 2, Table 3, and Table 4. It will be appreciated, however, that the biomarkers of Table 6, Table 7, Table 8, Table 17, Table 18, or Table 19 may be substituted for the biomarkers of Table 2, Table 3, and Table 4, respectively, in any of the described kits. Furthermore, it will be appreciated that the biomarkers of Table 10, Table 11, Table 12, Table 21, Table 22, or Table 23 may be substituted for the biomarkers of Table 2, Table 3, and Table 4, respectively, in any of the described kits. Even further, the skilled person will understand that the invention contemplates kits comprising means for detecting any particular combination of biomarkers described above for any method requiring detection of a particular plurality of biomarkers. It will also be appreciated that the plurality of biomarkers to be determined in these particular kits may be selected from the identified tables using the criteria discussed above in the section entitled "Selection of Biomarkers for Determination."

The following examples are provided to exemplify various modes of the invention disclosed herein, but they are not intended to limit the invention in any way.

EXAMPLE 1

Human blood samples were collected from volunteers. Thirty samples were collected from individuals not known to have either non-small cell lung cancer or asthma. These thirty samples comprise, and are referred to herein as, the "normal population." Twenty-eight blood samples were collected from individuals known to have asthma and diagnosed as such by a physician. These twenty-eight samples comprise, and are referred to herein as, the "asthma population." Thirty blood samples were collected from individuals known to have non-small cell lung cancers and diagnosed as such by a physician. These thirty samples comprise, and are referred to herein as the "lung cancer population."

Research was performed to select biomarkers for which was believed that altered expression levels would be associated with lung cancer or asthma. As used herein, "lung cancer" is meant to encompass those lung cancers which are known to be non-small celled lung cancers. The following fifty-nine biomarkers were selected to be tested: CD40, Hepatocyte Growth Factor ("HGF"), I-TAC ("CXCL11"; "chemokine (C-X-C motif) ligand 11," "interferon-inducible T-cell alpha chemoattractant"), Leptin ("LEP"), Matrix Metalloproteinase ("MMP") 1, MMP 2, MMP3, MMP 7, MMP 8, MMP 9, MMP 12, MMP 13, CD40 Soluble Ligand ("CD40 Ligand"), Epidermal Growth Factor ("EFG"), Eotaxin ("CCL11"), Fractalkine, Granulocyte Colony Stimulating Factor ("G-CSF"), Granulocyte Macrophage Colony Stimulating Factor ("GM-CSF"), Interferon γ ("IFN γ"), Interleukin ("IL") 1α, IL-1β, IL-1ra, IL-2, IL-4, IL-5, IL-6, IL-7, IL-8, IL-10, IL-12(p40), IL-12(p70), IL-13, IL-15, IL-17, IP-10, Monocyte Chemotactic Protein 1 ("MCP-1"), Macrophage Inflammatory Protein ("MIP") 1α, MIP-1β, Transforming Growth Factor α ("TGF α"), Tumor Necrosis Factor α ("TNF α"), Vascular Endothelial Growth Factor ("VEGF"), Insulin ("Ins"), C-peptide, Glucagon Like Protein-1/amyline ("GLP-1/amylin"), Amylin (total), Glucagon, Adiponectin, Plasminogen Activator Inhibitor 1 ("PAI-1"; "Serpin") (active/total), Resistin ("RETN"; "xcp1"), sFas, Soluble Fas Ligand ("sFasL"), Macrophage Migration Inhibitory Factor ("MIF"), sE-Selectin, Soluble Vascular Cell Adhesion Molecule ("sVCAM"), Soluble Intracellular Adhesion Molecule ("sICAM"), Myeloperoxidase ("MPO"), C-Reactive Protein ("CRP"), Serum Amyloid A ("SAA"; "SAA1"), and Serum Amyloid P ("SAP").

Plasma specimens for each of the normal, asthma and lung cancer populations were screened for each of the fifty-nine biomarkers by subjecting the plasma specimens to analysis using Luminex's xMAP technology, a quantitative multiplexed immunoassay using automated bead-based technologies.

Several different assay kits were used with the Luminex xMAP technology to screen the biomarkers, namely Millipore's Human Cytokine/Chemokine (Cat #MPXHCYTO-60K, Human Endocrine (Cat #HENDO-65K), Human Serum Adipokines (Cat #HADKI-61K), Human Sepsis/Apoptosis (Cat #HSEP-63K), Human Cardiovascular Panel 1 (Cat #HCVD1-67AK) and Human Cardiovascular Panel 2 (HCVD2-67BK), R&D Systems, Inc.'s Human Fluorokine MAP Profiling Base Kit B (Cat #LUB00) and Human Fluorokine MAP MMP Profiling Base Kit (Cat #LMP000). The fluorescence intensity levels resulting from the multiplexed immunoassay were recorded for each of the fifty-nine biomarkers for each plasma specimen for each population. The recorded fluorescence intensity is proportional to the concentration of the corresponding biomarker in the sample, and to the extent of its expression in the individual. Averages, standard deviations, and relative standard deviations for fluorescence intensity level associated with each biomarker for each population were calculated. FIGS. 1A through 1C show the average mean, standard deviation and relative standard deviation for each biomarker in the normal (NO), non-small cell lung cancer (LC), and asthma (AST) populations.

Student's t test was then used to characterize inter-pathology differences for each particular biomarker between each population. Mean fluorescence intensity measurements of each biomarker for the samples from normal patients were compared to those of the samples from patients suffering from lung cancer and also to those of samples derived from patients suffering from asthma. FIG. 1D shows the differences between the various population means for each marker. In addition, the mean fluorescence intensity measurements for the lung cancer patients were compared to the mean fluorescence intensity measurements for the asthma patients, and the significance was evaluated using the Student's t statistic.

Further analysis of the statistical differences for each biomarker between the normal, asthma and lung cancer populations was performed. To characterize the difference in mean expression levels for each biomarker between the populations, Student's t values were calculated using the t-test function available in the Microsoft EXCEL software package. The EXCEL t-test function was used to calculate the probability associated with the Student's t value under an assumption of equal variance using a two-tailed distribution.

The significance of the difference in expression levels between the populations was determined on the criteria that any Student's t value with an associated probability smaller than 0.05 was considered to be significant to indicate the presence of the given pathology, whether asthma or lung cancer. Using a criterion of 0.05 or less is generally accepted in the scientific community. Any Student's t value with an associated probability larger than 0.1 was considered to be insignificant to indicate the presence of the given pathology. Furthermore, any Student's t value with an associated probability between 0.051 and 0.1 was determined to be marginal.

Referring now to FIG. 1E, the Student's t values with an associated probability calculated comparing each biomarker for each population is shown. It should be noted that the Student's t values with an associated probability shown in FIG. 1E are calculated on the basis that each of the asthma, normal, and lung cancer populations has a single mean and a normal distribution.

The significance of the differences in biomarker expression levels were used to rank the relative importance of the biomarkers. Those biomarkers that were found to be most significantly different between pathologies were classed as relatively more important. The measurements of mean fluorescence intensity were examined, and data for all biomarkers having intensities that did not depart significantly from the average intensities of specimens in the other populations were excluded from further analysis. Those biomarkers having relatively low relative standard deviation were classed as more significant than those having relatively high standard deviation.

The direction of deviation, i.e. whether the average level of a particular marker increased or decreased in any pathology relative to any of the other pathologies, was not used to judge the relative significance of a particular marker. In this way, a group of biomarkers was assembled that showed high variability between pathologies, relatively low relative standard deviation and good instrumental detect (defined as non-zero uncorrected mean fluorescence intensity). Those calculations were used to test the efficiency of the immunoassay and analyzed to determine the biomarkers which showed significant differences in expression levels between the expression levels of the normal population, as well as to determine reference ranges which are characteristic of and associated with the pathologies of lung cancer and/or asthma.

Still referring to FIG. 1E, the probabilities associated with the Student's t values were calculated to compare the asthma population to the normal population. Significant differences between the asthma population and the normal population were determined from the Student's t probability for the biomarkers sE-Selectin, EGF, Leptin, IL-5, PAI-1 Resistin, MMP-13, CD40 Ligand sVCAM-1, HGF, C-Peptide, sICAM-1, MMP-7, Adiponectin, GM-CSF and MIF. This determination was made on the basis that, when comparing the twenty-eight specimens from the asthma population with the thirty specimens from the normal population using the Student's t function described herein, the probabilities associated with the Student's t value for each of these biomarkers was smaller than 0.05. Difference was determined to be insignificant between the asthma population and the normal population for the biomarkers CRP, MMP-9, IL-4, IL-1α, SAA, IL-7 and IL-6, as the Student's t probability for each of these was significantly greater than 0.05.

As also shown in FIG. 1E, the probabilities associated with the Student's t values were calculated to compare the lung cancer population to the normal population. Significant difference between the lung cancer population and the normal population was determined from the Student's t probability for the biomarkers sE-Selectin, EGF, Leptin, IL-5, PAI-1, Resistin, CRP, MMP-9, IL-4, IL-1α, SAA, IL-7, CD40 Ligand, MMP-7 and MMP-12. Again, this determination was made on the basis that, when comparing the thirty specimens from the lung cancer population with the thirty specimens from the normal population using the Student's t function described herein, the Student's t probability for each of these biomarkers was smaller than 0.05. Difference was determined to be insignificant between the lung cancer population and the normal population for the biomarkers MMP-13, HGF, C-Peptide, sICAM, Adiponectin, GM-CSF, IL-17, TNF α, ITAC and MIF, as the Student's t probability for each of these biomarkers was significantly greater than 0.05.

Three biomarkers had probabilities associated with the Student's t values only slightly greater than 0.05 between the lung cancer population and the normal population. Specifically, when comparing the lung cancer population to the normal population, IL-6 had a Student's t probability of 0.076195528, sVCAM-1 had a Student's t probability of 0.08869949, and IL-15 had a Student's T probability of 0.086324372. These biomarkers are regarded as having insignificant difference between the lung cancer population and the normal population. However, due to the fact that the Student's t probability for these three biomarkers are close to 0.05, it is possible that each population may significantly vary between the normal and lung cancer populations.

Finally, as shown in FIG. 1E, further analysis was done by calculating the probabilities associated with the Student's t values to compare the lung cancer population to the asthma population. Significant difference between the lung cancer population and the asthma population was determined from the Student's t probability for the biomarkers sE-Selectin, EGF, Leptin, IL-5, PAI-1, Resistin, CRP, MMP-9, IL-4, IL-1α, SAA, IL-7, IL-6, MMP-13 sVCAM, HGF, C-Peptide, sICAM, Adiponectin, GM-CSF, IL-17, L-15, TNF α and I-TAC. This determination was made on the basis that, when comparing the thirty specimens from the lung cancer population with the twenty-eight specimens from the asthma population using the Student's t function described herein, the Student's t probability for each of these biomarkers was smaller than 0.05. Difference was determined to be insignificant between the lung cancer population and the asthma population for the biomarkers CD40 Ligand, MMP-7, MMP-12 and MIF, as the Student's t probability for each of these biomarkers was significantly greater than 0.05.

EXAMPLE 2

Human blood samples were collected from volunteers. One hundred forty-two samples were collected from individuals not known to have either non-small cell lung cancer or asthma. These samples comprise, and are referred to herein as, the "normal population." One hundred eight blood samples were collected from individuals known to have asthma and diagnosed as such by a physician. These samples compose, and are referred to herein as, the "asthma population." One hundred forty-six blood samples were collected from individuals known to have non-small cell lung cancers and diagnosed as such by a physician. These comprise, and are referred to herein as the "lung cancer population."

The same methods described in Example 1 were performed. FIGS. 2A-2E show the results obtained. These results provide guidance for selecting suitable biomarkers for the methods of this invention. In particular, the probability values for particular markers are useful in this regard.

FIG. 2E shows the probability associated with the effectiveness of various biomarkers for discriminating between the physiological state of different populations. Probability values of 0.1 or less are highlighted on this table to identify biomarkers of interest. Biomarkers used in preferred methods of this invention will have probability values of 0.05 or less, more preferably 0.01, and even more preferably 0.001 or less.

EXAMPLE 3

Human blood samples were collected from volunteers. Two hundred eighty eight samples were collected from individuals not known to have either non-small cell lung cancer or asthma. These samples comprise, and are referred to herein as, the "normal population." One hundred eighty blood samples were collected from individuals known to have asthma and diagnosed as such by a physician. These samples comprise, and are referred to herein as, the "asthma population." Three hundred sixty blood samples were collected from individuals known to have non-small cell lung cancers and diagnosed as such by a physician. These comprise, and are referred to herein as the "lung cancer population."

The same methods described in Example 1 were performed. A Panomics' Procarta Cytokine kit (Cat #PC1017) was also used. Antibodies for PAI-1 and Leptin were used from two different kits. Antibodies for PAI-1$^A$ and Leptin$^1$ were produced by Millipore. Antibodies for PAI-1$^B$ were produced by Panomics. FIGS. 3A-3E show the results obtained. These results provide guidance for selecting suitable biomarkers for the methods of this invention. In particular, the probability values for particular markers are useful in this regard.

FIG. 3E shows the probability associated with the effectiveness of various biomarkers for discriminating between the physiological state of different populations. Probability values of 0.1 or less are highlighted on this table to identify biomarkers of interest. Biomarkers used in preferred methods of this invention will have probability values of 0.05 or less, more preferably 0.01, and even more preferably 0.001 or less.

The data obtained was then segregated and analyzed by sex.

FIGS. 4A-4C show the average fluorescence intensity level of the biomarkers in the normal (NO), non-small cell lung cancer (LC), and asthma (AST) female population. FIG. 4D shows the percent change in the mean of each of the biomarkers in the AST v. NO female populations, LC v. NO female populations, and the AST v. LC female populations. FIG. 4E shows the probability associated with Student's t values calculated by comparing the mean fluorescence intensity measured for each biomarker, where the means to be compared are AST v. NO female populations, LC v. NO female populations, and the AST v. LC female populations, respectively.

The same information with respect to the male population is shown in FIG. 5A-5E.

Next, the female and male population data was compared. FIG. 6A shows the percent change in the mean of each of the biomarkers in the AST male population compared to the AST female population, the LC male population compared to the LC female population, and the NO male population compared to the NO female population. FIG. 6B shows the probability associated with Student's t values calculated by comparing the mean fluorescence intensity measured for each biomarker in the male and female populations from Example 3, where the means to be compared are the AST male and female populations, LC male and female populations, and the NO male and female populations, respectively.

EXAMPLE 4

The Kruskal-Wallis test is a well known, non-parametric statistical method. The data obtained from Example 3 was segregated by sex and analyzed using the Kruskal-Wallis (U test). Markers with probability values of 0.05 or less were considered significant. Markers showing marginally significant (probability between 0.051-0.10) and insignificant differences (probability above 0.10) were discarded. The results for the retained markers are shown in FIGS. 7-8.

FIG. 7A shows the percent change in the mean concentration of each of the biomarkers in the LC v. NO female populations, AST v. NO female populations, and the AST v. LC female populations. The scalar sum (i.e., the sum of the absolute values of the percent change for all three comparisons) is also provided and was used to rank the biomarkers. FIG. 7B shows the probability associated with be Kruskal-Wallis test calculated by comparing the concentration measured for each biomarker, where the populations to be compared are AST v. NO female populations, LC v. NO female populations, and the AST v. LC female populations, respectively.

The same information with respect to the male population is shown in FIGS. 8A and 8B.

The biomarkers showed unique gender- and disease-specific patterns. For unisex analysis of LC, 36 markers with an absolute change of at least 25% cutoff threshold and 32 markers with at least 50% cutoff were identified. For women, 32 markers with at least 25% cutoff and 30 with at least 50% cutoff were found. For men, 39 markers were found at least 25% cutoff and 37 at least 50% cutoff. Expression of four markers was unique for women with LC compared to NO: IL-8 and serum amyloid P (downregulated), serum amyloid A and C-reactive protein (all upregulated). Five markers were unique for men with LC compared to NO: insulin (downregulated), matrix metalloproteinases-7 and -8, resistin and hepatocyte growth factor (all unregulated). Three markers showed opposite patterns of expression: (i) VEGF was downregulated in women and upregulated in men with LC compared to NO; (ii) Leptin was upregulated in women and downregulated in men; and (iii) and MIP-1a were upregulated in men and downregulated in women with LC versus NO.

The invention provides for various methods of gender-based identification of disease states. For example the invention provides for methods of physiological characterization in a male subject comprising determining whether insulin is downregulated, and/or matrix metalloproteinases-7 and -8, resistin and hepatocyte growth factor are upregulated. Such patterns are indicative of disease. Assays within the contemplation of this invention include detecting abnormal up/down regulation of three, four, or five of these biomarkers in a male subject.

In another example, the invention provides for methods of physiological characterization in a female subject comprising determining whether IL-8 and/or serum amyloid P are downregulated, and/or serum amyloid. A and C-reactive protein are upregulated. Such patterns are indicative of disease. Assays within the contemplation of this invention include detecting abnormal up/down regulation of three or four of these biomarkers in a female subject.

EXAMPLE 5

Human blood samples were collected from volunteers. Thirty samples were collected from individuals not known to have either non-small cell lung cancer or asthma. The individuals known not to have either non-small cell lung cancer or asthma comprise, and are referred to herein as, the "normal population." Twenty-eight blood samples were collected from individuals known to have asthma and diagnosed as such by a physician. The individuals known to have asthma comprise, and are referred to herein as, the "asthma population." Thirty blood samples were collected from individuals known to have non-small cell lung cancers and diagnosed as such by a physician. The individuals known to have non-small cell lung cancer comprise, and are referred to herein as the "lung cancer population." Generally, as used herein, the term "lung cancer" or "lung cancers" is meant to refer to non-small cell lung cancers.

Eight to ten plasma specimens from each of the asthma population, normal population and lung cancer population were selected at random to be tested. Each plasma specimen from each population was subjected to a protease or digesting agent. Trypsin was used as the protease, and is desirable to be used as a protease because of its ability to make highly specific and highly predictable cleavages due to the fact that trypsin is known to cleave peptide chains at the carboxyl side of the lysine and arginine, except where a proline is present immediately following either the lysine or arginine. Although trypsin was used, it is possible to use other proteases or digesting agents. It is desirable to use a protease, or mixture of proteases, which cleave at least as specifically as trypsin.

The tryptic peptides, which are the peptides left by the trypsin after cleavage, were then separated from the insoluble matter by subjecting the specimens to a centrifugation and a capillary liquid chromatography, with an aqueous acetonitrile gradient with 0.1% formic acid using a 0.375×180 mm Supelcosil ABZ+ column on an Eksigent 2D capillary HPLC to effect chromatographic resolution of the generated tryptic peptides. This separation of the peptides is necessary because the electrospray ionization process is subject to ion co-suppression, wherein ions of a type having a higher proton affinity will suppress ion formation of ions having lower proton affinities if they are simultaneously eluting from the electrospray emitter, which in this case is co-terminal with the end of the HPLC column.

This methodology allows for the chromatographic separation of the large number of peptides produced in the tryptic digestions and helps to minimize co-suppression problems, thereby maximizing chances of the formation of pseudomolecular ion co-suppression, thereby maximizing ion sampling. The tryptic peptides for each specimen were then subjected to an LC-ESIMS. The LC-ESIMS separated each peptide in each specimen in time by passing the peptides in each specimen through a column of solvent system consisting of water, acetonitrile and formic acid as described above.

The peptides were then sprayed with an electrospray ionization source to ionize the peptides and produce the peptide pseudo-molecular ions as described above. The peptides were passed through a mass analyzer in the LC-ESIMS where molecular masses were measured for each peptide pseudo-molecular ion. After passing through the LC-ESIMS, mass spectral readouts were produced for the peptides present in each sample from the mass spectral data, namely the intensities, the molecular weights and the time of elution from a chromatographic column of the peptides. The mass spectral readouts are generally graphic illustrations of the peptide pseudo-molecular ion signals recorded by the LC-ESIMS, wherein the x-axis is the measurement of mass to charge ratio, the y-axis is the intensity of the pseudo-molecular ion signal. These data are then processed by a software system that controls the LC-ESIMS and acquires and stores the resultant data.

Once the mass spectral data was obtained and placed on the mass spectral readouts, a comparative analysis was performed wherein the mass spectral readouts of each plasma specimen tested in the LC-ESIMS for each population was performed, both interpathologically and intrapathologically. The mass spectral peaks were compared between each specimen tested in the normal population. The mass spectral peaks were then compared between each specimen tested in the asthma population and the lung cancer population. Once the intrapathological comparisons were performed, interpathological comparisons were performed wherein the mass spectral readouts for each specimen tested in the LC-ESIMS for the asthma population was compared against each specimen tested in the normal population. Likewise, the mass spectral readouts for each specimen tested in the LC-ESIMS for the lung cancer population was compared against each specimen tested in the normal population.

Peptides with mass spectral readouts that indicated the peptide intensities were inconsistently differentially expressed intrapathologically or were not substantially altered (less than 10 fold variance in intensity) when comparing the asthma population or lung cancer population to the normal population were determined to be insignificant and excluded. Generally, the exclusion criteria used involved comparing the peptide peak intensities for at least half of the identified characteristic peptides for a given protein across at least ten data sets derived from the analysis of individual patient plasma specimens from each pathology. If the intensity of the majority of peptide peaks derived from given protein were at least 10 fold higher in intensity for 80% of the plasma data sets, the protein was classed as differentially regulated between the two pathologic classes.

However, the identity of the proteins giving rise to the peptides that were observed to be differentially regulated were unknown and needed to be identified. To make the identification of the proteins, peptide pseudo-molecular ion signal intensities were compared across known databases which contain libraries of known proteins and peptides and suspected proteins and peptides.

The mass spectral readouts of the tryptic digests for each specimen from each of the normal, lung cancer and asthma population were inputted into a known search engine called MASCOT. MASCOT is a search engine known in the art which uses mass spectrometry data to identify proteins from four major sequencing databases, namely the MSDB, NCBInr, SwissProt and dbEST databases. These databases contain information on all proteins of known sequence and all putative proteins based on observation of characteristic protein transcription initiation regions derived from gene sequences. These databases are continually checked for accuracy and redundancy and are subject to continuous addition as new protein and gene sequences are identified and published in the scientific and patent literature.

Search criteria and parameters were inputted into the MASCOT program and the mass spectral data from the mass spectral readouts for each population were run through the MASCOT program. The mass spectral data entered into the MASCOT program were for the all specimens of each pathology. The MASCOT program then ran the mass spectral data for the peptides inputted against the sequencing databases, comparing the peak intensities and masses of each peptide to the masses and peak intensities of known peptides and proteins. MASCOT then produced a search result which returned a candidate list of possible protein identification matches, commonly known as "significant matches" for each sample that was analyzed.

Significant snatches are determined by the MASCOT program by assigning a score called a "MOWSE score" for each specimen tested. The MOWSE score is an algorithm wherein the score is $-10*LOG_{10}(P)$, where P is the probability that the observed match is a random event, which correlates into a significance p value where p is less than 0.05, which is the generally accepted standard in the scientific community. MOWSE scores of approximately 55 to approximately 66 or greater are generally considered significant. The significance level varies somewhat due to specific search considerations and database parameters. The significant matches were returned for each peptide run, resulting in a candidate list of proteins.

Next, comparative analysis was performed using the same methods described in US 20090069189, which is hereby incorporated by reference in its entirety.

The data from the mass spectral readouts were cross checked with the significant matches to confirm the raw data, peak identities, charge multiplicities, isotope distribution and flanking charge states. A reverse search was then performed to add peptides to the candidate list which may have been missed by the automated search through the MASCOT program. The additional peptides were identified by selecting the "best match" meaning the single protein which substantially matched each parameter of the peptide compared, performing an in silico digest wherein the tryptic peptides and their respective molecular masses calculated based on the known amino acid or gene sequence of the protein. These predicted peptide masses were then searched against the raw mass spectral data and any peaks identified were examined and qualified as described above. Then, all of the peptides including those automatically identified by MASCOT and those identified by manual examination were entered into the mass list used by MASCOT. The refined match is then used to derive a refined MOWSE score.

As a result of the identification process, the protein Arginase-1 was determined to be significantly differentially expressed between the asthma population, lung cancer population and/or normal population. Other proteins identified using this method are BAC04615, Q6NSC8, CAF17350, Q6ZUD4, Q8N7P1, CAC69571, FERM domain containing protein 4, JCC1445 proteasome endopeptidase complex chain C2 long splice form, Syntaxin 11, AAK13083 and AAK130490. See US 20090069189, which is hereby incorporated by reference in its entirety.

Having identified a specific protein which is consistently differentially expressed in asthma and lung cancer patients, it is possible to diagnose these pathologies early in the progression of the diseases by subjecting proteins in a patient's plasma to tryptic digestion and analysis by the LC-ESIMS, obtaining the mass spectral data, and determining whether the mass spectral data includes peaks for one or more of Arginase-1, BAC04615, Q6NSC8, CAF17350, Q6ZUD4, Q8N7P1, CAC69571, FERM domain containing protein 4, JCC1445 proteasome endopeptidase complex chain C2 long splice form, Syntaxin 11, AAK13083, and AAK130490. The levels of any proteins found in the patient sample are then compared to the levels found in a normal population.

The amino acid sequence disclosed SEQ NO: 1 is the primary amino acid sequence known as of the date of filing this application for the protein BAC04615. The amino acid sequence disclosed in SEQ ID NO: 2 is the primary amino acid sequence known as of the date of filing this application for the protein Q6NSC8. The amino acid sequence disclosed in SEQ ID NO: 3 is the primary amino acid sequence known as of the date of filing this application for the protein CAF17350. The amino acid sequence disclosed in SEQ ID NO: 4 is the primary amino acid sequence known as of the date of filing this application for the protein Q6ZUD4. The amino acid sequence disclosed in SEQ ID NO: 5 is the primary amino acid sequence known as of the date of filing this application for the protein FERM domain containing protein 4. The amino acid sequence disclosed in SEQ ID NO: 6 is the primary amino acid sequence known as of the date of filing this application for the protein AAK13083. The amino acid sequence disclosed in SEQ ID NO: 7 is the primary amino acid sequence known as of the date of filing this application for the protein Q8N7P1. The amino acid sequence disclosed in SEQ ID NO: 8 is the primary amino acid sequence known as of the date of filing this application for the protein CAC69571. The amino acid sequence disclosed in SEQ ID NO: 9 is the primary amino acid sequence known as of the date of filing this application for the protein JCC1445 proteasome endopetidase complex chain C2 long splice. The amino acid sequence disclosed in SEQ ID NO: 10 is the primary amino acid sequence known as of the date of filing this application for the protein Syntaxin 11. The amino acid sequence disclosed in SEQ ID NO: 11 is the primary amino acid sequence known as of the date of filing this application for the protein AAK13049. The amino acid sequence disclosed in SEQ ID NO: 12 is the primary amino acid sequence known as of the date of filing this application for the protein Arginase-1.

EXAMPLE 6

Selected tissue specimens from asthma patients was subjected to the same methods described in Example 5. See also Application No. 61/176,437, hereby incorporated by reference in its entirety.

As a result of the identification process, the following proteins were determined to be significantly differentially expressed in the asthma patient:

| Accession Number | Gene or Protein | Suggested Function From Literature | Mass | Mowse Score | SEQ ID NO: |
|---|---|---|---|---|---|
| Q6ZR64 (Human) | FLJ46603 | hypothetical protein HBV preS1-transactivated protein 1 | 23397 | 51 | 13 |
| Q8WUX6 (Human) | AAH19232 | expressed in lung tissue | 12347 | 49 | 14 |
| Q5YA4 | CCDC52 protein fragment | potential role in regulation of RhoA GTPase | 11748 | 51 | 15 |
| Q5T2Z1 (Human) | DDA3 | activated by p53 | 25035 | 56 | 16 |
| OSHU7C | cytochrome c oxidase chain VIIc precursor | terminal component of the mitochondrial respiratory chain complex; conversion of redox energy to ATP | 7241 | 46 | 17 |

Having identified five specific proteins which are consistently differentially expressed in asthma patients, it is possible to diagnose these pathologies early in the progression of the diseases by subjecting proteins in a patient's tissue specimen to tryptic digestion and analysis by the LC-ESIMS, obtaining the mass spectral data, and determining whether the mass spectral data includes peaks for one or more of SEQ ID NOS: 13-17. The levels of any proteins found in the patient sample are then compared to the levels found in a normal population.

EXAMPLE 7

Diagnostic Test for Non-Small Cell Lung Cancer

A sample of a biological fluid is obtained from a patient for whom diagnostic information is desired. The sample is preferably blood serum or plasma. The concentration in the sample of seven (7) of the following 14 biomarkers is determined: IL-13, I-TAC, MCP-1, MMP-1, MPO, HGF, Eotaxin, MMP-9, MMP-7 SAA, Resistin, IL-5, and sVACM-1. The measured concentration from the sample for each biomarker is compared to the range of concentrations of that marker found in the same fluid in normal human individuals, a population of individuals diagnosed with asthma, and a population of individuals diagnosed with NSCLC. Deviation from the normal range is indicative of lung disease, and deviation from the range for the population of individuals with asthma is indicative of NSCLC. Tests on a patient using biomarkers from the same set of 14 may be used in analogous procedures for diagnosis of asthma or other reactive airway diseases.

EXAMPLE 8

Monitoring Therapy for Non-Small Cell Lung Cancer

A pretreatment sample of a biological fluid is obtained from a patient who has been diagnosed with NSCLS before any treatment for the disease. The sample is preferably blood serum or plasma. The concentration in the sample of eight (8) of the following 24 biomarkers is determined: IL-13, EGF, I-TAC, MMP-1, IL-12 (p70), Eotaxin, MMP-8 MCP-1, MPO, IP-10, SAA, HGF, MMP-9, MMP-12, Amylin (Total), MMP-7, IL-6, MIL-1β, Adiponectin, IL-10, IL-5, IL-4, SE-selecting, and MIP-1α. The measured concentration from the sample for each biomarker may be compared to the range of concentrations of that marker found in the same fluid in normal human individuals. After the pretreatment sample has been taken the patient undergoes therapeutic intervention comprising surgery followed by irradiation. Samples of the same fluid are taken after surgery, but before irradiation. Additional samples are taken after each irradiation session. The concentration in each sample of the same eight (8) biomarkers is determined. Changes in the level of expression of each biomarker are noted and compared with other symptoms of progression of the disease.

EXAMPLE 9

Selection of Predictive Biomarkers

A pretreatment sample of a biological fluid is obtained from a population of patients who have been diagnosed with NSCLS before any treatment for the disease. The sample is preferably blood serum or plasma. The concentration in the sample of the following 24 biomarkers is determined: IL-13, EGF, I-TAC, MMP-1, IL-12 (p70), Eotaxin, MMP-8, MCP-1, MPO, IP-10, SAA, HGF, MMP-9, MMP12, Amylin (Total), MMP-7, IL-6, MIL-1β, Adiponectin, IL-10, IL-5, IL-4, SE-selectin, and MIP-1α. The measured concentration from the sample for each biomarker is compared to the range of concentrations of that marker found in the same fluid in normal human individuals. After the pretreatment sample has been taken each patient undergoes therapeutic intervention comprising surgery followed by irradiation. Samples of the same fluid are taken after surgery, but before irradiation. Additional samples are taken after each irradiation session. The concentration in each sample of the 24 biomarkers is determined. Changes in the level expression of each biomarker are noted and compared with other symptoms of progression of the disease. All biomarkers whose level changes after therapy are identified.

EXAMPLE 10

Selection of Susceptible Patients

A sample of a biological fluid is obtained from a patient who has been diagnosed with NSCLS. The sample is preferably blood serum or plasma. The concentration in the sample of each of the biomarkers identified in the previous example is determined, and patients for whom the highest number of biomarkers show values deviating from normal are selected for treatment.

EXAMPLE 11

Diagnostic Test for Non-Small Cell Lung Cancer in Male Subject

A sample of a biological fluid is obtained from a male patient for whom diagnostic information is desired. The sample is preferably blood serum or plasma. The concentration in the sample of seven (7) of the following 14 biomarkers is determined: I-TAC, MPO, HGF, MMP-1, MMP-8, Eotaxin, IL-8, MMP-7, IP-10, sVACM-1, L-10, Adiponectin, SAP, and IFN-γ. The measured concentration from the sample for each biomarker is compared to the range of concentrations of that marker found in the same fluid in normal human male individuals, a population of male individuals diagnosed with asthma, and a population of male individuals diagnosed with NSCLC. Deviation from the normal range is indicative of lung disease, and deviation from the range for the population of individuals with asthma is indicative of NSCLC. Tests on a patient using biomarkers from the same set of 14 may be used in analogous procedures for diagnosis of asthma or other reactive airway diseases.

EXAMPLE 12

Alternative Test for Non-small Cell Lung Cancer in a Male Subject

Many, if not all, of the biomarkers identified in Tables 1-15 participate in communications pathways of the sort described above. Some of the biomarkers are related to each other as first order interactors. Selection of markers for use in a diagnostic or prognostic assay may be facilitated using known relationships between particular biomarkers and their first order interactors. The known communication relationships between the biomarkers listed on Table 16B can be seen in FIG. 9, generated by the Ariadne system. FIG. 9 shows that first order interactors of HGF (Hepatocyte Growth Factor) include sFasL (soluble Fas ligand), PAI-1 (serpin Plasminogen Activator Inhibitor 1) (active/total), Ins (Insulin; which also includes C-peptide), EGF (Epidermal Growth Factor), MPO (Myeloperoxidase), and MIF (Migration Inhibitory Factor). Other interactors (not first order) include RETN (resistin, xcp1), SAA1 (Serum Amyloid A, SAA), CCL11 (Eotaxin), LEP (Leptin) and CXCL11 (Chemokine (C-X-C motif) ligand 11, Interferon-inducible T-cell alpha chemoattractant (I-TAC) or Interferon-gamma-inducible protein 9 (IP-9)). In addition, FIG. 9 shows that two biomarkers MMP1 and MMP-8 (Matrix Metalloproteinases 1 and 8) are not on a communication pathway with HGF.

One way to maximize the information collected by measuring a selection of biomarkers, is to select a plurality of biomarkers such that biomarkers which are not in the same communication pathway are included in the collection. Using the list of biomarkers in Table 16B, it appears that if the levels of at least HGF or another biomarker that is a first order interactor with HGF, and MMP-8 are abnormal in a male subject, the likelihood that the subject has lung cancer is much higher. If the level of MMP-1 is also abnormal, then the likelihood is even higher. Thus, one method according to the present invention for diagnosing lung cancer in a male subject would be to determine the level of at least HGF or another biomarker that is a first order into actor with HGF, and MMP-8, and the levels compared to the range expected for a normal population to see of the levels of these biomarkers is abnormal. In a preferred mode, the diagnostic method would also include determining whether the level of MMP-1 was normal. More preferable, one or more of CXCL11, LEP, SAA1 and/or RETN would also be determined, and the levels compared to the range expected for a population of normal individuals. The more of these biomarkers which are present at an abnormal level, the more likely that the subject has lung cancer.

EXAMPLE 13

Monitoring Therapy for Non-Small Cell Lung Cancer in a Male

A pretreatment sample of a biological fluid is obtained from a male patient who has been diagnosed with NSCLS before any treatment for the disease. The sample is preferably blood serum or plasma. The concentration in the sample of eight (8) of the following 24 biomarkers is determined: IL-13, I-TAC, EGF, MPO, HGF, MMP-1, MMP-8, MIF, Eotaxin, IL-12 (p70), MCP-1, MMP-9, SAA, IP-10, Amylin (Total), MMP-7, Resistin, IL-6, MIP-1β, TNF-α, IL-8, IL-5, CRP, and IL-10. The measured concentration from the sample for each biomarker may be compared to the range of concentrations of that marker found in the same fluid in normal human individuals. After the pretreatment sample has been taken the patient undergoes therapeutic intervention comprising surgery followed by irradiation. Samples of the same fluid are taken after surgery, but before irradiation. Additional samples are taken after each irradiation session. The concentration in each sample of the same eight (8) biomarkers is determined. Changes in the level of expression of each biomarker are noted and compared with other symptoms of progression of the disease.

EXAMPLE 14

Selection of Predictive Biomarkers

A pretreatment sample of a biological fluid is obtained from a population of male patients who have been diagnosed with NSCLS before any treatment for the disease. The sample is preferably blood serum or plasma. The concentration in the sample of the following 24 biomarkers is determined: IL-13, I-TAC, EGF, MPO, HGF, MMP-1, MMP-8, MIF, Eotaxin, IL-12 (p70), MCP-1, MMP-9, SAA, IP-10, Amylin (Total), MMP-7, Resistin, IL-6, MIP-1β, TNF-α, IL-8, IL-5, CRP, and IL-10. The measured concentration from the sample for each biomarker is compared to the range of concentrations of that marker found in the same fluid in normal human individuals. After the pretreatment sample has been taken each patient undergoes therapeutic intervention comprising surgery followed by irradiation. Samples of the same fluid are taken after surgery, but before irradiation. Additional samples are taken after each irradiation session. The concentration in each sample of the 24 biomarkers is determined. Changes in the level of expression of each biomarker are noted and compared with other symptoms of progression of the disease. All biomarkers whose level changes after therapy are identified.

EXAMPLE 15

Selection of Susceptible Patients

A sample of a biological fluid is obtained from a male patient who has been diagnosed with NSCLS. The sample is preferably blood serum or plasma. The concentration in the sample of each of the biomarkers identified in the previous example is determined, and patients for whom the highest number of biomarkers show values deviating from normal are selected for treatment.

The invention claimed is:

1. A method of diagnosing lung disease in a subject comprising determining the extent of expression of at least five (5) biomarkers in a physiological sample of said subject, said biomarkers being myeloperoxidase (MPO), matrix metallopeptidase 9 (MMP-9), serum amyloid A (SAA), resistin, and interleuking 8 (IL-8), wherein the extent of expression of said biomarker is indicative of a lung disease.

2. The method of claim 1, wherein the lung disease is non-small cell lung cancer and wherein the level of expression of said biomarkers is indicative of the presence or development of non-small cell lung cancer in the subject.

3. The method of claim 1, wherein determining the level of expression comprises performing a quantitative multiplex immunoassay.

4. The method of claim 1, wherein the method further comprises obtaining a physiological sample of said subject.

5. The method of claim 1, wherein the physiological sample is a biological fluid.

6. The method of claim 1, wherein the subject is a mammal.

7. A method of measuring a subset of biomarkers by immunoassay in a subject comprising
(a) obtaining a physiological sample from the subject,
(b) measuring in the sample a set of five (5) biomarkers consisting of myeloperoxidase (MPO), matrix metallopeptidase 9 (MMP-9), serum amyloid A (SAA), resistin, and interleuking 8 (IL-8), by immunoassay.

8. The method of claim 7, wherein the subject is a human male.

9. The method of claim 7, wherein the subject is a human female.

10. The method of claim 7, wherein the measuring comprises performing a quantitative multiplex immunoassay.

11. The method of claim 7, wherein the subject is a mammal.

12. The method of claim 11, wherein the mammal is a human.

13. The method of claim 7, wherein the physiological sample is biological fluid selected from the group consisting of blood, serum, and plasma.

14. The method of claim 1, wherein the method further comprises measuring at least one biomarker selected from the group consisting of Monocyte Chemotactic Protein 1 ("MCP-1"), Matrix Metalloproteinase 7 ("MMP-7"), Interleukin-5 ("IL-5"), Leptin, Interleukin-12 (p70), ("IL-12"), Interleukin-4 ("IL-4"), Interleukin-7 ("IL-7"), Interleukin-10 ("IL-10"), Macrophage Migration Inhibitory Factor ("MIF"), Soluble CD40 Liquid ("sCD40 ligand"), Soluble Intracellular Adhesion Molecule 1 ("sICAM-1"), Hepatocyte Growth Factor ("HGF"), Interleukin-13 ("IL-13"), Chemokine (C-X-C motif) Ligand 11 ("I-TAC"), Matrix Metalloproteinase 1 ("MMP-1"), Eotaxin, C-X-C Motif Chemokine 10 ("IP-10"), Soluble Vascular Cell Adhesion Molecule ("sVCAM"), Adiponectin, C-Reactive Protein ("CRP"), C-Peptide, Matrix Metalloproteinase 3 ("MMP-3"), Serum Amyloid P ("SAP"), Interleukin-1 receptor antagonist ("IL-IRA"), Interleukin-15 ("IL-15"), Epidermal Growth Factor ("EGF"), Matrix Metalloproteinase 8 ("MMP-8"), Interleukin-6 ("IL-6"), ("IL-6"), Matrix Metalloproteinase 12 ("MMP-12"), Plasminogen Activator Inhibitor 1 ("PAI-1"), total Amylin, Interleukin-1α ("IL-1α"), "sFS1", Macrophage Inflammatory Protein 1β ("MIP-1β"), sE-selectin, Interleukin-17 ("IL-17"), Granulocyte Macrophage Colony Stimulating Factor ("GM-CSF"), Granulocyte Colony Stimulating Factor ("G-CSF"), Transforming Growth Factor α ("TGF-α"), interferon-γ ("IFN-γ"), Fractalkine, Vascular Endothelial Growth Factor ("VEGF"), Interleukin-12 (p40) ("IL-12"), "Sfas", Interleukin-1β ("IL-1β"), Interleukin-2 ("IL-2"), Macrophage Inflammatory Protein 1α ("MIP-1α"), Insulin, Glucagon Like Protein-1 ("GLP-1"), Tumor Necrosis Factor α ("TNF-α"), Metalloproteinase 2 ("MMP-2"), Metalloproteinase 13 ("MMP-13"), Interleukin-12 (p40) ("IL-12"), or a combination thereof.

15. The method of claim 1, wherein the subject is a human.

16. The method of claim 5, wherein the biological fluid is blood serum or plasma.

* * * * *